US011963980B2

(12) United States Patent
Paulos et al.

(10) Patent No.: US 11,963,980 B2
(45) Date of Patent: Apr. 23, 2024

(54) ACTIVATED CD26-HIGH IMMUNE CELLS AND CD26-NEGATIVE IMMUNE CELLS AND USES THEREOF

(71) Applicant: MUSC FOUNDATION FOR RESEARCH DEVELOPMENT, Charleston, SC (US)

(72) Inventors: Chrystal M. Paulos, Charleston, SC (US); Michelle H. Nelson, Charleston, SC (US); Stefanie R. Bailey, Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 573 days.

(21) Appl. No.: 16/095,828

(22) PCT Filed: Apr. 25, 2017

(86) PCT No.: PCT/US2017/029334
§ 371 (c)(1),
(2) Date: Oct. 23, 2018

(87) PCT Pub. No.: WO2017/189526
PCT Pub. Date: Nov. 2, 2017

(65) Prior Publication Data
US 2019/0247431 A1 Aug. 15, 2019

Related U.S. Application Data

(60) Provisional application No. 62/356,894, filed on Jun. 30, 2016, provisional application No. 62/327,414, filed on Apr. 25, 2016.

(51) Int. Cl.
*A61K 35/17* (2015.01)
*A61K 38/19* (2006.01)
*A61K 39/00* (2006.01)
*A61P 35/00* (2006.01)
*C12N 5/0783* (2010.01)
*C12N 5/16* (2006.01)

(52) U.S. Cl.
CPC ............ *A61K 35/17* (2013.01); *A61K 38/19* (2013.01); *A61K 39/0011* (2013.01); *A61K 39/001156* (2018.08); *A61K 39/001168* (2018.08); *A61P 35/00* (2018.01); *C12N 5/0636* (2013.01); *C12N 5/163* (2013.01); A61K 2039/5156 (2013.01); A61K 2039/5158 (2013.01); C12N 2510/00 (2013.01); G01N 2800/52 (2013.01)

(58) Field of Classification Search
CPC ........ A61K 35/17; A61P 35/00; C12N 5/0636
See application file for complete search history.

(56) References Cited

U.S. PATENT DOCUMENTS

| 2003/0031665 A1* | 2/2003 | Dang ..................... A61K 38/19 424/141.1 |
| 2006/0093553 A1 | 5/2006 | Dang et al. |
| 2006/0121005 A1* | 6/2006 | Berenson ............. C12N 5/0636 435/372 |
| 2013/0309250 A1 | 11/2013 | Cogswell et al. |
| 2013/0330325 A1 | 12/2013 | Grabe et al. |
| 2014/0030806 A1 | 1/2014 | Dudley et al. |
| 2014/0086923 A1 | 3/2014 | Faget et al. |
| 2015/0306141 A1 | 10/2015 | Jensen et al. |

OTHER PUBLICATIONS

Bailey et al., Defining the role of the novel CD4+CD26high T cell subset in adoptive cancer immunotherapy (VAC11P.1001). The Journal of Immunology, vol. 192, 1 Supplement 205.2 (2014), pp. 1-2. (Year: 2014).*
Bengsch et al., Human TH17 cells express high levels of enzymatically active dipeptidylpeptidase IV (CD26). The Journal of Immunology, vol. 188 (2012) pp. 5438-5447. (Year: 2012).*
Golubovskaya et al., Different subsets of T cells, memory, effector functions, and CAR-T immunotherapy. Cancers, vol. 8, No. 3 (Mar. 15, 2016) https://doi.org/10.3390/cancers8030036. (Year: 2016).*
Li et al., Comparison of anti-CD3 and anti-CD28 coated beads with soluble anti-CD3 for expanding human T cells: Differing impact on CD8 T cell phenotype on responsiveness to restimulation. Journal of Translational Medicine, vol. 8 (2010) article 104. (Year: 2010).*
Teschner et al., In vitro stimulation and expansion of human tumour-reactive CD8+ cytotoxic T lymphocytes by anti-CD3/CD28/CD137 magnetic beads. Scandinavian Journal of Immunology, vol. 74, No. 2 (2011) pp. 155-164. (Year: 2011).*
Acosta-Rodriguez et al., "Surface phenotype and antigenic specificity of human interleukin 17-producing T helper memory cells," *Nat. Immunol.* 8:639-646, 2007.
Aldinucci et al., "CD26 expression correlates with a reduced sensitivity to 2'-deoxycoformycin-induced growth inhibition and apoptosis in T-cell leukemia/lymphomas," *Clinical Cancer Research*, 10:508-520, 2004.
Bailey et al., "Defining the role of the novel CD4+CD26high T cell subset in adoptive cancer immunotherapy (VAC11P.1001)," *The Journal of Immunology*, 192(1 Supplement 205.2), pp. 1-2, 2014.
Bailey et al., "The quantity of CD26 on helper T cells correlates with the efficacy of adoptive cancer immunotherapy (TUM2P. 1008)," *The Journal of Immunol*, 194 (1 Supplement 69.5), pp. 1-3, 2015.
Bailey et al., Abstract No. 204, "Unraveling the Mechanisms Behind the Potent Antitumor Activity of CD4+CD26high T Cells in Adoptive Cell Therapy," In: 49th Annual Perry V Halushka MUSC 2014 Research Day, Medical University of South Carolina, Charleston, SC, Nov. 13-14, 2014.

(Continued)

*Primary Examiner* — Kara D Johnson
(74) *Attorney, Agent, or Firm* — Parker Highlander PLLC

(57) ABSTRACT

Provided herein are methods for the production of activated CD26high T cells by co-stimulation with inducible coactivator (ICOS). Further provided are methods for treatment of cancer by administration of the of activated CD26high T cells as an adoptive T cell therapy.

23 Claims, 35 Drawing Sheets

Specification includes a Sequence Listing.

(56) References Cited

OTHER PUBLICATIONS

Barreira da Silva et al. "Dipeptidylpeptidase 4 inhibition enhances lymphocyte trafficking, improving both naturally occurring tumor immunity and immunotherapy," *Nat. Immunol.*, 16:850-858, 2015.

Bengsch et al., "Human Th17 cells express high levels of enzymatically active dipeptidylpeptidase IV (CD26)," *J. Immunol.*, 188:5438-5447, 2012.

Chang et al., "T helper 17 cells play a critical pathogenic role in lung cancer," *Proc. Natl. Acad. Sci. USA*, 111:5664-5669, 2014.

Gattinoni et al., "A human memory T cell subset with stem cell-like properties," *Nat. Med.*, 17:1290-1297, 2011.

Guedan et al., "ICOS-based chimeric antigen receptors program bipolar $T_H17/T_H1$ cells," *Blood*, 124(7):1070-1080, 2014.

Hatano et al., "CD26-mediated co-stimulation in human CD8(+) T cells provokes effector function via pro-inflammatory cytokine production," *Immunology*, 138(2):165-172, 2013.

Kim and Cantor, "CD4 T-cell subsets and tumor immunity: the helpful and the not-so-helpful," *Cancer Immunol Res.*, 2:91-98, 2014.

Lee et al., "Induction and molecular signature of pathogenic $T_H17$ cells," *Nat. Immunol.*, 13:991-999, 2012.

Moon et al., "Expression of a functional CCR2 receptor enhances tumor localization and tumor eradication by retargeted human T cells expressing a mesothelin-specific chimeric antibody receptor," *Clin Cancer Res.*, 17:4719-4730, 2011.

Muranski et al., "Th17 cells are long lived and retain a stem cell-like molecular signature," *Immunity*, 35:972-985, 2011.

Muranski et al., "Tumor-specific Th17-polarized cells eradicate large established melanoma," *Blood*, 112:362-373, 2008.

Paulos et al., "The inducible costimulator (ICOS) is critical for the development of human T(H)17 cells," *Sci. Transl. Med.*, 2:55ra78, 2010.

PCT International Search Report and Written Opinion issued in International Application No. PCT/US2017/029334, dated Aug. 29, 2017.

Salgado et al., "CD26: a negative selection marker for human Treg cells," *Cytometry A*, 81(10):843-855, 2012.

Samimi et al., "Increased programmed death-1 expression on CD4+ T cells in cutaneous T-cell lymphoma: implications for immune suppression," *Arch. Dermatol.*, 146(12):1382-1388, 2010.

Simpson et al., "Regulation of CD4 T cell activation and effector function by inducible costimulatory (ICOS)," *Current Opinion in Immunology*, 22:321-332, 2010.

* cited by examiner

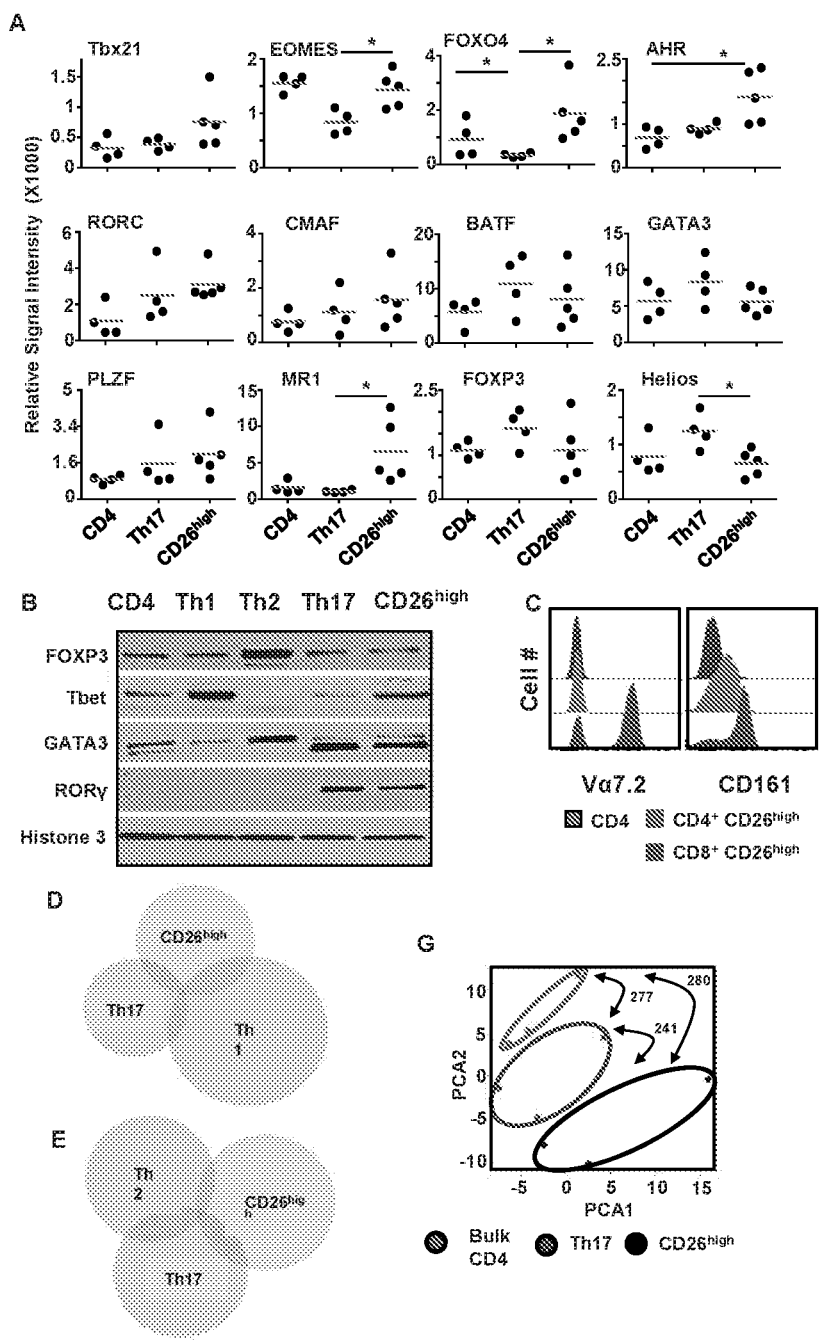
FIGS. 14A-E, 14G

| Target | Clone | Fluorophore | Provider |
|---|---|---|---|
| am-CD4 | GK1.5 | APC Cy7 | BD Biosciences |
| am-Vβ14 | 14.2 | FITC | BD Biosciences |
| am-CD26 | H194-112 | PE | BioLegend |
| ah-CD26 | C5a5b | PE | |
| ah-CD4 | OKT4 | APC Cy 7 | |
| ah-CD25 | BC96 | FITC | |
| ah-CD45RA | HI10U | PerCP Cy5.5 | |
| ah-CD45RO | UCHL1 | APC | |
| ah-OX40 | ACT35 | PE Cy7 | |
| ah-CD154/CD40L | 24-31 | AF488 | |
| ah-CCR6 | G034E3 | PE Cy7 | |
| ah-CXCR3 | G025H7 | BV421 | |
| ah-CD127 | A019D5 | PE Cy7 | |
| ah-CD39 | A1 | PE Cy7 | |
| ah-CD45 | HI30 | Pacific Blue | |
| ah-FoxP3 | 150D | AF647 | |
| ah-Helios | 22F6 | Helios | |
| ah-IL-22 | 516406 | AF647 | |
| ah-TNFα | MAb11 | PE Cy7 | |
| ah-Granzyme B | 515403 | FITC | |
| ah-RANTES | VL1 | PerCP Cy5.5 | |
| ah-CD4 | RPAT4 | V500 | BD Biosciences |
| ah-PD1 | M1H4 | FITC | |
| ah-CD28 | CD28.2 | APC H7 | |
| ah-CCR7 | | PE Cy7 | |
| ah-CCR2 | 48607 | AF647 | |
| ah-CCR5 | 2D7 | V450 | |
| ah-IL-2 | MQ1-17H12 | PE Cy7 | |
| ah-IFNγ | B27 | V450 | |
| ah-IL-17A | N49-653 | PerCP Cy5.5 | |
| ah-CD107A | H4A3 | APC H7 | |
| ah-MIP1β | | PerCP Cy5.5 | |
| ah-IL-4 | | FITC | |
| Streptavidin | | V500 | |
| ah-CD69 | FN50 | APC | eBioscience |
| ah-ICOS | ISA-3 | Biotin | |
| ah-CD161 | HP-3G10 | PerCP Cy5.5 | |
| ah-CCR4 | | FITC | R&D Industries |
| ah-CCR8 | | PerCP Cy5.5 | R&D Industries |

FIG. 29

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial sequence
<220> FEATURE:
<223> OTHER INFORMATION: Synthetic peptide

<400> SEQUENCE: 1

Ser Gly His Asn Cys Gly Thr Cys Arg Pro Gly Trp Arg Gly Ala Ala
1               5                   10                  15

Cys Asn Gln Lys Ile Leu Thr Val Arg
            20                  25
```

ACTIVATED CD26-HIGH IMMUNE CELLS AND CD26-NEGATIVE IMMUNE CELLS AND USES THEREOF

The present application is a national phase application under 35 U.S.C. § 371 of International Application No. PCT/US2017/029334, filed Apr. 25, 2017, which claims the priority benefit of U.S. Provisional Application Ser. No. 62/327,414, filed Apr. 25, 2016, and Ser. No. 62/356,894, filed Jun. 30, 2016, the entire contents of which are being hereby incorporated by reference.

The invention was made with government support under Grant No. R01 CA175061 awarded by the National Institutes of Health. The government has certain rights in the invention.

Pursuant to 37 C.F.R. 1.821(c), a sequence listing is submitted herewith as an ASCII compliant text file named "MESCP0098US_ST25.txt", created on Oct. 22, 2018 and having a size of ~1 kilobytes. The content of the aforementioned file is hereby incorporated by reference in its entirety.

BACKGROUND OF THE INVENTION

1. Field of the Invention

The present invention relates generally to the field of immunology and medicine. Particularly, it concerns methods and compositions for treating cancer, such as by the administration of $CD26^{high}$ T cells.

2. Description of Related Art

In response to costimulation and cytokine cues, naïve $CD4^+$ T cells differentiate into one of several T helper (Th) subsets. These subsets are commonly identified by their ability to secrete IFN-$\gamma$, IL-4 or IL-17A and are termed Th1, Th2 and Th17 cells, respectively. Each subset has been reported to enhance immune responses against cancer in murine models Kim and Cantor, 2014. In contrast, regulatory $CD4^+$ T cells that express high CD25 and master transcription factor FoxP3, dampen immune responses to tumors. Traditionally, IFN-$\alpha$-secreting Th1 cells have been regarded as the most effective antitumor T cell subset in various murine models of cancer. However, recent reports demonstrated that murine Th17 cells are more effective at killing tumor than their Th1 or IL-2-expanded $CD4^+$ T cell cohorts (Muranski et al., 2008; Chang et al., 2014). While the role of distinct murine $CD4^+$ T cell subsets are clearly defined, there remains a need to identify a human $CD4^+$ T cell subset with durable antitumor memory responses.

SUMMARY OF THE INVENTION

In a first embodiment, there is provided a method (e.g., an in vitro method) for producing activated $CD26^{high}$ immune effector cells comprising: (a) obtaining a population of $CD26^{high}$ immune effector cells; and (b) stimulating the population of $CD26^{high}$ immune effector cells with inducible costimulator (ICOS), thereby obtaining activated $CD26^{high}$ immune effector cells. In some aspects, the immune effector cells are T cells, B cells, natural killer (NK) cells and any other immune cells that can trigger directly or indirect responses to the desired target. In some aspects, the T cells are $CD4^+$ and/or $CD8^+$ T cells. In certain aspects, the T cells are T helper 1 (TH1) cells, T helper 2 (TH2) cells, TH17 cells, cytotoxic T cells, regulatory T cells, natural killer T cells, naïve T cells, memory T cells, MAIT, ILCs or gamma delta T cells. In some aspects, stimulating with ICOS comprises culturing the population of $CD26^{high}$ immune effector cells in a culture comprising anti-ICOS coated beads. In some aspects, the cell are further stimulated with one or more co-stimulatory agents selected from the group consisting of 41BB, CD28, CD40L, OX40, a PD-1 inhibitor, and a CTLA4 inhibitor or any other co-stimulatory of co-inhibitory molecule. Also, cytokines, such as but not limited to IL-2, IL-7, IL-12, IL-15, IL-21, IL-23, IFN-gamma, can augment the expression or generation of immune cells that express CD26.

In certain aspects, the beads are magnetic beads. In additional aspects, the culture further comprises anti-CD3 beads. In other aspects, the culture further comprises at least one growth factor. In a specific aspect, the at least one growth factor may be IL-2. In some particular aspects, the culturing is for 5 day to 10 days or even longer.

In further aspects, step (a) comprises sorting a population of total $CD4^+$ T cells, $CD8^+$ T cells, NK cells and/or any other immune cells for cells with high expression of the cell surface marker CD26. In some aspects, the sorting is further defined as fluorescence-activated cell sorting (FACS) or beads or size-based strategies. In certain aspects, the population of total $CD4^+$ T cells, $CD8^+$ T cells, and/or NK cells is isolated from peripheral blood or cord blood. In some aspects, the population of total $CD4^+$ T cells, $CD8^+$ T cells, and/or NK cells is isolated from peripheral blood mononuclear cells. In another aspect, the $CD26^{high}$ immune effector cells are engineered to express to express a T cell receptor (TCR) or chimeric antigen receptor (CAR) receptor.

In some specific aspects, the TCR or CAR comprises an intracellular signaling domain, a transmembrane domain, and/or an extracellular domain comprising an antigen binding region. In certain particular aspects, the antigen binding region is an F(ab')2, Fab', Fab, Fv, or scFv. In still further aspects, the intracellular signaling domain may be a T-lymphocyte activation domain. In other aspects, the intracellular signaling domain comprises CD3$\xi$, CD28, OX40/CD134, 4-1BB/CD137, Fc$\epsilon$RI$\gamma$, ICOS/CD278, ILRB/CD122, IL-2RG/CD132, DAP molecules, CD70, cytokine receptor, CD40, or a combination thereof or any other type of costimulators/cytokines. In additional aspects, the intracellular signaling domain comprises CD3$\xi$ and 4-1BB/CD137. In some aspects, the transmembrane domain comprises CD28 transmembrane domain, IgG4Fc hinge, Fc regions, CD4 transmembrane domain, the CD3 transmembrane domain, cysteine mutated human CD3$\xi$ domain, CD16 transmembrane domain, CD8 transmembrane domain, or erythropoietin receptor transmembrane domain.

In certain aspects, the antigen binding region binds a tumor associated antigen. In some particular aspects, the tumor associated antigen is selected from the group consisting of tEGFR, Her2, CD19, CD20, CD22, mesothelin, CEA, CD23, CD24, CD30, CD33, CD38, CD44, EGFR, EGP-2, EGP-4, EPHa2, ErbB2, FBP, MAGE-A1, MUC1, NY-ESO-1, and MART-1. In a further specific aspect, the tumor associated antigen may be mesothelin.

In still further aspects, the $CD26^{high}$ immune effector cells are not polarized by cytokine programming. In other aspects, the activated $CD26^{high}$ immune effector cells co-secrete more than 2 (e.g., 3, 4, or 5) of the cytokines selected from the group consisting of IL-17A, IFN-$\gamma$, TNF-$\alpha$, MIP-1$\beta$ and IL-2. In some specific aspects, the activated $CD26^{high}$ immune effector cells have an increased secretion of one or more of the cytokines selected from the group consisting of IL-17A, IFN-$\gamma$, TNF-$\alpha$, and IL-2 as compared to the population of total $CD4^+$ T cells, $CD8^+$ T cells, NK cells and or any other type of immune cells. In other aspects, the activated CD26$^{high}$ immune effector cells have an increased secretion of one or more of the cytotoxic molecules selected from the group consisting of perforin, granzyme, and IL-23R as compared to the population of total CD4$^+$ T cells, CD8$^+$ T cells, and/or NK cells. In certain specific aspects, the activated CD26$^{high}$ immune effector cells have an increased secretion of Tbet as compared to the population of total CD4$^+$ T cells, CD8$^+$ T cells, and/or NK cells.

In additional aspects, the activated CD26$^{high}$ immune effector cells have low expression or essentially no expression of CD62L, CD45RA and/or CCR7. In another aspect, the activated CD26$^{high}$ CD4$^+$ T cells may have an effector memory phenotype. In some aspects, the activated CD26$^{high}$ CD4$^+$ T cells are capable of long-term engraftment in a mammal. In a particular aspect, the mammal is a human A further embodiment of the disclosure provides an isolated cell population comprising immune effector cells, wherein at least 10, such as at least 20, 25, 30, 40, 50, 75, or higher, percent of the immune effector cells are CD26$^{high}$ immune effector cells. In some aspects, the immune effector cells are T cells or NK cells. In certain aspects, the T cells are CD4$^+$ T cells and/or CD8$^+$ T cells. In some aspects, the CD4$^+$ T cells and/or CD8$^+$ T cells are isolated from peripheral blood or cord blood. In certain aspects, the CD4$^+$ T cells and/or CD8$^+$ T cells are isolated from peripheral blood mononuclear cells.

In some aspects, at least 35 percent of the immune effector cells are CD26$^{high}$ immune effector cells. In certain aspects, at least 50 percent of the immune effector cells are CD26$^{high}$ immune effector cells. In particular aspects, at least 55, 60, 65, 70, 75, 80, 85, 90, 91, 92, 93, 94, 95, 96, 97, 98, or 99 percent of the immune effector cells are CD26$^{high}$ immune effector cells.

In some aspects, the CD26$^{high}$ immune effector cells have been activated by ICOS. In certain aspects, the CD26$^{high}$ immune effector cells have been activated by ICOS, 41BB, CD28, CD40L, OX40, a PD-1 inhibitor, a CTLA4 inhibitor, or any other cosimulatory, cytokine or coinhibitory receptor and or a combination thereof.

In certain aspects, the isolated cell population may be produced according to the methods of the embodiments and aspects described herein.

In yet a further embodiment there is provided a method of treating cancer in a subject comprising administering an effective amount of T cells to the subject, wherein at least 10 percent of the T cells are CD26$^{high}$ T cells. In some aspects, at least 20, 30, 40, 50, 60, 70, 75, 80, 90, 95, 96, 97, 98, or 99 percent of the T cells are CD26$^{high}$ T cells. In some aspects, the CD26$^{high}$ T cells comprise activated CD26$^{high}$ T cells produced by the methods of the embodiments.

In some aspects, the CD26$^{high}$ T cells are produced by engineering T cells to express CD26. In certain aspects, engineering comprises introducing CD26-encoding mRNA to the T cells.

In some aspects, the T cells are CD4$^+$ T cells, CD8$^+$ T cells and/or other immune cells. In some aspects, the activated CD26$^{high}$ CD4$^+$ T cells are autologous. In additional aspects, the method further comprises lymphodepletion of the subject prior to administration of the activated CD26$^{high}$ CD4$^+$ T cells. In further aspects, lymphodepletion comprises administration of cyclophosphamide and/or fludarabine. In other aspects, the method further comprises administering at least a second therapeutic agent. For example, the at least a second therapeutic agent may comprises CD8$^+$ T cells or chemotherapy, immunotherapy, surgery, radiotherapy, or biotherapy. In a particular aspect, the immunotherapy is an immune checkpoint inhibitor. In further aspects, activated CD26$^{high}$ CD4$^+$ T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.

In certain aspects, the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL) or any other type of cancer. In other aspects, the cancer may be mesothelioma, pancreatic cancer, or ovarian cancer or any other type of cancer. In some aspects, said subject is a human subject.

In another embodiment, there is provided a method of predicting response to or monitoring the efficacy of an immunotherapy in a patient comprising measuring the percentage of CD26$^{high}$ cells in the blood of the subject, wherein if the subject has an elevated level of CD26$^{high}$, then the patient is predicted to have a favorable response to the immunotherapy. In some aspects, the elevated level of CD26$^{high}$ cells is at least 10% of the total T cell population in the subject. In some aspects, the subject is human. In certain aspects, the elevated level of CD26$^{high}$ cells is at least 11, 12, 13, 14, 15, 20, 25, 30, 35, 40, 45, 50, 55, 60, 65, 70, 75, 80, or 90 percent of the total T cells population in the subject. In some aspects, measuring comprises magnetic-activated cell sorting or fluorescence-activated cell sorting for CD26$^{high}$ cells.

In certain aspects, the immunotherapy comprises adoptive transfer of a T cell population. In some aspects, the immunotherapy is treatment with an immune checkpoint inhibitor, cytokines, chemotherapy or other immune modulator. In particular aspects, the immune checkpoint inhibitor is a PD-1 inhibitor or a CTLA-4 inhibitor. In some aspects, the PD-1 inhibitor is nivolumab, or pembrolizumab or other. In some aspects, the immunotherapy comprises administration of cancer cell antigens.

In some aspects, a favorable response to the immunotherapy comprises reduction in tumor size or burden, blocking of tumor growth, reduction in tumor-associated pain, reduction in cancer associated pathology, reduction in cancer associated symptoms, cancer non-progression, increased disease free interval, increased time to progression, induction of remission, reduction of metastasis, or increased patient survival.

In a further embodiment, there is provided a method for treating a subject comprising administering an immunotherapy to a subject identified to have an elevated level of CD26$^{high}$ cells. In some aspects, the elevated level of CD26$^{high}$ cells is in at least 10% or more of the total T cell population in the subject. In certain aspects, the elevated level of CD26$^{high}$ cells is in at least 11, 12, 13, 14, 15, 20, 25, 30, 35, 40, 45, 50, 55, 60, 65, 70, 75, 80, or 90 percent of the total T cells population in the subject. In some aspects, the subject is human.

In certain aspects, the immunotherapy comprises adoptive transfer of a T cell population. In some aspects, the immunotherapy is treatment with an immune checkpoint inhibitor or any other type of therapy that modulates the immune system. In particular aspects, the immune checkpoint inhibitor is a PD-1 inhibitor or a CTLA-4 inhibitor. In some aspects, the PD-1 inhibitor is nivolumab, or pembrolizumab. In some aspects, the immunotherapy comprises administration of cancer cell antigens.

In some aspects, the subject has a cancer. In certain aspects, the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL). In particular aspects, the cancer is mesothelioma, melanoma, pancreatic cancer, or ovarian cancer or any other receptive malignancy.

In some aspects, the T cell population is an activated $CD26^{high}$ CD4$^+$ T population produced according to the methods of the embodiments. In certain aspects, the T cell population comprises CD4$^+$ and/or CD8$^+$ T cells. In some aspects, the T cell population comprises T helper 1 (TH1) cells, T helper 2 (TH2) cells, TH17 cells, cytotoxic T cells, regulatory T cells, natural killer T cells, naïve T cells, memory T cells, MAIT, ILCs or gamma delta T cells or any other immune cells.

In a further embodiment, there is provided an isolated cell population comprising immune effector cells, wherein at least 50, 60, 70, 80, 85, 90 or 95 percent of the immune effector cells are CD26neg immune effector cells. In some aspects, the immune effector cells are T cells or NK cells. In further aspects, the T cells are CD4+ T cells. In certain aspects, at least 96, 97, 98 or 99 percent of the immune effector cells are CD26 negative immune effector cells. In some aspects, the cell population is essentially free of CD26 positive cells. In some aspects, the cells are isolated from peripheral blood or cord blood. In further aspects, the cells are isolated from peripheral blood mononuclear cells.

A further embodiment of the invention provides a method of producing a cell population in accordance with the embodiments and aspects described above, comprising obtaining a cell sample and depleting the sample of CD26 positive cells. In certain aspects, the depleting comprises cell sorting. In other aspects, the depleting comprises passing the cell population over beads or through a column comprising immobilized anti-CD26 antibodies. In particular aspects, the depleting comprises contacting the population with a cytokine. For example a population of cells can be contacted with one or more cytokines selected from IL-15, IL-23, IL-6, IL-21 IL-18 and/or IL-2.

In a further embodiment, there is provided a method of treating an inflammatory disorder in a subject comprising administering an effective amount of a cell population in accordance with the embodiments and aspects described above to the subject. In some aspects, at least about 60, 70, 80, 90 or 95 percent of the cells are CD26 negative cells. In specific aspects, at least 96, 97, 98 or 99 percent of the cells are CD26 negative T cells. In several aspects, the cell population is essentially free of CD26 positive cells. In certain aspects, the cell population is autologous.

In further aspects, the method may additionally comprise administering at least a second therapeutic agent. In particular aspects, the at least a second therapeutic agent comprises an anti-inflammatory agent, an antiviral agent or an antibiotic. In some aspects, the cell population is administered intravenously, intraperitoneally, intratracheally, intratumorally, intramuscularly, endoscopically, intralesionally, percutaneously, subcutaneously, regionally, or by direct injection or perfusion. In certain aspects, the inflammatory disorder is an autoimmune disease. In specific aspects, the autoimmune disease comprises rheumatoid arthritis, psoriasis, type 1 diabetes, systemic lupus erythematosus (SLE), transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. In some particularly cases, there is provided methods for treating or delaying the onset of rheumatoid arthritis, type 1 diabetes or multiple sclerosis.

In still further aspects, the inflammatory disorder may be an inflammatory disorder associated with an infection. In certain aspects, the infection is a viral or bacterial infection. In certain aspects, the infection is an influenza virus, adenoviruses, reoviruses, herpes simplex virus (HSV or CMV), measles viruses, retroviruses (e.g., HIV), poxviruses (e.g. small pox), rhabdoviruses (rabies virus), picorna virus (e.g., coxsackievirus), flavivirus (e.g., West Nile virus or Zika virus) or rhinovirus infection. In further aspects, the infection is a gut infection, peripheral infection, tissue-resident infection or systemic infection. In particular aspects, the infection may be a gut infection. In some further aspects, the subject may be a human subject.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(D) Following PMA/Ionomycin stimulation, the intracellular cytokine profile was determined and the percentage of cytokine positive cells is displayed. (E) The memory phenotype of CD4+ T cells is shown. The gating strategy: Naive=CD45RA+ CCR7+ CD62L+; Tcm=CD45RO+ CCR7+ CD62L+; Tem=CD45RO+ CCR7− CD62L−; Teff=CD45RA+ CCR7− CD62L−. (F) Cells were stained for transcription factors Tbet and RORγt. Unless indicated, differences are not significant. (G) CD26$^{high}$ T cells has been described herein for the use in adoptive T cell transfer therapy. These cells are more effective at regressing tumor than classic Th1, Th2 and Th17 cells. We found that CD26$^{high}$ T cells derived from cancer patients were cytotoxic, multi-functional and possessed an inflammatory signature. CD26$^{high}$ T cells persisted to a remarkably greater extent that other CD4+ T helper cells in vivo and were able to eradicate tumors without CD8+ T cells.

Figures 9A, 9B:
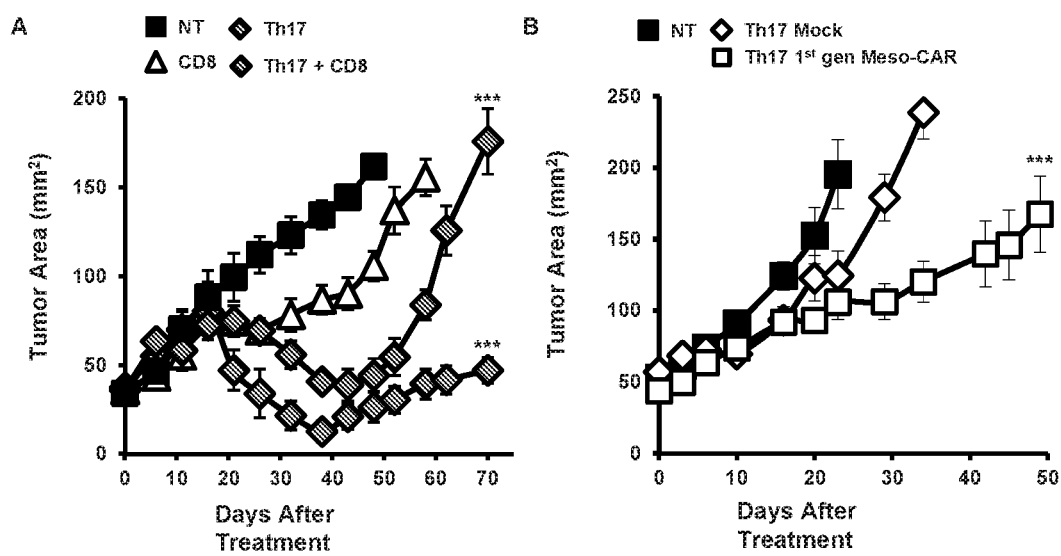

FIGS. 9A-9B: Polarized Th17 cells require a tumor-specific 2$^{nd}$ generation CAR and CD8+ T cell help for effective tumor regression. (A) Human polarized Th17 and Tc17 cells were stimulated with beads coated with αCD3/αICOS. One day later, activated T cells were genetically redirected with a 2$^{nd}$ generation mesothelin-binding CAR. Once expanded, cells were infused (2×10$^6$ transduced CD4+ Th17 cells+/−2×10$^6$ transduced CD8+ Tc17 cells) into NSG mice bearing human mesothelioma tumors (M108). Tumor areas were calculated over time and average tumor curves were shown (5 mice/group). All groups were significantly different from one another at day 40 ($P<0.001$), except CD8+Th17 vs. Th17, $P=0.09$; polynomial regression. (B) ICOS-activated, IL-17-polarized T cells were genetically redirected with either a 1$^{st}$ generation (CD3ζ signaling; no costimulation) mesothelin-specific CAR or mock engineered. Once expanded, 4×10$^6$ Th17 cells were infused into NSG mice bearing M108 tumors. (5 mice/group; NT and Mock versus 1St-gen-Meso-CAR $P<0.001$).

FIGS. 10A-10D: Human CD26$^{high}$ CD4+ T cells are polyfunctional. CD4+ lymphocytes were negatively isolated using magnetic beads from normal donor PBL and then rested ON in culture media containing IL-2. Cells were sorted as displayed in FIG. 2A. CD4+ T cell subsets were stimulated with αCD3/αICOS beads at a ratio of 1 bead:10 T cells. Cells were expanded in IL-2 (50-100 IU/ml). Ten days following activation cells were examined. (A) Dot plot representation of IL-17 and TNF-α. (B) Graphical representation of numerous normal donors demonstrating cytokine producing cells by flow cytometry. Averages from 10 normal donors. Compared to CD26$^{high}$ *, $P<0.05$; , $P<0.01$; *, $P<0.001$; ANOVA. (C) ELISA on supernatants taken on day 3 following sorted T cell subset activation. Representative experiment from 3 donors. (D) Normal donor PBL were sorted as Th17 (CCR4/CCR6), CD26$^{high}$ or left unsorted (bulk CD4) and expanded with magnetic beads coated with antibodies against CD3 and ICOS at a 1:10 bead to T cell ratio and debeaded on day 5. Cells were treated with Th17 polarizing media or not. Th17 media consisted of 10 ng/ml IL-1β, 10 ng/ml IL-6, 20 ng/ml IL-23, 5 μg/ml α-IFN-γ, 5 μg/ml α-IL-4. All cells were given 20 IU/ml rhIL-2 starting on day 2 following activation. Plots represent the percentage of cells secreting IL-17 on day 10 following activation by flow cytometry. Data compiled from independent experiments from 4 different normal donors.

FIGS. 11A-11D: Human CD26$^{high}$ T cells are profoundly cytotoxic. (A) Schematic displaying our methods of transduction. αCD3/αICOS-stimulated CD4+ T cell subsets were genetically engineered with a 1$^{st}$ generation (no co-stimulation, CD3ζ only) mesothelin-specific CAR. Following debeading and viral removal on day 6, cells were expanded for an additional 4 days, (B) Transduced cells were analyzed by flow cytometry for CAR expression prior to use. (C) Bulk CD4+ T cells, Sorted CD4+ or CD8+ CD26$^{high}$ T cells were stained for flow cytometry following sorting (day 0) for markers of MAIT cell markers Vα7.2, CD161, and MR1. (D,E) CD4+ T cells were sorted, transduced and co-cultured with target cells (mesothelin expressing-K562) overnight at various E:T ratios. (C) Percentage of K562-meso cells that were lysed by effector CD4+ T cell subsets. (D) Percentage of CD4+ T cells expressing CD107A. Representative of 3 experiments.

Figures 2A, 2B, 2C, 2D, 2E:
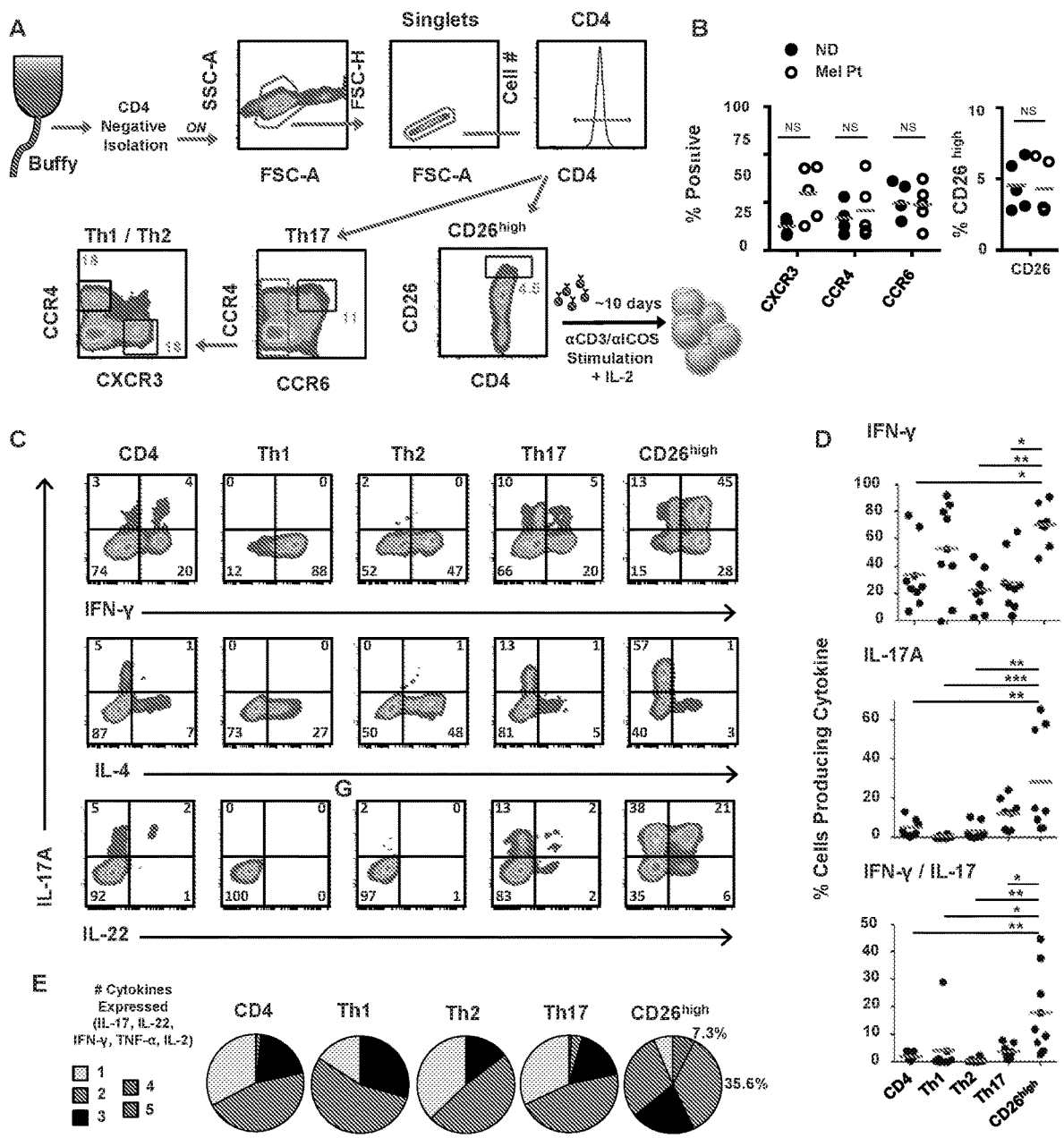
FIGS. 2A-E: $CD26^{high}$ T cells co-secrete multiple inflammatory cytokines. (A) $CD4^+$ lymphocytes were negatively isolated using magnetic beads from normal donor PBL. Th17 cells were sorted from $CCR6^+CCR4^+$ gate. Th1 and Th2 cells are both $CCR6^-$ and subsequently sorted via CXCR3 or CCR4, respectively. $CD26^{high}$ cells were sorted based on CD26 expression. $CD4^+$ T cell subsets were stimulated with αCD3/αICOS beads at a ratio of 1 bead:0.1 T cells and expanded in IL-2 (100 IU/ml). (B) PBMC from normal donor or melanoma patient buffy coats were analyzed for the expression of CD4 and chemokine receptors to delineate T cell subsets via flow cytometry. NS; t-test. (C-E) Ten days following activation, the 5 different cell subsets were examined for their intracellular cytokine production. (C) Dot plot representation of IL-17, IFN-γ, IL-4, and IL-22 expression by flow cytometry. (D) Graphical representation of numerous normal donors from independent experiments demonstrating IFN-γ and IL-17 single and double producing cells by flow cytometry. Compared to $CD26^{high}$ *, P<0.05; , P<0.01; *, P<0.001; ANOVA. (E) Cells were gated on cytokine producing cells to quantify cells that produced between one and five cytokines simultaneously. Cytokines of interest were IL-17, IFN-γ, IL-2, IL-22 and TNF-α. Representative of 5 experiments.

FIGS. 12A-12D: Enhanced homeostatic cytokine receptor expression on CD26$^{high}$ T cells. Human CD4+ lymphocytes were negatively isolated using magnetic beads from normal donor PBL and then rested ON in culture media containing IL-2. Cells were sorted as shown in FIG. 2A. (A) Cells were stimulated with αCD3/αICOS beads at a ratio of 1 bead:10 T cells and expanded in IL-2 (50-100 IU/ml). Ten days following activation cells were examined. Surface expression of memory markers measured by flow cytometry and displayed in comparison to bulk CD4+ T cells. (B) RNA was isolated from sorted T cell subsets and gene expression levels were determined by OneArray on day 0 following sorting. Heat map of log 2-fold change in expression of homeostatic cytokine receptors and memory-associated genes from 3 normal donors. (C) Th17 polarized cells were co-cultured with beads coated to stimulate either CD3/CD28 or CD3/ICOS and IL-2 or IL-15. Ten days later, cells were analyzed for cytokine production. (D) CD4+ T cell subsets were stained for surface marker expression of homeostatic cytokine receptors following sorting. MFI of expression compared to CD4+ sorted cells from 6 different donors. Compared to CD26$^{high}$ , $P<0.01$; *, $P<0.001$; ****, $P<0.0001$; ANOVA.

Figures 13A, 13B:
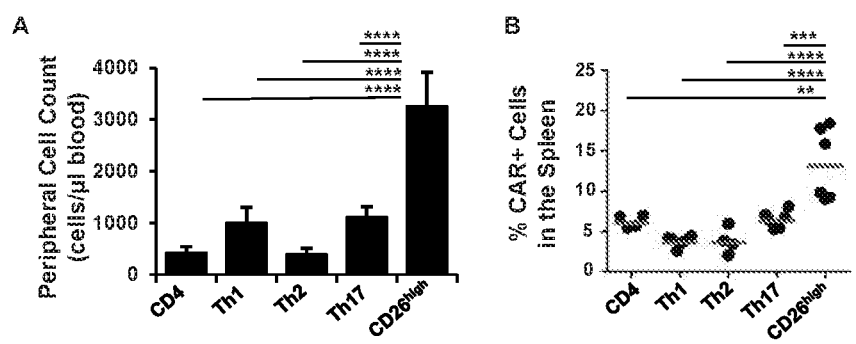

FIGS. 13A-13B: CD26$^{high}$ T cells enhance the persistence of co-infused CAR+CD8+ T cells. Sorted Th1, Th2 Th17, CD26$^{high}$, bulk CD4+ T cells and bulk CD8+ T cells were expanded with αCD3/αICOS beads and transduced with a 1$^{st}$ generation mesothelin-targeted CAR. Cells were transferred into mesothelioma bearing NSG mice as described in FIG. 3A. (A) Blood was taken at day 20 and analyzed by flow for the number of CD45+CAR+CD8+ T cells using TrueCount beads. Compared to CD26$^{high}$, all subsets were statistically different, $P<0.001$; ANOVA. (B) Spleens from mesothelioma-bearing mice were analyzed for the percentage of CD45+CAR+CD8+ T cells. Individual animals and mean (red line) are represented. Compared to CD26$^{high}$ all subsets were $P<0.01$; ANOVA.

FIGS. 14A-14G: CD26$^{high}$ T cells have a unique phenotype from classic Th1, Th2 or Th17 cells. (A) RNA was isolated from sorted T cell subsets and gene expression levels were determined by OneArray on day 0 following sorting. Heat map of log 2-fold change in expression of homeostatic cytokine receptors and memory-associated genes. Graphical representation from 3 normal donors of select transcription factors associated with T cell subsets isolated from gene array analysis. *, $P<0.05$; ANOVA. (B) Nuclear protein fractions were analyzed for transcription factor expression by Western blot. Histone 3 was used as a loading control. Representative of independent experiments from 3 separate normal donors. (C) Following CD4+ and CD8+ T cell sorting for CD26$^{high}$ cells, cells were stained for markers associated with MAIT cells and analyzed by flow cytometry. (D, E) Venn diagrams were constructed to display the area equaling the number of unique or shared TCRβ sequences. The relative frequencies (standardized to add to 1.0). (D) $CD26^{high}$ only=0.237, Th1 only=0.487, Th17 only=0.196, $CD26^{high}$ & Th1=0.041, $CD26^{high}$ & Th17=0.020, Th1 & Th17=0.015, All three=0.004. (E) $CD26^{high}$ only=0.35, Th2 only=0.28, Th17 only=0.29, $CD26^{high}$ & Th2=0.010, $CD26^{high}$ & Th17=0.029, Th2 & Th17=0.044, All three=0.005; log-linear model. (F) $CD26^{high}$ T cells have differentially expressed genes from Th17 cells. RNA was isolated from 3 normal donors' sorted T cell subsets and gene expression levels were determined by OneArray on day 0. Heat map of log 2-fold change in expression of genes with the highest or lowest expression in $CD26^{high}$ T cells. (G) Principle Component Analysis of microarray data using relevant and differentially expressed genes.

FIGS. 15A-15G: Human CAR-$CD26^{high}$ T cells express an activated phenotype in vitro and mediate potent antitumor activity in vivo. $CD4^+$ lymphocytes were isolated from healthy donor PBMC, sorted by CD26 expression and stimulated with magnetic beads coated with CD3 and ICOS agonists (cultured at a ratio of 1 bead to every 5 T cells). T cells were transduced 36 hours post-activation with a lentiviral vector encoding a $1^{st}$ generation chimeric antigen receptor that recognizes mesothelin and stimulates the CD3 domain. These cells were expanded for 10 days with IL-2 (100 IU/ml). A and B, NSG mice were subcutaneously injected with $5e^6$ M108 mesothelioma cells. Forty days post-M108 establishment, mice were intravenously infused with $1e^5$ human $CD26^{neg}$ or $CD26^{high}$ T cells redirected to express MesoCAR. Tumors were measured bi-weekly (N=10 mice/group). P values for the tumor curve were calculated using final tumor measurements from day 62. C-G, Graphical representations of transcription factors (C-F; N=10) and cytokine production (G; N=3) by sorted T cells isolated from multiple healthy individuals prior to bead stimulation. In G, the frequency of $FoxP3^+$ cells from the enriched $CD26^{neg}$ or $CD26^{high}$ cultures secreting inflammatory cytokines were assayed by flow cytometry. *, $P<0.05$; , $P<0.01$; **, $P<0.0001$.

FIGS. 16A-16E: $CD26^{int}$ T cells have a naïve phenotype while $CD26^{neg}$ and $CD26^{high}$ T cells are differentiated. A, Sorting strategy: $CD4^+$ T cells were isolated from buffy coats from healthy individuals and FACS-sorted into bulk $CD4^+$, $CD26^{neg}$ (bottom~10%), $CD26^{int}$ (middle~15%) and $CD26^{high}$ (top~10%). B and C, Memory phenotype from all subsets was determined using flow cytometry (B; N=26) and gene array analysis (C; N=3-5) prior to bead stimulation. For C, RNA was isolated and gene expression assessed by OneArray. Heat map displays (+/−) log 2-fold change in memory-associated genes. D and E, Graphical representation of co-stimulatory and co-inhibitory markers determined by flow cytometry (D; N=20-26) and gene array (E; N=3-5) prior to bead stimulation. Surface marker expression in D was calculated and graphed as a fold change of $CD26^{neg}$, $CD26^{int}$ and $CD26^{high}$ T cells compared to bulk $CD4^+$. *, $P<0.05$; , $P<0.01$; **, $P<0.0001$.

FIGS. 17A-17E: CD26 defines CD4 T cells with naïve, helper or regulatory properties. $CD4^+$ T cells were isolated from healthy donors and sorted by CD26 expression. Representative FACS plots (A) and phenotype data (B; N=26) from multiple healthy individuals. C, Heat map of (+/−) log 2-fold change in expression of $CD4^+$ subset-associated genes (N=3-5) prior to bead stimulation. D and E, Human $CD4^+$ T cells were sorted into bulk $CD4^+$, $CD26^{neg}CD26^{int}$, $CD26^{high}$, Th1 ($CXCR3^+CCR6^-$), Th2 ($CCR4^+CCR6^-$), Th17 ($CCR6^+CCR4^+$) and Th1/Th17 ($CXCR3^+CCR6^+$). DNA was isolated from sorted T cells prior to expansion of TCRβ sequences using an immunoSEQ kit and subsequent analysis. Data shown is the percent TCRβ overlap between groups (D) and a Venn diagram (E) displaying the overlap frequencies of identical TCRβ sequences between $CD26^{neg}$, $CD26^{int}$, $CD26^{high}$ and Th1/Th17 subsets (E) (N=4). *, $P<0.05$; , $P<0.01$; *, $P<0.001$; ****, $P<0.0001$.

FIGS. 18A-18E: $CD26^{high}$ T cells are multifunctional and enzymatically active. $CD4^+$ T cells from healthy individuals were isolated and sorted by CD26 expression (FIG. 2A). A and B, Sorted T cells were activated with PMA/Ionomycin and Monensin for four hours prior to intracellular staining (N=26). In B, three independent donors were analyzed by FlowJo software and graphed to display the percentage of cells simultaneously secreting 1-5 cytokines (IL-2, IFNγ, TNFα, IL-17A, IL-22). C, Supernatant was collected from cells at pre-activation (0) and 1, 6 and 12 days post-activation time points for ELISA (N=2). D, T cells activated in vitro were subjected to intracellular staining (N=5-11). E, $1e^5$ sorted cells per group from pre-activation (0) and 10 days post-activation were cultured with the CD26 ligand gly-pro-P-nitroanalide for two hours at 37° C. and analyzed for colorimetric changes to determine enzymatic activity (N=5). *, $P<0.05$; , $P<0.01$; *, $P<0.001$; ****, $P<0.0001$.

FIGS. 19A-19I: $CD26^{int}$ and $CD26^{high}$ T cells regress human mesothelioma and pancreatic tumors. $CD4^+$ T cells were isolated from healthy individuals, sorted by CD26 expression, transduced to express MesoCAR and expanded for 10 days. A and B, NSG mice bearing large M108 mesothelioma tumor (established for 60 days) were infused with $1e^6$ human $CD4^+$, $CD26^{neg}$, $CD26^{int}$ or $CD26^{high}$ T cells. Post-ACT, tumors were measured bi-weekly until mice were sacrificed and organs harvested at 75 days post-ACT (N=7-9 mice/group). P values for the tumor curve were calculated on the final day when mice from all comparison groups were still alive (NT vs. all groups=day 38; $CD26^{neg}$ vs. $CD26^{high}$=day 59). C, Percent change in tumor size from baseline (day 0) to endpoint (day 75) was calculated and graphed as a Waterfall plot. D, Graphical representation of tumor weights (g) harvested from treated mice 75 days post-ACT. E and F, NSG mice bearing established pancreatic tumors (PANC1) were infused with $1.75e^6$ human $CD4^+$, $CD26^{neg}$, $CD26^{int}$ and $CD26^{high}$ T cells and tumors were measured bi-weekly for more than three months (N=6-9 mice/group). P values for the tumor curve were calculated on the final day when mice from all comparison groups were still alive (All groups=day 84). G, Graphical representation of tumor weight (g) harvested from mice 97 days post-ACT. H-I, Tumors from all treated mice were harvested, digested and run through a strainer. Resulting cell suspension was stained for flow cytometry and graphed relative to tumor size (small<100 $mm^2$, medium=100-200 $mm^2$, large>200 $mm^2$). , $P<0.01$; *, $P<0.001$.

FIGS. 20A-20J: $CD26^{high}$ T cells have stemness and increased migratory capacity. A and B, Tumors from treated PANC1-bearing mice (from FIG. 5) were harvested and then frozen in cryomatrix. Tumor samples were then sliced and used for immunohistochemistry analysis (purple=H&E, brown=CD45; N=5-9 tumors/group). Magnification=10×. In B, the density of CD45 (IOD) in CD26-sorted groups was quantified with Image J software and graphed (N=5-8/group). C, Sorted T cells were activated with CD3/ICOS beads and expanded in 100 IU/ml IL-2 for ten days prior to testing cell migration via a transwell assay. $0.75e^6$ sorted cells were re-suspended and assessed for percent cell migration towards M108 or PANC1 supernatant in a two hour time period (N=5). D and E, Sorted T cells were analyzed for chemokine receptor expression by flow cytometry (D;

N=12-15) and gene array (E; N=3-5) prior to bead stimulation. In E, data shown in heat map as (+/−) log 2-fold change in chemokine receptor expression compared to bulk CD4+. F, Viability of T cells that migrated towards PANC1 was determined by Live/Dead staining (N=3). G, Anti-apoptotic and stemness genes were analyzed and displayed as a (+/−) log 2-fold change compared to bulk CD4+ (N=3-5). H-J, Protein from pre-activation (day 0) and post-activation (day 10) cells was isolated and used for western blot analysis (N=2-3). In J, the fold change of β-catenin, BCL2 and cleaved Caspase 3 for each subset compared to bulk CD4+ T cells was graphed (N=2-3) *, P<0.05; , P<0.01; **, P<0.0001.

Figure 21:
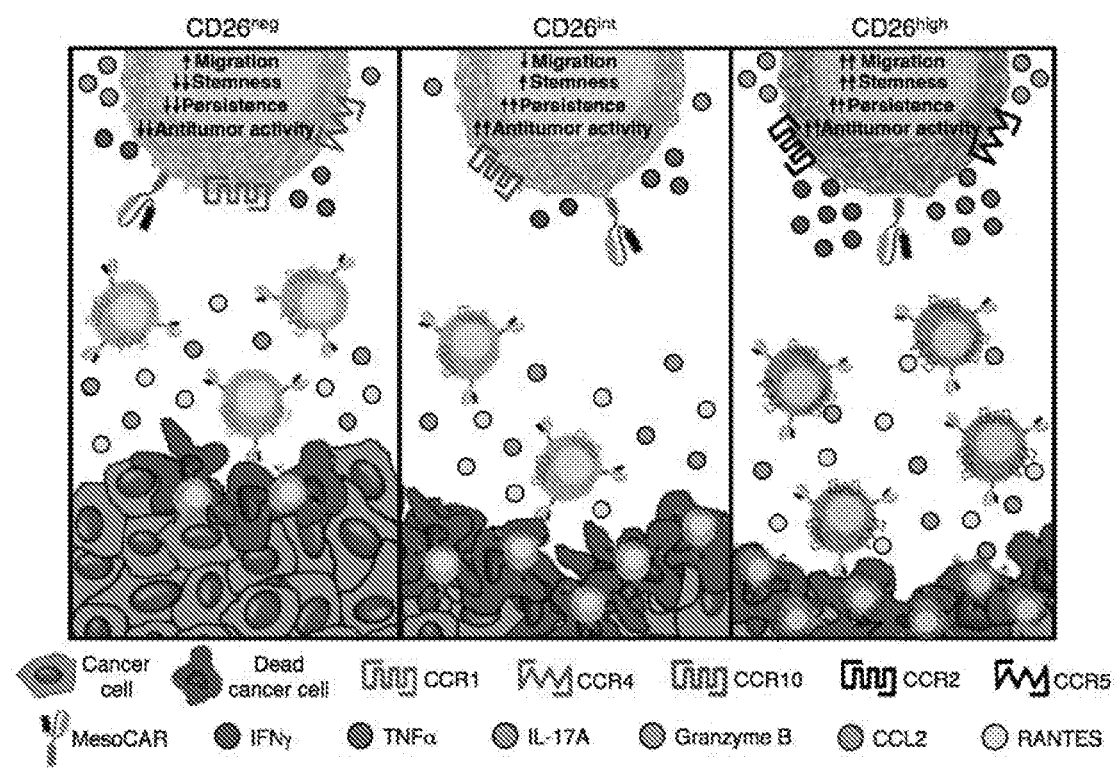

FIG. 21: CD26 identifies three CD4+ T cell subsets with distinct biological properties. Depiction of observations on CD26 expression and cellular therapy described herein. CD26$^{neg}$ T cells, despite their enhanced capacity to migrate, fail to regress tumors due to regulatory properties, decreased persistence and increased sensitivity to cell death. CD26$^{int}$ and CD26$^{high}$ T cells exhibit similar antitumor activity, but have vastly different immunological properties. Despite their decreased migration, CD26$^{int}$ T cells are naïve and capable of persisting long-term. CD26$^{high}$ T cells, despite their differentiated phenotype, exhibit several anti-apoptotic and stemness features, persist long-term, co-secrete multiple cytokines and cytotoxic molecules and have a natural capacity to migrate towards various established solid tumors.

FIGS. 22A-22G: Murine CD26high T cells regress melanoma to a greater extent than CD26neg T cells. Splenocytes from transgenic TRP-1 mice were isolated and cultured with 1 μl/ml TRP-1 peptide and feeder cells at a ratio of 1 feeder:5 TRP-1 cells. TRP-1 CD4+ T cells were programmed to a Th17 phenotype using polarizing cytokines (10 ng/ml hIL-1β, 100 ng/ml hIL-21, 100 ng/ml hIL-6, 30 ng/ml hTGFβ, 10 μg/ml αm-IFNγ, 10 μg/ml αm-IL-4) and expanded with 100 IU/ml IL-2. After six days expansion, Vβ14+CD4+ Th17 cells were sorted by CD26 into CD26neg (bottom~10%) and CD26high (top~5%). (A-C) B6 mice bearing B16F10 melanoma established for 10 days were infused with 5e4 CD4+Vβ14+ CD26neg or CD26high T cells. All mice were lymphodepleted with 5 Gy total body irradiation one day prior to ACT (N=6 mice/group, representative of two individual experiments). P values for the tumor curve were calculated on the last day that all mice from compared groups were alive (NT vs. CD26high=day 9, CD26neg vs. CD26high=day 21). (D) Representative histograms of human CD26neg and CD26high T cells after being sorted for MesoCAR expression, yielding~98% pure population (E-G) Representative FACS plots of transcription factors (E) and activation markers (F) from sorted human T cells prior to bead stimulation (N=6). (G) Summary activation marker data from six individual donors. *, P<0.05; **, P<0.01.

Figures 23A, 23B, 23C:
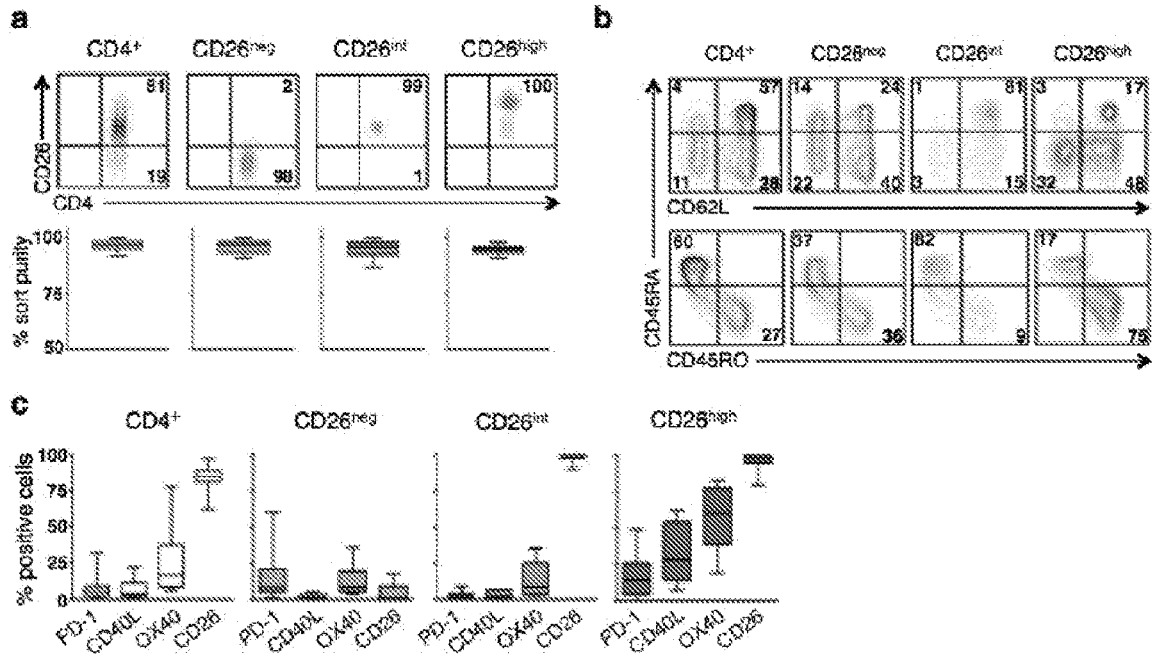

FIGS. 23A-23C: CD26-sorted subsets are pure and have unique profiles. Human CD4+ T cells from healthy donors were sorted by CD26 expression. (A) Post-sort phenotype (top, representative of 26 donors) and purity (bottom, N=26) of all sorted subsets was determined using flow cytometry. (B, C) Representative FACS plots of memory (B; N=26) and graphical representation of co-stimulatory/co-inhibitory markers (C; N=8-12) by flow cytometry prior to cell activation.

FIGS. 24A-24E: TCRβ sequences of CD26high T cells overlap with Th1/Th17 cells, but not Th2. (A) Human CD4+ T cells were sorted by CD26 and analyzed for CCR6 and CD161 expression by flow cytometry (representative of 26 donors). Human CD4+ T cells were sorted into bulk CD4+, CD26neg, CD26int, CD26high, Th1 (CXCR3+CCR6−), Th2 (CCR4+CCR6−), Th17 (CCR6+CCR4+) and Th1/Th17 (CXCR3+CCR6+). DNA was isolated from sorted subsets and TCRβ sequencing was performed using an immunoSEQ kit and subsequent analysis. (B) Graphical representations of TCR overlap between Th1 cells and CD26high or CD26neg (N=4). (C) Correlation of TCR expression (r2) determined and graphed using a heatmap diagram (N=4). (D, E) TCR overlap between Th1/Th17 and CD26high (D) and CD26high compared to CD26neg, CD26int and Th1/Th17 cells (E) was defined via immunoSEQ software (N=4). *, P<0.05.

FIGS. 25A-25F: CD26high T cells are highly functional and cytotoxic. CD4+ T cells from the blood of healthy individuals were sorted by CD26 expression. (A-E) Sorted cells were activated with PMA/Ionomycin and Monensin for 4 hours prior to intracellular staining (N=5-26). In (D), three independent donors were analyzed by FlowJo software and graphed to display the percentage of cells simultaneously secreting 0-5 cytokines (IL-2, IFNγ, TNFα, IL-17A, IL-22). (F) 1e5 sorted cells were incubated with the CD26 ligand gly-pro-P-nitroanalide at 37° C. for 2 hours and enzyme activity was determined using a colorimetric assay (N=5). *, P<0.05; , P<0.01; *, P<0.001; ****, P<0.0001.

FIGS. 26A-26J: CD26-sorted subsets in patients with metastatic melanoma have a similar functional and phenotypic profile as those enriched from healthy donors. The biologic properties of CD26neg, CD26int and CD26neg T cells from the blood of patients with metastatic melanoma were analyzed via flow cytometry (N=5). (A) Representative FACS plot of CD26 expression on CD4+ T cells. (B) Graphical representation of CD26 MFI on sorted T cells from cancer patients (N=5) and healthy individuals (N=5). (C-J) Scatter plots of sorted T cells from melanoma patients analyzed by flow cytometry. Intracellular stains were performed following activation with PMA/Ionomycin and Monensin for four hours (N=5). *, P<0.05; , P<0.01; *, P<0.001; ****, P<0.0001.

FIGS. 27A-27G: CD26int and CD26high T cells regress multiple tumors. CD4+ lymphocytes from healthy donors were sorted by CD26 expression and stimulated with CD3/ICOS beads (1 bead: 5 T cells). Cells were transduced at 36 hours post activation to express a 1st generation mesothelin-specific CD3ζ CAR and expanded in IL-2 (100 IU/ml) for 10 days. (A) MesoCAR transduction efficiency was determined using flow cytometry prior to ACT. (B) Individual tumor curves for each treatment group compared to no treatment (black lines) for M108-bearing NSG mice discussed (N=7-9 mice/group). P values for tumor curves were calculated on the final day when mice from all comparison groups were still alive (NT vs. all groups=day 38). (C) NSG mice bearing either mesothelioma or pancreatic cancer were infused with 12.5e6 nonspecific mock T cells or 12.5e6 transduced T cells (~40% MesoCAR+) on days 49 (PANC1) or 75 (M108) post-tumor inoculation. (D) MesoCAR transduction efficiency of sorted T cell subsets was determined by flow cytometry prior to ACT into PANC1-bearing mice. (E) Individual tumor curves for each treatment group compared to no treatment (black lines) for NSG mice with pancreatic cancer (6-9 mice/group). P values for tumor curves were calculated on the final day when mice from all comparison groups were still alive (All groups=day 84). (F) Percent tumor change calculated using baseline (day 0) and final (day 97) tumor measurements; graphed as a Waterfall plot. (G) Tumors from all treated mice were harvested, digested and run through a strainer. Resulting cell suspension was stained for flow cytometry and graphed relative to tumor size. *, P<0.05; , P<0.01; *, P<0.001.

FIGS. 28A-28F: Stem memory CD26high T cells persist and migrate to the tumor. (A) Tumors from PANC1-bearing mice were harvested and the percentage of CD45+ T cells was determined by flow cytometry (N=7-9). (B) 7.5e4 bulk CD4+, CD26neg, CD26int and CD26high T cells were assayed for migration towards control media (top) and media supplemented with 10% FBS (bottom) using a transwell assay (N=5). (C) Expression of migration-related genes in pre-activated, sorted T cells was determined via gene array and graphed as a (+/−) log 2-fold change (N=3-5). (D) Chemokine receptor expression on inactivated, sorted T cells was assessed via flow cytometry (N=15). (E) Ten-day expanded T cells were analyzed for apoptosis using Annexin V/PI staining in the presence or absence of overnight activation with anti-CD3 antibody (N=6). (F) Lef1 expression in sorted T cell subsets was determined by qPCR analysis (N=4-5). *, P<0.05; , P<0.01; *, P<0.001; ****, P<0.0001.

FIG. 29: List of flow cytometry antibodies.

Figures 30A, 30B:
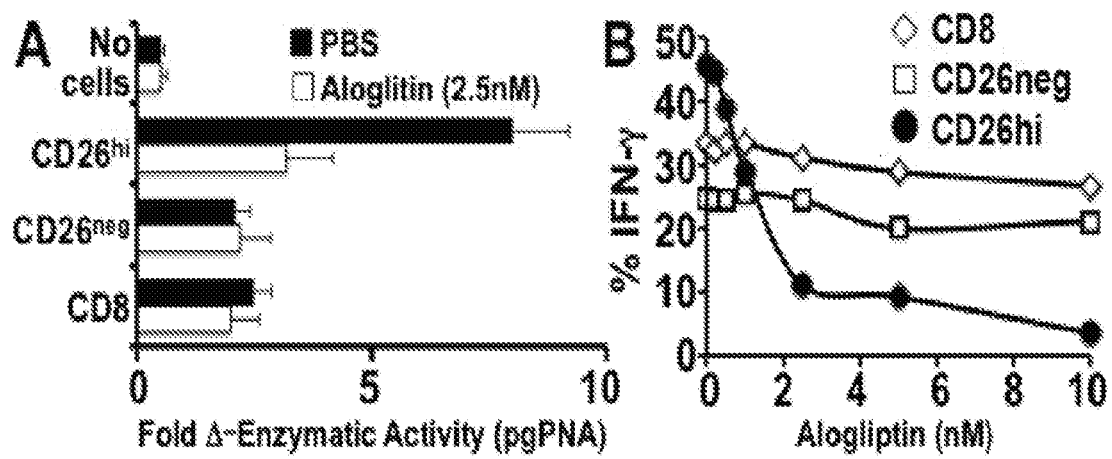

FIGS. 30A-30B: Enzymatic properties of $CD26^{high}CD4^+$ T cells. (A) $CD26^{high}CD4^+$ T cells and $CD26^{neg}CD4^+$ T cells were treated with Alogliptin (2.4 nm), CD3/ICOS bead activated and expanded for 10 days. Enzymatic activity was measured by fold change in pgPNA by ELISA. (B) IFNγ secretion by subsets treated with increasing Alogliptin doses after antigen-specific stimulation.

FIGS. 31A-31D: Alogliptin reduces $CD4^+CD26^{high}$ cell function. PBMCs were sorted by CD26 expression, expanded 10d & PMA/Iono activated (A). 2.5 nM Alogliptin-treated $CD26^{high}$ T cells (gray) secreted less cytokines (B), cytotoxins (C) and chemokines (D) than $CD4^+CD26^{high}$ T cells (black). N=4

FIGS. 32A-32J: (A) Peripheral blood mononuclear cells (PBMC) and $CD4^+$ T cells were sorted for their expression of CD26 by flow cytometry, CD3/ICOS bead activated and expanded for 10 days with IL-2. (B) Growth of total PBMC, PBMC positive for CD26, PBMC with high CD26, and $CD4+CD26^{high}$ T cells over the 10 days as well as the ratio of $CD4^+:CD8^+$ cells. (C) Phenotype of PBMC cells after 10 days of expansion. (D) Percent expression of CCR7, CD62L, CCR4, CCR6/CD161, and CCR6/CXCR3 positive cells in each subset. (E) Percent expression of CD28, CD150, CD146, and OX40 in each subset. (F) Percent expression of CD62L, CD28, Va7.2, CD146, and CD25/CD127 in PBMC subsets. (G) $CD4^+$ and $CD8^+$ cells in each subset over 10 days. (H-I) Percent expression of IFNγ, IL-17, IL-22, IL17/IFNγ, and IL-17/IL-22 in each subset. (J) Percent expression of granzyme B, perforin, and TNFα in each subset.

DESCRIPTION OF ILLUSTRATIVE EMBODIMENTS

The present disclosure overcomes challenges associated with current technologies by providing methods for the production and use of $CD26^{high}$ T cells. This novel, human T cell or other immune cell population is inducible by ICOS costimulation and likely other activating signals, which expresses high levels of CD26 (a costimulatory molecule with enzymatic properties) on their cell surface—termed $CD26^{high}$ T cells herein. The $CD26^{high}$ T cells simultaneously secrete elevated IL-17A, IFN-γ and IL-22 compared to Th1, Th2 or Th17 cells. When infused into mice bearing human tumors, $CD26^{high}$ T cells more efficiently reconstituted immunodeficient hosts and persisted long-term compared to other subsets. Remarkably, $CD26^{high}$T cells engineered with a $1^{st}$ generation CD3ζ mesothelin-specific chimeric antigen receptor (CAR) were capable of ablating large human mesothelioma tumors when infused into mice. Treatment with CAR-engineered Th1, Th2 or Th17 cells was less effective than treatment with $CD26^{high}$ T cells. This finding is surprising given that $1^{st}$ generation CARs (consisting of either the cytoplasmic domain of the Fc receptor γ chain or CD3ζ signaling modules alone) historically do not elicit robust antitumor effects in preclinical or clinical trials, when compared to $2^{nd}$ generation CARs with the addition of a co-stimulatory domain[4,5]. In contrast to work by Albert et al. showing that CD26 impairs $CD8^+$ T cell persistence within the tumor and thus dampens antitumor immunity, the present disclosure shows that human $CD26^{high}$ T cells enhanced the persistence and polyfunctionality of co-infused tumor-specific $CD8^+$ T cells. Interestingly, $CD26^{high}$, but not Th17 cells, were capable of clearing tumor in NSG mice without cytolytic assistance from $CD8^+$ T cells. Additional investigation revealed that inherent therapeutic effectiveness of $CD26^{high}$ T cells was likely due to their robust cytotoxic potential and distinct inflammatory signature. Further, the enzymatic activity of CD26 may have a role on the function, migration and cytotoxicity of $CD4^+CD26^{high}$ T cells in the tumor microenvironment. Thus, the enzymatic activity of these cells may be used to further enhance the efficacy of ACT treatment (i.e., enzymatic stimulation via exogenous chemokines). Accordingly, the present disclosure provides a new human T cell subset with remarkable antitumor properties which can be harnessed to design next generation cancer immunotherapies for the clinic.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a $CD26^{high}$T cell or other immune cell therapy.

"Subject" and "patient" refer to either a human or non-human, such as primates, mammals, and vertebrates. In particular embodiments, the subject is a human.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 μg/kg/body weight to about 1000 mg/kg/body weight (this such range includes intervening doses) or more per administration, and any range derivable therein. In non-limiting examples of a derivable range from the numbers listed herein, a range of about 5 μg/kg/body weight to about 100 mg/kg/body weight, about 5 μg/kg/body weight to about 500 mg/kg/body weight, etc., can be administered. The practitioner responsible for administration will, in any event, determine the concentration of active ingredient(s) in a composition and appropriate dose(s) for the individual subject.

The term "immune checkpoint" refers to a molecule such as a protein in the immune system which provides inhibitory signals to its components in order to balance immune reactions. Known immune checkpoint proteins comprise CTLA-4, PD1 and its ligands PD-L1 and PD-L2 and in addition LAG-3, BTLA, B7H3, B7H4, TIM3, KIR or any other immune receptor that inhibits the proliferation and activation of immune cells. The pathways involving LAG3, BTLA, B7H3, B7H4, TIM3, and KIR are recognized in the art to constitute immune checkpoint pathways similar to the CTLA-4 and PD-1 dependent pathways (see e.g. Pardoll, 2012; Mellman et al., 2011).

An "immune checkpoint inhibitor" refers to any compound inhibiting the function of an immune checkpoint protein. Inhibition includes reduction of function and full blockade. In particular the immune checkpoint protein is a human immune checkpoint protein. Thus the immune checkpoint protein inhibitor in particular is an inhibitor of a human immune checkpoint protein.

"Long-term engraftment" is defined herein as the stable transplantation of cells such as the activated $CD26^{high}$ cells provided by the methods herein into a recipient such that the transplanted cells persist in the host blood and/or bone marrow more than 10 weeks, preferably more than 20 weeks. In addition, long-term engraftment can be characterized by the persistence of transplantation cells in serially transplanted mice.

The term "$CD26^{high}$ T cells" refers to a population of T cells or other immune cells which are positive for the cell surface marker CD26. In certain aspects, the $CD26^{high}$ T cells are CD4+ T cells and have an expression of CD26 in the top 50th percentile of the total CD4+ T cells from which they are isolated. In particular aspects, the $CD26^{high}$ CD4+ T cells have an expression of CD26 in the top 60, 70, 80, 90, 95, 96, 97, 98, 99 or 100th percentile of the total CD4+ T cells from which they are isolated. The term "activated $CD26^{high}$ T cells" refers to $CD26^{high}$ T cells which have been stimulated by an activation factor (e.g., ICOS) to increase the cytotoxic ability of the cells.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD26, CD27, CD28, CD137, DAP10, ICOS, 41BB, OX40 and or any other molecule. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, the term "antigen" is a molecule capable of being bound by an antibody or T-cell receptor. An antigen may generally be used to induce a humoral immune response and/or a cellular immune response leading to the production of B and/or T lymphocytes.

The terms "tumor-associated antigen," "tumor antigen" and "cancer cell antigen" are used interchangeably herein. In each case, the terms refer to proteins, glycoproteins or carbohydrates that are specifically or preferentially expressed by cancer cells.

II. $CD26^{high}$ T CELLS

Embodiments of the present disclosure concern obtaining and administering activated $CD26^{high}$ T cells to a subject as an immunotherapy to target cancer cells. Several basic approaches for the derivation, activation and expansion of functional anti-tumor effector T cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods of the present disclosure.

A. T Cell Preparation

In some embodiments, the $CD26^{high}$ T cells are derived from the blood, bone marrow, lymph, or lymphoid organs. In some aspects, the cells are human cells. In certain embodiments, $CD26^{high}$ T cells are derived from human peripheral blood mononuclear cells (PBMC), unstimulated leukapheresis products (PBSC), human embryonic stem cells (hESCs), induced pluripotent stem cells (iPSCs), bone marrow, or umbilical cord blood by methods well known in the art. The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4+ and/or CD8+ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells, Innate lymphocyte cells or other immune cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells). In one embodiment, the cells (e.g., CD8+ cells or CD3+ cells) are enriched for (i.e., positively selected for) cells that are positive or expressing high surface levels of CD45RO, CCR7, CD28, CD27, CD44, CD127, and/or CD62L and/or depleted of (e.g., negatively selected for) cells that are positive for or express high surface levels of CD45RA. In some embodiments, cells are enriched for or depleted of cells positive or expressing high surface levels of CD122, CD95, CD25, CD27, any other immune markers and/or IL7-Ra (CD127). In some examples, CD8$^+$ T cells are enriched for cells positive for CD45RO (or negative for CD45RA) and for CD62L.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations. In particular aspects, the CD26$^{high}$ T cells are sorted from the CD4$^+$ T cells by methods known in the art, such as fluorescence assisted cell sorting (FACS).

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakuraet et al., 2012; Wang et al., 2012. In some embodiments, combining $T_{CM}$-enriched CD8$^+$ T cells and CD4$^+$ T cells further enhances efficacy.

In some embodiments, the CD26$^{high}$ T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days, preferably about 14 days. More preferably, rapid expansion provides an increase of at least about 200-fold (e.g., 200-, 300-, 400-, 500-, 600-, 700-, 800-, 900-, or greater) over a period of about 10 to about 14 days, preferably about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be re-stimulated with irradiated, autologous lymphocytes or with irradiated HLA-A2+ allogeneic lymphocytes and IL-2, for example.

In particular aspects, the CD26$^{high}$ are activated by costimulation with inducible coactivator (ICOS). In some aspects, the ICOS stimulation is performed by culturing the CD26$^{high}$ cells with beads, such as magnetic beads, coated with anti-ICOS with or without anti-CD3 beads. The cell expansion can be performed in the presence cytokines, such as IL-2. The ratio of beads to T cells may be in the range of 1:1 to 1:50, such as 1:5 to 1:25, particularly such as 1:10.

The autologous T-cells can be modified to express a T-cell growth factor that promotes the growth and activation of the autologous T-cells. Suitable T-cell growth factors include, for example, interleukin (IL)-2, IL-7, IL-15, IL-12 and or other cytokines or small molecule drugs (such as PI3 kinase or AKT inhibitors, etc.). Suitable methods of modification are known in the art. See, for instance, Sambrook et al., 2001 and Ausubel et al., 1994. In particular aspects, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

B. Genetically Engineered Antigen Receptors

The CD26$^{high}$ T cells can be genetically engineered to express antigen receptors such as engineered TCRs and/or chimeric antigen receptors (CARs). For example, the autologous CD26$^{high}$ T-cells are modified to express a T cell receptor (TCR) having antigenic specificity for a cancer antigen. Suitable TCRs include, for example, those with antigenic specificity for a mesothelin antigen. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al., 2008 and Johnson et al., 2009.

In some embodiments, the CD26$^{high}$ T cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., Curr. Opin. Immunol., 2012; Wu et al., 2012. In some aspects, the genetically engineered antigen receptors include a CAR as described in U.S. Pat. No. 7,446,190, and those described in International Patent Application Publication No.: WO/2014055668 A1.

In some aspects, the tumor antigen is a human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (Dl). For example, the target antigen is hTERT or survivin. In some aspects, the target antigen is CD38. In other aspects, the target antigen is CD33 or TIM-3. In other aspects, it is CD26, CD30, CD53, CD92, CD148, CD150, CD200, CD261, CD262, or CD362. In some embodiments, the engineered immune cells can contain an antigen that targets one or more other antigens. In some embodiments, the one or more other antigens is a tumor antigen or cancer marker. Other antigens include orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gplOO, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD 123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens. In particular aspects, the tumor antigen is mesothelin.

1. Chimeric Antigen Receptors

In certain embodiments, the $CD26^{high}$ T cells are genetically modified to express a chimeric antigen receptor. In some embodiments, the chimeric antigen receptor comprises: a) an intracellular signaling domain, b) a transmembrane domain, and c) an extracellular domain comprising an antigen binding region.

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb). The antigen binding regions or domain can comprise a fragment of the VH and VL chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD 154 or any other molecule. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

The CAR generally includes at least one intracellular signaling component or components. In some embodiments, the CAR includes an intracellular component of the TCR complex, such as a TCR CD3+ chain that mediates T-cell activation and cytotoxicity, e.g., CD3 zeta chain. Thus, in some aspects, the antigen binding molecule is linked to one or more cell signaling modules. In some embodiments, cell signaling modules include CD3 transmembrane domain, CD3 intracellular signaling domains, and/or other CD transmembrane domains. In some embodiments, the CAR further includes a portion of one or more additional molecules such as Fc receptor γ, CD8, CD4, CD25, or CD16. For example, in some aspects, the CAR includes a chimeric molecule between CD3-zeta (CD3-ζ or Fc receptor γ and CD8, CD4, CD25 or CD16. In specific embodiments, intracellular receptor signaling domains in the CAR include those of the T-cell antigen receptor complex, such as the zeta chain of CD3, also Fcγ RIII costimulatory signaling domains, CD28, CD27, DAP10, CD137, OX40, CD2, alone or in a series with CD3zeta, for example. In specific embodiments, the intracellular domain (which may be referred to as the cytoplasmic domain) comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, one employs any part of the endogenous T-cell receptor complex in the intracellular domain. One or multiple cytoplasmic domains may be employed, as so-called third generation CARs have at least two or three signaling domains fused together for additive or synergistic effect, for example.

It is contemplated that the chimeric construct can be introduced into CD26$^{high}$ T cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into CD26$^{high}$ T cells. Suitable vectors for use in accordance with the method of the present invention are non-replicating in the CD26$^{high}$ T cells. A large number of vectors are known that are based on viruses, where the copy number of the virus maintained in the cell is low enough to maintain the viability of the cell, such as, for example, vectors based on HIV, SV40, EBV, HSV, or BPV.

2. T Cell Receptor (TCR)

In some embodiments, the genetically engineered antigen receptors include recombinant T cell receptors (TCRs) and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; see also Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., α-chain, β-chain) can contain two immunoglobulin domains, a variable domain (e.g., $V_a$ or Vβ; typically amino acids 1 to 116 based on Kabat numbering Kabat et al., 1991) at the N-terminus, and one constant domain (e.g., α-chain constant domain or $C_a$, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3y chain, a CD3δ chain, two CD3ε chains, and a homodimer of CD3ζ chains. The CD3y, CD3δ, and CD3ε chains are highly related cell surface proteins of the immunoglobulin superfamily containing a single immunoglobulin domain. The transmembrane regions of the CD3y, CD3δ, and CD3ε chains are negatively charged, which is a characteristic that allows these chains to associate with the positively charged T cell receptor chains. The intracellular tails of the CD3y, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. [0140] In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005. In some embodiments, phage display is used to isolate TCRs against a target antigen (see, e.g., Varela-Rohena et al., 2008 and Li, 2005. In some embodiments, the TCR or antigen-binding portion thereof can be synthetically generated from knowledge of the sequence of the TCR.

3. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, aAPCs are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009.

aAPC systems may comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD86, CD64 (FcγRI), 41BB ligand, and IL-21. Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), which promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

In some embodiments, the presently disclosed process can be used to genetically modify $CD26^{high}$ T cells derived from peripheral blood and/or umbilical cord blood to express CAR(s) that can be numerically expanded in vitro using aAPC (Singh et al., 2008; Singh et al., 2011; Shah et al., 2013). The process has implications for cell and gene therapy, due to the relative ease of DNA plasmid production, electroporation, use of thawed γ-irradiated master-bank aAPC, and can be readily transferred to facilities operating in compliance with current good manufacturing practice (cGMP) for clinical trials.

In one embodiment, aAPCs are also subjected to a freeze-thaw cycle. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

III. METHODS OF TREATMENT

Provided herein are methods for treating or delaying progression of cancer in an individual comprising administering to the individual an effective amount an activated $CD26^{high}$ T cell therapy. Examples of cancers contemplated for treatment include lung cancer, head and neck cancer, breast cancer, pancreatic cancer, prostate cancer, renal cancer, bone cancer, testicular cancer, cervical cancer, gastrointestinal cancer, lymphomas, pre-neoplastic lesions in the lung, colon cancer, melanoma, and bladder cancer.

In some embodiments, the individual has cancer that is resistant (has been demonstrated to be resistant) to one or more anti-cancer therapies. In some embodiments, resistance to anti-cancer therapy includes recurrence of cancer or refractory cancer. Recurrence may refer to the reappearance of cancer, in the original site or a new site, after treatment. In some embodiments, resistance to anti-cancer therapy includes progression of the cancer during treatment with the anti-cancer therapy. In some embodiments, the cancer is at early stage or at late stage.

In some embodiments of the methods of the present disclosure, activated CD4 and/or CD8 T cells in the individual are characterized by γ-IFN producing CD4 and/or CD8 T cells and/or enhanced cytolytic activity relative to prior to the administration of the combination. γ-IFN may be measured by any means known in the art, including, e.g., intracellular cytokine staining (ICS) involving cell fixation, permeabilization, and staining with an antibody against γ-IFN. Cytolytic activity may be measured by any means known in the art, e.g., using a cell killing assay with mixed effector and target cells.

In some aspects, the $CD26^{high}$ T cells are administered in combination with at least one additional anti-cancer therapy. The $CD26^{high}$ T cell therapy may be administered before, during, after, or in various combinations relative to an anti-cancer agent. The administrations may be in intervals ranging from concurrently to minutes to days to weeks. In embodiments where the T cell therapy is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the $CD26^{high}$ T therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In some embodiments, the subject can be administered nonmyeloablative lymphodepleting chemotherapy prior to the $CD26^{high}$ T cell therapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. An exemplary route of administering cyclophosphamide and fludarabine is intravenously. Likewise, any suitable dose of cyclophosphamide and fludarabine can be administered. In particular aspects, around 60 mg/kg of cyclophosphamide is administered for two days after which around 25 mg/m² fludarabine is administered for five days.

In certain embodiments, a T-cell growth factor that promotes the growth and activation of the autologous T cells is administered to the subject either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

The $CD26^{high}$ T cell therapy and anti-cancer agent may be administered by the same route of administration or by different routes of administration. In some embodiments, the T cell therapy and/or anti-cancer agent is administered intravenously, intramuscularly, subcutaneously, topically, orally, transdermally, intraperitoneally, intraorbitally, by implantation, by inhalation, intrathecally, intraventricularly, or intranasally. An effective amount of the $CD26^{high}$ T cell therapy and anti-cancer agent may be administered for prevention or treatment of disease. The appropriate dosage of the $CD26^{high}$ T cell therapy and anti-cancer agent be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (in particular 3 ml). Multiple injections delivered as single dose comprise about 0.1 to about 0.5 ml volumes.

A. Pharmaceutical Compositions

Also provided herein are pharmaceutical compositions and formulations comprising the activated $CD26^{high}$ T cell therapy, optionally an anti-cancer agent and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 22nd edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

B. Anti-Cancer Therapy

In certain embodiments, the compositions and methods of the present embodiments involve an activated $CD26^{high}$ T cell therapy in combination with at least additional anti-cancer agent. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may another subset of T cells, such as $CD8^+$ T cells. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a $CD26^{high}$ T cell therapy is "A" and an anti-cancer therapy is "B":

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT- 11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen (Carter et al., 2008; Teicher 2014; Leal et al., 2014). Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach (Teicher 2009) and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present invention. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WOO 1/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

An article of manufacture or a kit is provided comprising activated CD26$^{high}$ T cells is also provided herein. The article of manufacture or kit can further comprise a package insert comprising instructions for using the CD26$^{high}$ T cells to treat or delay progression of cancer in an individual or to enhance immune function of an individual having cancer. Any of the CD26$^{high}$ T cells described herein may be included in the article of manufacture or kits. In some embodiments, the CD26$^{high}$ T cells are in the same container or separate containers. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figures 1A, 1B, 1C, 1D, 1E:
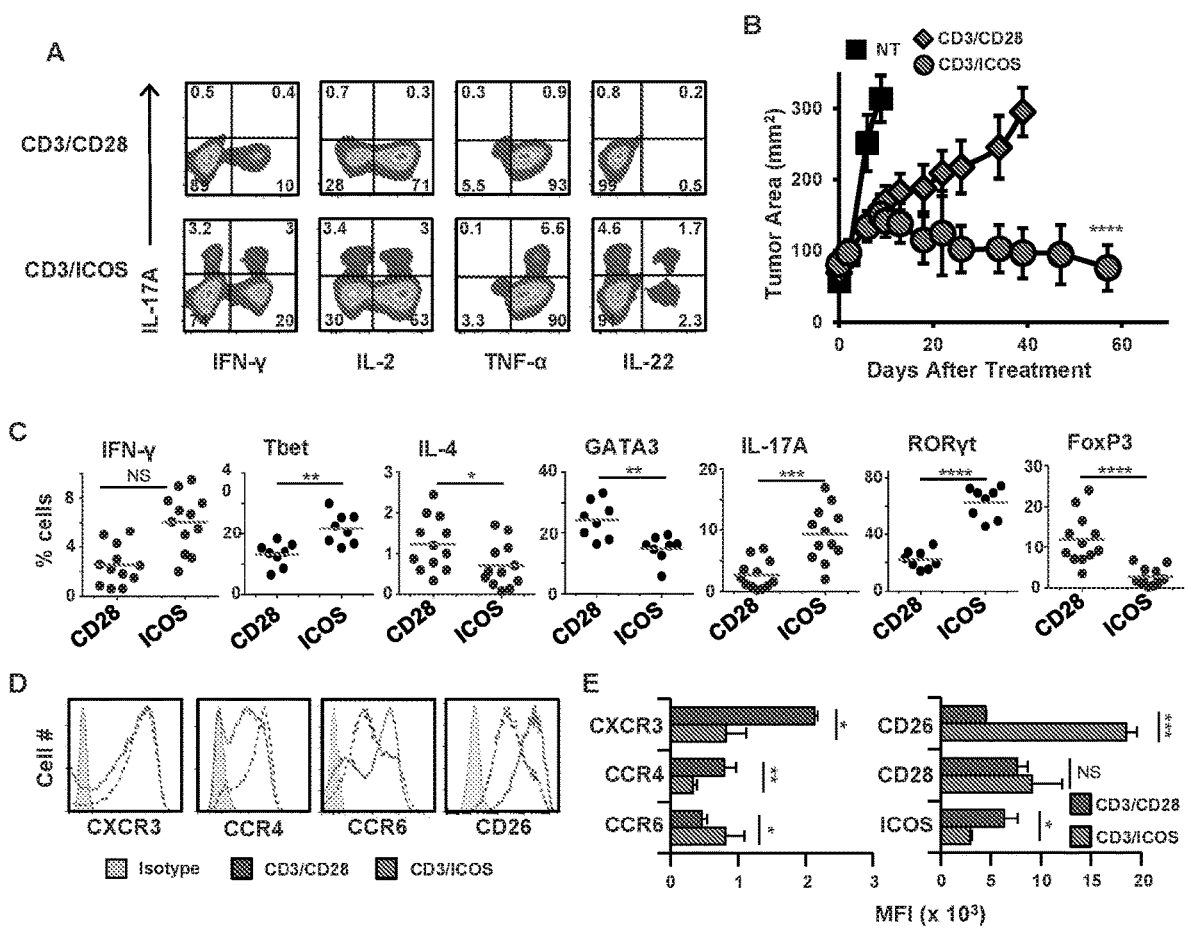
FIGS. 1A-1E: ICOS costimulation enhances antitumor Th17 cells activity and induces CD26. Human CD4$^+$ and/or CD8$^+$ T cells were stimulated with beads coated with antibodies to CD3/CD28 or CD3/ICOS and cultured with Th17-polarizing cytokines. Human normal donor polarized Th17 cells were stimulated with either αCD3/αCD28 or αCD3/αICOS beads. (A) Representative intracellular cytokine profiles 10 days following stimulation. (B) Genetically redirected/cytokine-programmed Th17 and Tc17 cells (2$^{nd}$ generation CAR with CD3ζ and CD137) were infused (two i.v. administrations, 8×10$^6$ cells total) into NSG mice given human mesothelioma (M108) tumor. 8 mice/group; representative of 2 independent experiments. All groups were significantly different from one another P<0.0001; linear regression. (C) Comparison of multiple donors showing the expression of cytokines and transcription factors associated with particular T cell subsets by flow cytometry. Histograms (D) and Mean Fluorescent Intensity (E) on Th17 polarized cells from 5 donors in independent experiments of CXCR3, CCR4, CCR6 and CD26 expression. *, P<0.05; , P<0.01; *, P<0.001; ****, P<0.0001; t-test.

Example 1—Human T Cells or Other Immune Cells that Express High CD26 Possess Durable Antitumor Properties Identification of a human CD4$^+$ T cell that expresses CD26: It has been previously reported that ICOS is constitutively expressed on human CD4$^+$ T cells polarized (via cytokines) to a Th17 but not Th1 or Th2 phenotype (Paulos et al., 2010). Th17 cell activation with ICOS [via an agonist antibody expressed on artificial APCs] augments their function, as indicated by increased secretion of IL-17A, IFN-γ, TNF-α and IL-22 (FIG. 1A). Conversely, Th17 activation with the classic co-stimulator CD28 reduced their ability to secrete IL-17A and IFN-γ but slightly enhanced IL-2 production. The antitumor activity of ICOS-stimulated Th17 cells (engineered to express a 2$^{nd}$-generation CAR containing CD3ζ and 41BB signaling domains downstream of single chain fragment variable recognition of mesothelin) in NSG mice bearing human mesothelioma was superior to that of CD28-expanded Th17 cells (FIG. 1B). CAR$^+$CD8$^+$ T cells needed to be co-infused with CAR+Th17 cells to regress large human tumors in vivo (FIG. 9A). Also, this therapy was less effective if cells were engineered with a 1$^{st}$-generation Meso-CAR that signals CD3ζ but does not contain co-stimulatory domains (FIG. 9B). These data show that 2$^{nd}$-generation CAR+Th17-polarized cells stimulated with ICOS mediate durable antitumor activity in mice bearing large human tumors.

Although ICOS augments the antitumor activity of Th17-polarized cells compared to those stimulated with CD28 (FIG. 1B), the cellular population(s) within this culture responsible for this antitumor activity remained unclear. Herein, it was discovered that Th17-polarized cultures give rise to cells with a Th2/Treg-like phenotype when activated with CD28, indicated by their high IL-4, GATA3, FoxP3 and CCR4 expression (FIG. 1C-E). Conversely, ICOS signaling favored Th17-polarized cells that secrete IFN-γ and IL-17A in multiple donors (FIG. 1C). These cells also expressed RORγt and chemokine receptor CCR6 (FIG. 1C-E). CXCR3 (Th1 marker) was slightly higher on CD28-stimulated Th17 cells (FIG. 1D-E), yet they did not express T-bet or IFN-γ more than cells stimulated with ICOS (FIG. 1C). ICOS signaling also promoted the generation of Th17 cultures that expressed heightened levels of CD26 (co-stimulatory molecule w/enzymatic properties (Moon et al., 2011)) on their cell surface (FIGS. 1D-E). Thus, it was found that ICOS and CD28 signaling expands diverse CD4$^+$ T subsets from their original Th17 cultures: perhaps explaining their differential ability to function and regress tumors.

CD26$^{high}$ T cells are multifunctional in vitro: Although ICOS stimulation expands a heterogeneous population of subsets from Th17-polarized cells, it remained unclear which subset(s) in the culture were responsible for regressing tumors. Also, the antitumor activity of distinct human CD4$^+$ subsets had not been compared side-by-side in an ACT tumor model. Given that high CD26 expression correlates with IL-17A production (Bengsch et al., 2012) and given that ICOS induces CD26 (FIG. 1D-E), it was suspected that CD26$^{high}$ T cells would regress human tumors in vivo to a greater extent than classic Th1, Th2 or Th17 cells. To address this idea, distinct CD4$^+$ T cell subsets were isolated via extracellular markers (Acosta-Rodriqeuz et al., 2007)) from the peripheral blood of healthy individuals using a flow sorting instrument. This strategy yielded Th1 (CXCR3$^+$CCR4$^-$CCR6$^-$), Th2 (CCR4$^+$CXCR3$^-$CCR6$^-$) and Th17 (CCR4$^+$CCR6$^+$CXCR3$^{+/-}$/) subsets. Additionally, the top~5% of CD4$^+$ T cells expressing CD26 were enriched to attain CD26$^{high}$ T cells (FIG. 2A). Compared to healthy individuals, the frequency of these 4 distinct subsets in the blood of melanoma patients is similar. It was noted that the frequency of CD4$^+$ T cells expressing CXCR3, CCR4, CCR6 and high CD26 was comparable in the blood of cancer patients vs. normal donors (FIG. 2B). Interestingly, CD26$^{high}$ T cells were highly multifunctional compared to CD4, Th1, Th2 or Th17 cells as verified by their enhanced capacity to co-secrete IL-17A, IFN-γ, TNF-α, IL-2, and IL-22 (FIG. 2C, 10A-10C). Th2 cells primarily secreted IL-4 (49%) while Th1 cells predominantly secreted IFN-γ (88%). Intriguingly, CD26$^{high}$ T cells secreted more IL-17A than classic Th17 cells (58% vs. 15%) and nearly as much IFN-γ as Th1 cells (73%). CD26$^{high}$ T cells also secreted abundant IL-22. CD26$^{high}$ T cells dually-secreted more IL-17A and IFN-γ than the other subsets (FIGS. 2C and 2D).

Figures 10A, 10B, 10C, 10D:
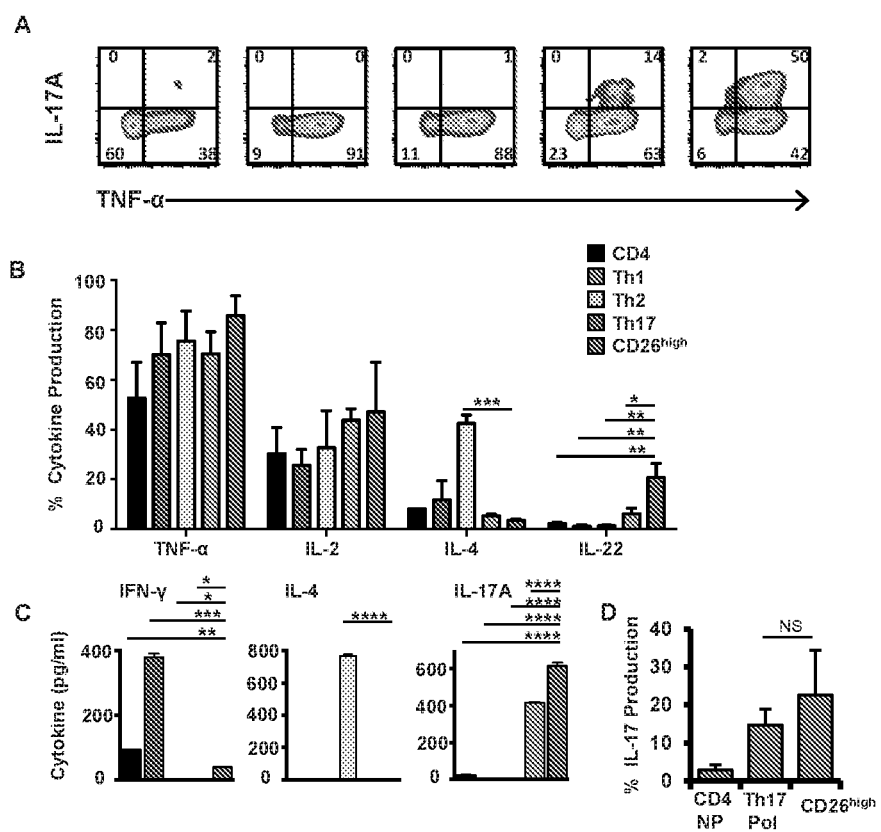

Strikingly, CD26$^{high}$ T cells were highly multi-functional, as they could concomitantly secrete 4 (35%) to 5 (7%) cytokines (FIG. 2E). It was reproducibly observed that CD26$^{high}$ T cells were robustly multifunctional in more than 100 different tested healthy normal donors and cancer patients. It was noted that CD26$^{high}$ T cells secreted as much IL-17A as bulk CD4 T cells programmed to a Th17 phenotype with multiple cytokines (FIG. 10D). This finding is important as Th17-polarizing requires a cytokine cocktail containing six reagents: IL-6, IL-1β, IL-21, IL-23 and antibodies that block IL-4 and IFN-γ. Cytokine programmed Th17 cells secreted 5-fold more IL-17A than un-programmed bulk CD4 controls. Yet CD26$^{high}$ T cells secreted as much or more IL-17A as polarized Th17 cells (FIG. 10D). Consequently, subsequent experiments with flow-enriched subsets were conducted without adding the six type 17-polarizing reagents to the culture. Although CD26$^{high}$ T cells have a unique functional profile, it remained unknown if these cells mounted a more effective antitumor activity than traditional human CD4 subsets.

Figures 3A, 3B, 3C, 3D:
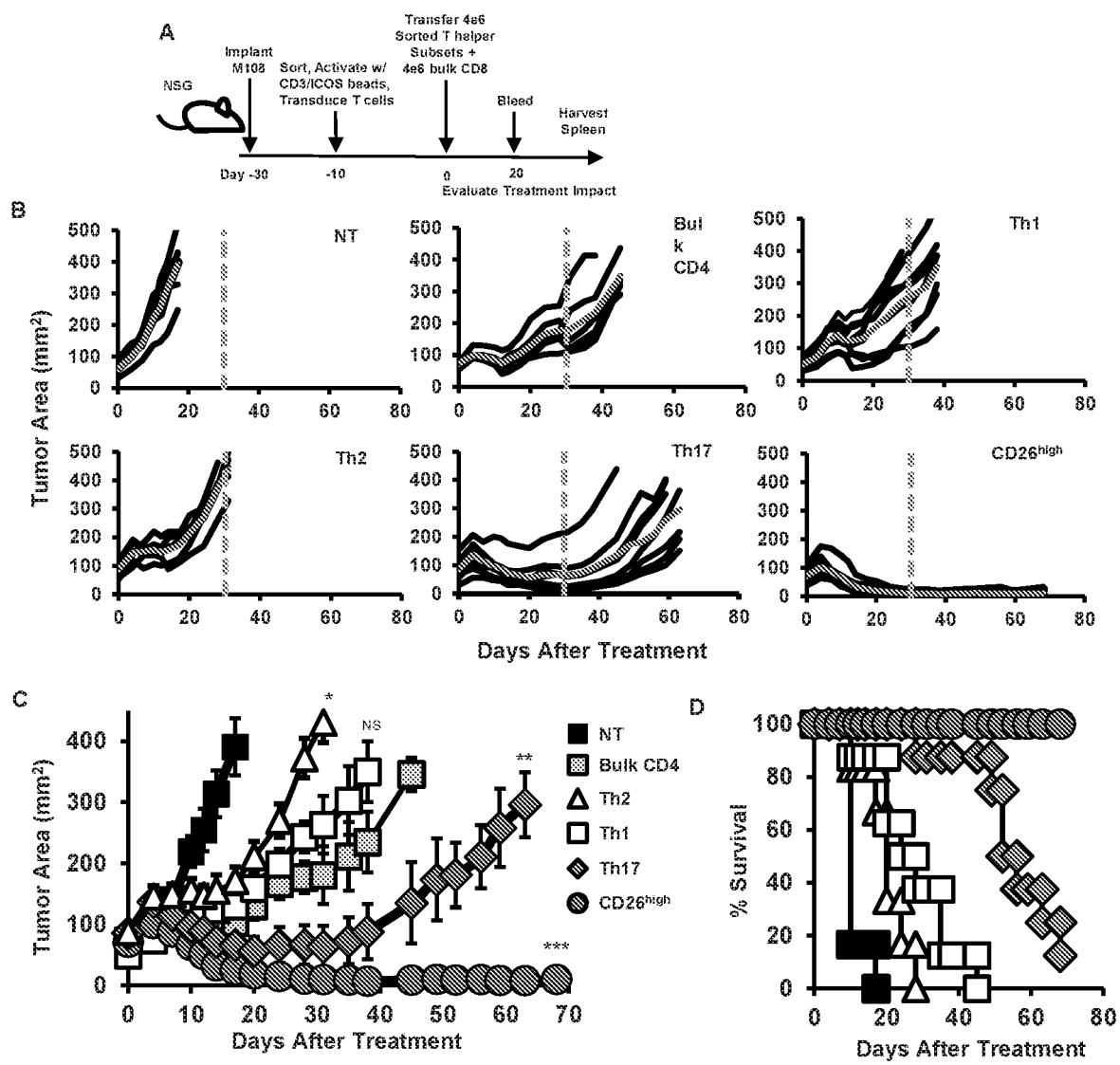
FIGS. 3A-3D: Human $CD26^{high}$ T cells are superior at regressing mesothelioma compared to other CD4 subsets. Th1 (CXCR3), Th2 (CCR4), Th17 (CCR4/CCR6), Th17 ($CD26^{high}$) or unsorted (bulk CD4) cells were sorted from normal donor PBL and then expanded with αCD3/αICOS bead at a 1 bead to:10 T cell ratio. Cells were transduced with a lentivirus containing a $1^{st}$ generation mesothelin-specific CD3ζ CAR and expanded with IL-2. NSG mice were SQ injected with human mesothelioma (M108) and allowed to establish for 30 days prior to ACT. A total of $4 \times 10^6$ transduced, sorted $CD4^+$ cells+$4 \times 10^6$ transduced $CD8^+$ cells were adoptively transferred. 50,000 IU IL-2 (low dose) were given to each mouse once per day for 3 days. (A) Scheme of in vivo experiment. (B) Tumor areas were calculated over time and displayed as individual mice. The red line is an average (6-8 mice/group). (C) Average tumor curves. All groups were significantly different from NT, P<0.005. CD4 vs. Th1 NS; CD4 vs. Th2, P=0.0015; CD4 vs. Th17, P=0.0035; CD4 vs. $CD26^{high}$, P=0.0003; Th17 vs. $CD26^{high}$, P=0.008; polynomial regression. (D) The percentage of mice with tumor areas below the 200 mm² threshold.
Figures 11A, 11B, 11C, 11D:
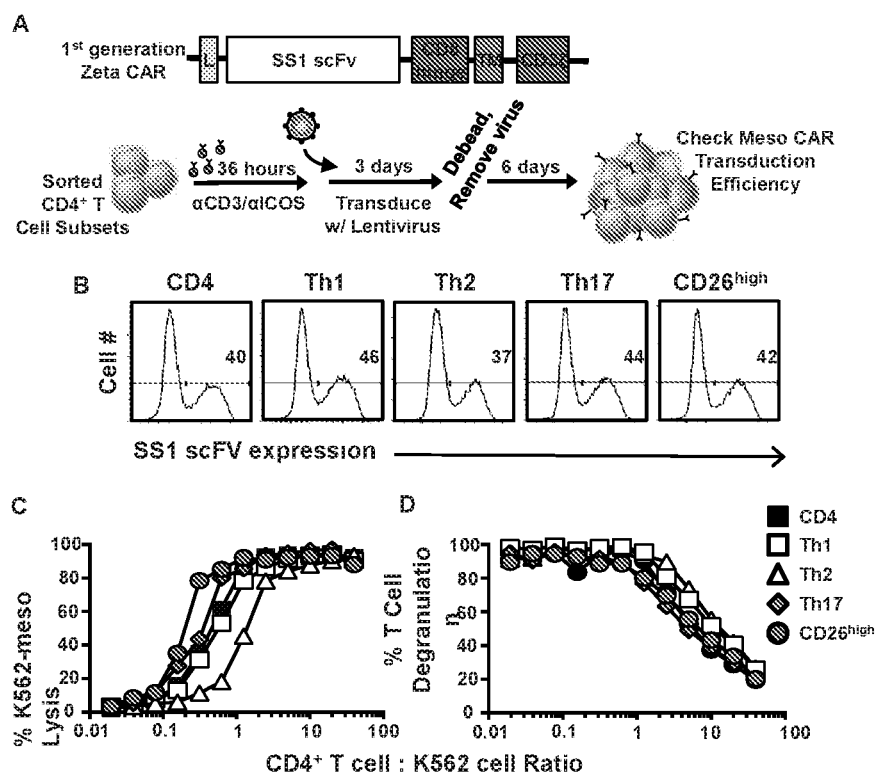

CD26$^{high}$ cells eradicate large human tumors and persist in vivo: As ICOS signaling expands Th17-polarized lymphocytes that express CD26 (FIG. 1D, 1E), it was postulated that they (CD26$^{high}$ T cells) were the cells responsible for regressing mesothelioma in vivo and, moreover, enriching them from other subsets in the blood would unleash their therapeutic potential in vivo, when engineered with a 1$^{st}$-generation CAR (FIG. 1B, 11A). To test this idea, sorted CD26$^{high}$, Th1, Th2 and Th17 subsets redirected to lyse mesothelin with a 1$^{st}$ gen-Meso-CAR were co-transferred with 1$^{st}$-gen-Meso-CAR$^+$CD8$^+$ T cells into NSG mice bearing large human M108 mesothelioma (scheme in FIG. 3A). It was found that bulk CD4$^+$ T cells only slightly delayed tumor growth in vivo (FIG. 3B, 3C). Th1 cells mediated comparable tumor regression as bulk CD4$^+$ T cells, while Th2 cells were less effective than all other therapies. Th17 cells were more effective at clearing human tumors than Th1 cells. Strikingly, in support of the hypothesis, CD26$^{high}$ T cells eradicated tumors to a far greater extent than all other subsets. Additionally, mice treated with CD26$^{high}$ T cells survived longer than treatment with other subsets (FIG. 3D). These data suggested that human CD4$^+$ T cell subsets distinctly regulate tumor immunity in a relevant humanized NSG mouse model and uncovered a new therapeutic role for CD26$^{high}$ T cells in cancer immunotherapy.

Figures 4A, 4B, 4C, 4D, 4E, 4F, 4G:
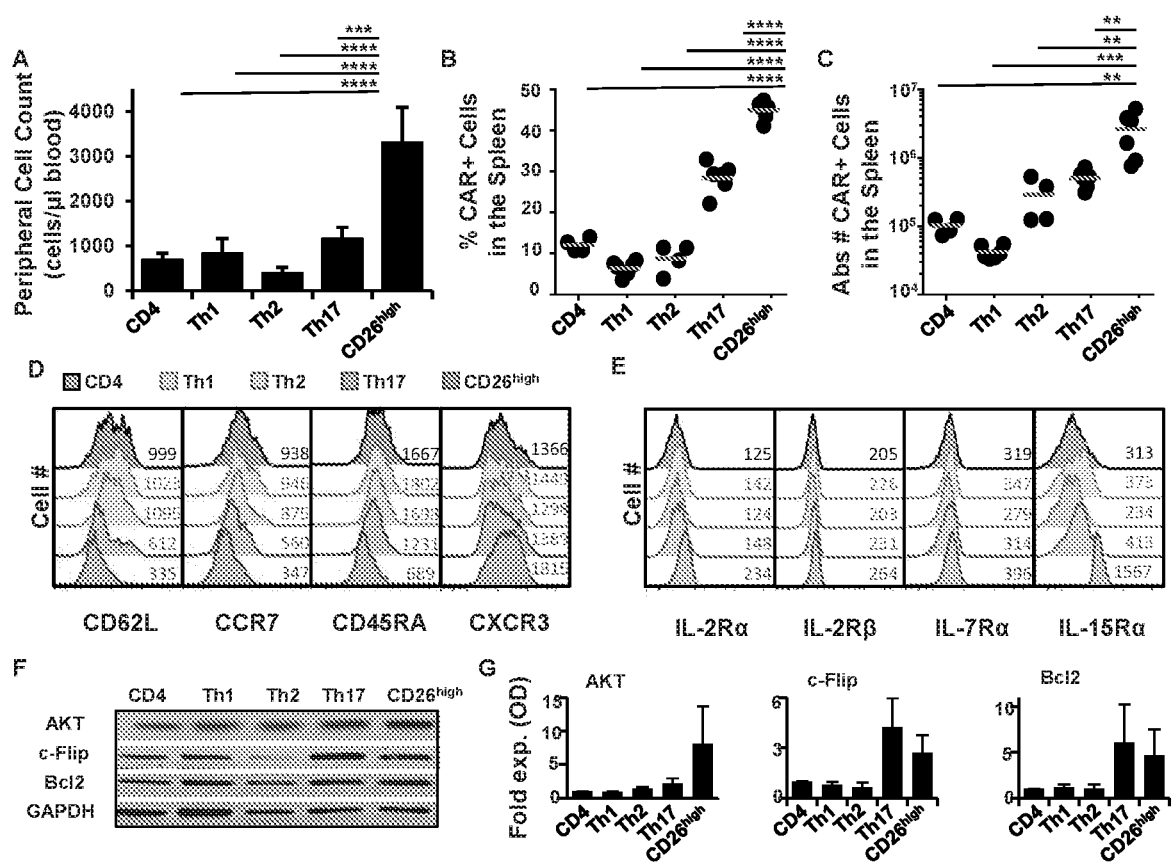
FIGS. 4A-4G: Human $CD26^{high}$ cells robustly engraft and persist in vivo and possess an effector memory phenotype. (A-D) Sorted as Th1, Th2 Th17, $CD26^{high}$ or unsorted $CD4^+$ cells were transferred into mesothelioma-bearing NSG mice as described in FIG. 3A. (A) Blood was analyzed at day 20 for $CD45^+CAR^+CD4^+$ cells using TrueCount beads (6 mice/group). (B, C) Spleens were analyzed for the percentage and total number of $CD45^+CAR^+CD4^+$ cells. Compared to $CD26^{high}$ , P<0.01; *, P<0.001; ****, P<0.0001; ANOVA. (D) $CD45^+CAR^+CD4^+$ splenocytes were examined for their memory phenotype. Representative from 6 mice. (Top to bottom: CD4, Th1, Th2, Th17, and $CD26^{high}$). (E) Expression of homeostatic cytokine receptors following cell sorting. Representative from 3 donors. (F, G) Cytoplasmic fractions from day 10-expanded cells were probed for anti-apoptotic genes via Western Blot. Representative and averages compared to $CD4^+$ cells (3 donors). GAPDH was used as the loading control.
Figures 12A, 12B, 12C, 12D:
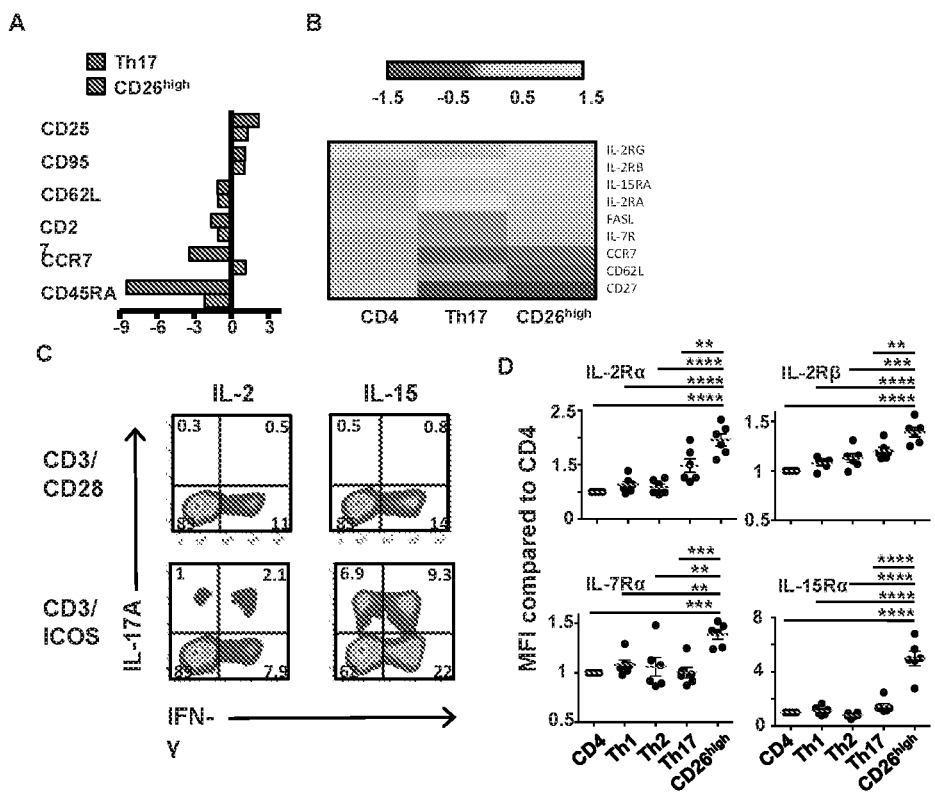

It was found that CD26$^{high}$ T cells persisted far better than Th1, Th2 or Th17 cohorts in vivo. Three-fold more CD26$^{high}$ T cells were detected in the blood and spleen of mice compared to mice treated with other subsets (FIGS. 4A-C). Post infusion, CD26$^{high}$ T cells gained an effector memory phenotype compared to other subsets, as they expressed less CD62L, CD45RA and CCR7 than Th1, Th2 or Th17 cells (FIGS. 4D, 12A-B). Interestingly, as shown in FIG. 4D, CD26$^{high}$ T cells expressed more CXCR3 than Th1 cells in vivo. This result was surprising as Th1 but not CD26$^{high}$ T cells were enriched via CXCR3. It was suspected that CD26$^{high}$ T cells were able to persist in animals better than other subsets as they expressed more receptors for various homeostatic cytokines, such as IL-2Rα, IL-2Rβ, IL-7Rα and IL-15Rα (FIGS. 4E, 12C-D). CD26$^{high}$ T cells also expressed more anti-apoptotic and survival molecules, including Akt, bcl-2 and c-flip, than Th1 or Th2 (FIG. 4F, 4G). These data suggested that the cytokine receptors and survival molecules expressed on CD26$^{high}$ T cells aide their ability to persist in mice months transfer (FIGS. 4A-C).

Figures 5A, 5B, 5C, 5D, 5E:
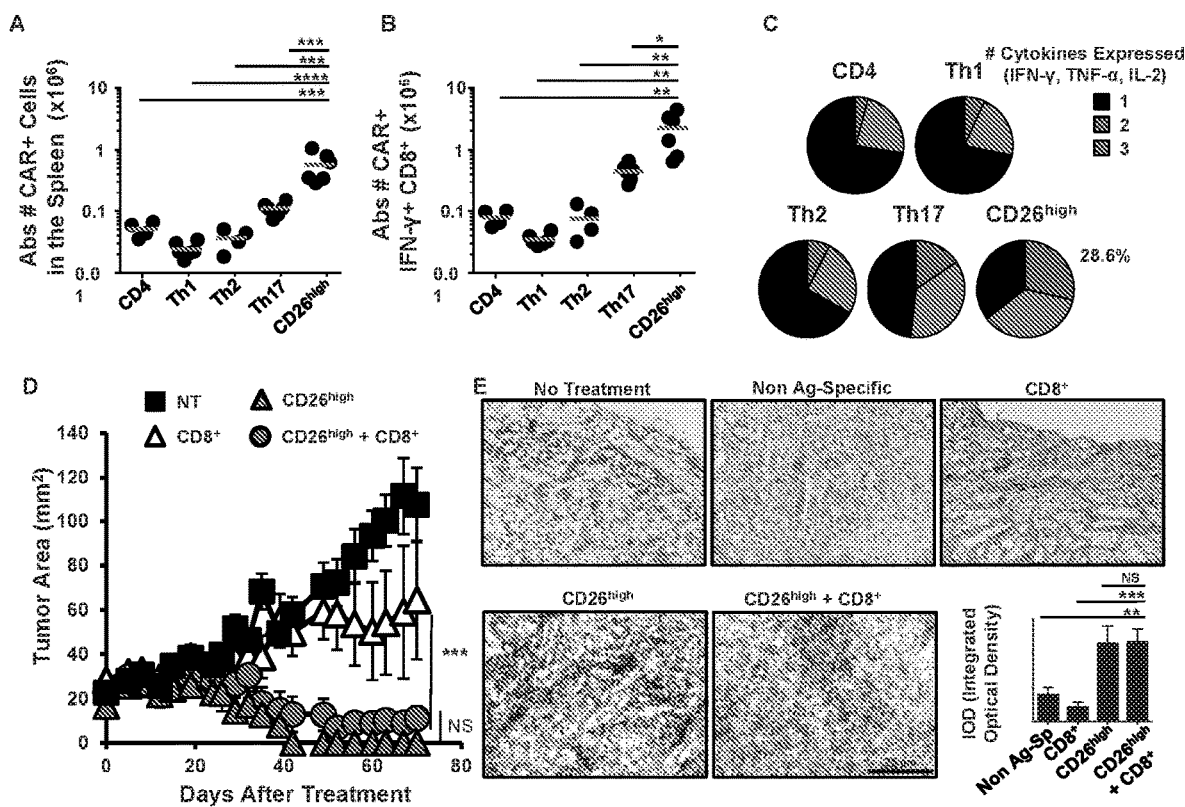
FIGS. 5A-5E: Human $CD26^{high}$ cells robustly engraft and persist in vivo and possess an effector memory phenotype. (A-C) Sorted as Th1, Th2 Th17, $CD26^{high}$ or unsorted $CD4^+$ cells were transferred into mesothelioma-bearing NSG mice as described in FIG. 3A. (A) Absolute number of splenic $CAR^+CD8^+$ (6 mice/group). (B) Total number of splenic IFN-γ-producing $CAR^+CD8^+$ cells. Average of 6 mice/group. Compared to $CD26^{high}$ *, P<0.05; , P<0.01; *, P<0.001; **, P<0.0001; ANOVA. (C) Simultaneous intracellular cytokine production in $CAR^+CD8^+$ cells. Average of 6 mice/group. (D) Mesothelioma growth in NSG mice treated with $CD26^{high}$ T cells co-infused with or without $CD8^+$ T cells—all engineered with $1^{st}$-gen-Meso-CAR. Two infusions of cells were given one week apart (250,000 cells i.v.; 160,000 cells i.t.). 5-6 mice/group. All groups were significantly different, P<0.001, except $CD8^+CD26^{high}$ vs. $CD26^{high}$, P<0.43. (E) Immunohistochemistry staining of M108 from NSG mice treated with $1.45 \times 10^6$ $CD26^{high}$ and $CD8^+$ T cells transduced with a $1^{st}$-gen-Meso-CAR having either full-length CD3ζ signaling or a non-signaling truncated version. Staining of human CD45 and hematoxylin on day 84 post-transfer (×10; 3 or 4 mice/group; average IOD from 10 images). Compared to $CD26^{high}$ , P<0.01; ***, P<0.001; ANOVA.

The data demonstrated that co-infusion of Meso-CAR$^+$ CD26$^{high}$ and CD8$^+$ T cells mediated curative responses in mice (FIG. 3). This finding was surprising in light of recent work that found that enzymatic cleavage of active CXCL10 by murine CD26 reduced the ability of CXCR3$^+$CD8$^+$ T cells to traffic to the tumor (Barreira da Silva et al., 2015). This group also reported that inhibiting CD26 augmented various forms of cancer immunotherapy. As both murine and human CD26 are enzymatic, it was hypothesized that human CAR$^+$CD26$^{high}$ T cells would also suppress human CAR$^+$ CD8$^+$ T cell engraftment in vivo. In opposition to this reported mouse data, it was found that human CD26$^{high}$ T cells fostered the persistence of co-transferred human CD8$^+$ T cells to a greater extent than the other human CD4$^+$ subsets (FIGS. 5A, 13A-B). Moreover, these CD8$^+$ T cells were more polyfunctional, as demonstrated by the ability of ~30% of them to concomitantly co-secrete IFN-γ, TNF-α and IL-2 (FIGS. 5B-C). Interestingly, treatment of mice with CD26$^{high}$ T cells alone could regress mesothelioma as effectively as those co-treated with CD26$^{high}$ plus CD8$^+$ T cells (FIG. 5D). In contrast to CD26$^{high}$ T cell alone therapy, treatment with CAR$^+$CD8$^+$ T cells alone was ineffective and mice rapidly succumbed to their disease. This data was unexpected given the finding that CAR$^+$Th17 cells regress tumor better when co-infused with CAR$^+$CD8$^+$ T cells (FIG. 9A). Treatment with CD26$^{high}$CD4$^+$ plus CD8$^+$ T cells effectively infiltrated the tumor, as shown by IHC (FIG. 5E). This work underscores that CD26$^{high}$CD4$^+$ T cells augment CD8$^+$ T cell engraftment and function in vivo. However, CD26$^{high}$ T cells but not Th17 cells were able to regress tumors without the need of CTLs, thereby mediating long-term cures in mice.

Figures 6A, 6B:
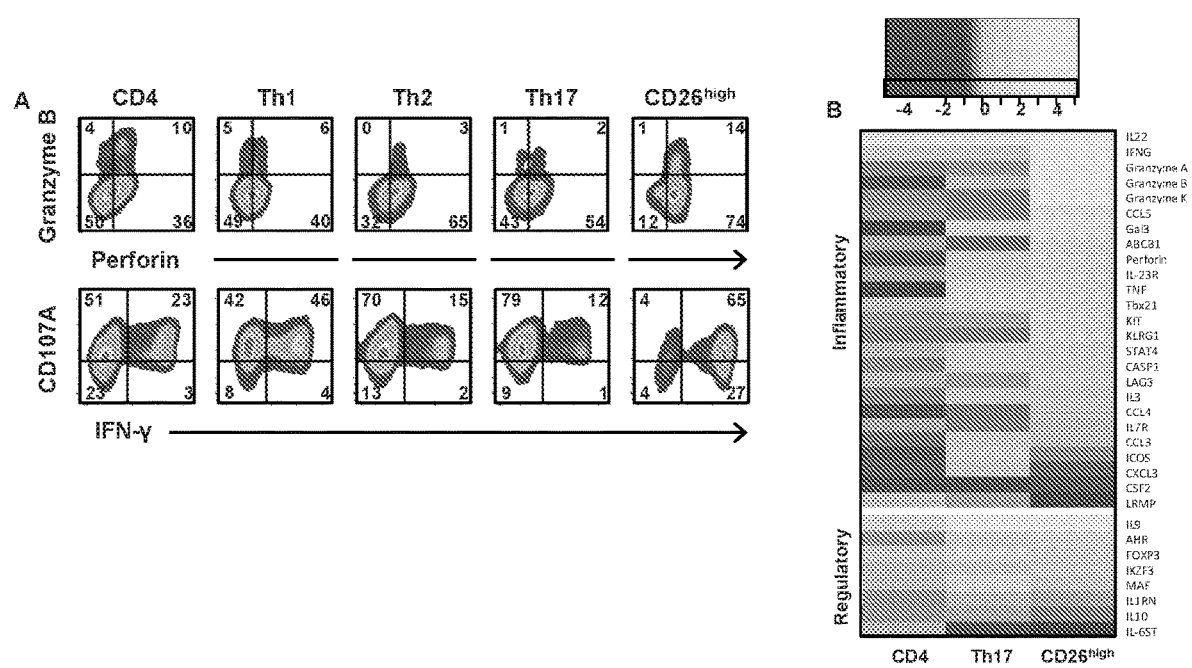
FIGS. 6A-6B: Human $CD26^{high}$ T cells have a unique inflammatory and molecular signature compared to human Th17 cells. $CD4^+$ T cell subsets were sorted from normal human donors based on their surface marker expression. (A) Cytotoxic molecules granzyme B, perforin, CD107A and IFN-γ expression on sorted T cell subsets were assessed 10 days following activation. (B) RNA was isolated and gene expression levels were determined by OneArry on day 0 following sorting. Heat map of log 2-fold change in expression of Th17 effector- and regulatory-associated genes.

CD26$^{high}$ T cells are cytotoxic and have a distinct inflammatory signature: It was found that CD26$^{high}$ T cells clear tumors without CD8$^+$ T cells in vivo. Consequently, it was hypothesized that they are cytotoxic like classic CD8$^+$ T cells. In support of this idea, it was found that CD26$^{high}$ T cells secreted more perforin than Th1, Th2 or Th17 cells (FIG. 6A). Also, CD26$^{high}$ T cells co-expressed greater CD107A and IFN-γ than Th1 cells, underscoring their pronounced cytotoxic potential. Granzyme B was secreted at comparable amounts by all CD4 subsets. Motivated by this finding, it was next examined if CD26$^{high}$ T cells possessed an inflammatory phenotype described by the Kuchroo lab in pathogenic Th17 cells. This lab and other labs (Lee et al., 2012; Ramesh et al., 2014)) reported that the molecular signature of a Th17 cell is influenced by distinct cytokines IL-12 or TGF-β, which skew them to either an inflammatory or regulatory phenotype respectively. Based on their functional and cytotoxic profile, it was posited that CD26$^{high}$ T cells were inflammatory while sorted Th17 cells were regulatory. Indeed, even when CD26$^{high}$ T cells were enriched from healthy donor peripheral blood and were not ex vivo manipulated, it was found that these cells possessed an inflammatory signature, as they expressed more IL-23R, granzyme B, IL-22, tbx21 IL-23r stat3, ccl5, and perforin at the gene level than Th17 cells (FIG. 6B). Unexpectedly, CD26$^{high}$ T cells also expressed regulatory molecules identified by others as "regulatory Th17 cells," such as IL-9 and ahr. As anticipated, Th17 cells possessed a regulatory/Th2 profile (foxp3, ccr4 and maf) compared to CD26$^{high}$ T cells. Th17 cells however expressed some key inflammatory markers to a greater extent than CD26$^{high}$ T cells, such as icos and cxcl3. Although CD26$^{high}$ T cells possess an inflammatory profile, they also possess some regulatory properties at the molecular level, suggesting that they are a T cell population unique from classic Th17 cells or inflammatory Th17 cells previously identified by other groups.

Figure 14F:
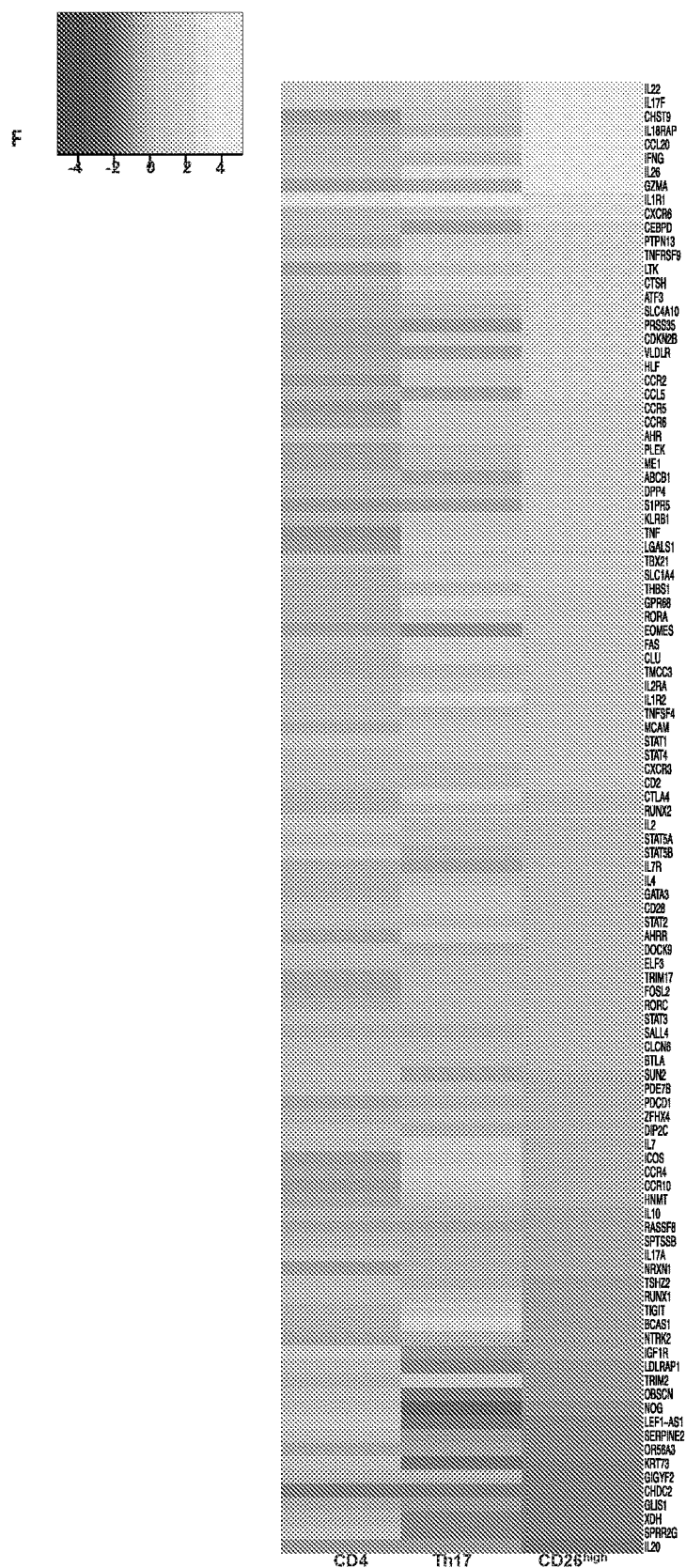

As CD26$^{high}$ T cells are more inflammatory, it was suspected they might be more cytotoxic in vitro and in vivo than other CD4 subsets. It was hypothesized that CD26$^{high}$ T cells would more effectively lyse tumor cells than Th1, Th2 or Th17 cells. To address whether CD26$^{high}$ T cells were able to lyse cells in vitro, enriched subsets were engineered to express a 1$^{st}$-gen-Meso-CAR and their ability to lyse targets was tested. As shown, CD26$^{high}$ T cells were marginally better at lysing tumor targets (mesothelin-positive K562 cells) in vitro (FIG. 6C). While nominal differences were observed in the lytic potential of these four subsets in vitro, it was next examined how they would impact antitumor immunity in vivo long term It was surmised that CD26$^{high}$ T cells were distinct from Th1 or Th17 cells based on our gene array and functional data. To address this concept, microarray was used to further examine their molecular signature. Strikingly, CD26$^{high}$ T cells not only expressed markers used to characterize Th17 cells, but also expressed genes used to discern Th1, Th22 and MAIT/iNKT cells, as shown extensively in FIGS. 7A and 14A. For example, at the molecular level, CD26$^{high}$ T cells expressed the highest rorγt/rorα, tbet/eomes, ahr and plzf; master transcription factors for Th17, Th1, Th22 and MAIT cells, respectively. Conversely, classic Th17 cells expressed rorγt/rorα and greater regulatory transcription factors FoxP3 and Hellios. Likewise, at the protein level, Tbet and RORγt, but not FoxP3 or GATA3, were expressed in CD26$^{high}$ T cells (FIG. 14B). As CD26$^{high}$CD8$^+$ T cells have been reported to be MAIT cells (Sharma et al., 2015), it was sought to examine if CD4$^+$ CD26$^{high}$ T cells were also MAIT cells using additional markers that discern this phenotype. Flow cytometry data suggested that they were not traditional MAIT, as they did not express MR1 or Vα7.2. By displaying a plethora of genes via principal component analysis (FIGS. 14F, 14G), the data suggest that CD26$^{high}$ T cells are distinct from Th17 cells.

Figures 7A, 7B, 7C, 7D:
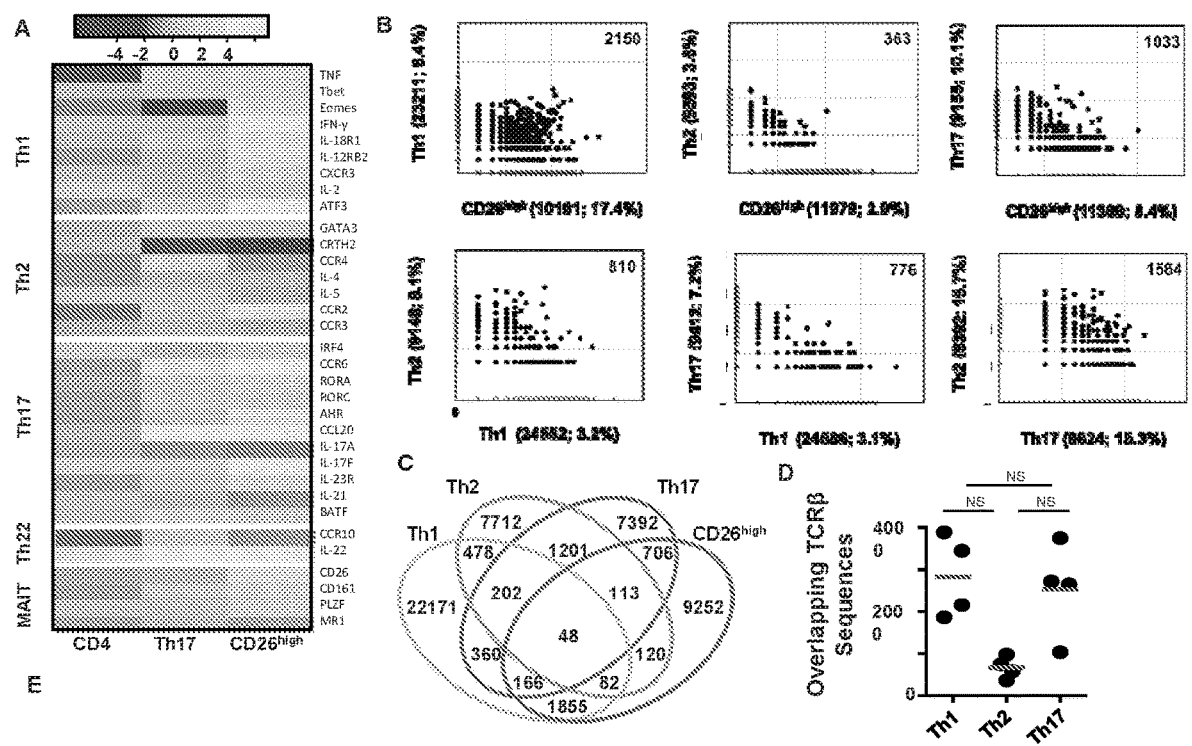
FIGS. 7A-7D: Human $CD26^{high}$ T cells have a unique inflammatory and molecular signature compared to human Th17 cells. $CD4^+$ T cell subsets were sorted from normal human donors based on their surface marker expression. (A) Heat map of log 2-fold change in expression of $CD4^+$ T cell subset-associated genes. (B, C) T cell subsets were sorted from normal human donors. DNA was isolated, TCRβ sequences were expanded using an immunoSEQ kit and subsequently sequenced. Representative from 4 donors. (B) Data shown is the comparison of percent productive frequency of TCRβ sequences between 2 subsets. Compared to $CD26^{high}$ Th1 RR=2.97, Th2 RR=1.24, Th17 RR=3.327, Th1 compared to Th2 RR=1.52, Th17 RR=1.34, Th2 compared to Th17 RR=6.73; log-linear two-way interaction model. (C) Venn diagram displaying the frequencies of identical TCR sequences between all subsets. (D) Number of overlapping TCRβ sequences with $CD26^{high}$ T cells. Display of 4 normal donors.

To further delineate CD26$^{high}$ T cells from Th1 and Th17 cells, a comparative analysis of the TCRβ repertoire was executed. Of the 12342 clonotypes in CD26$^{high}$ T cells, many identical sequences overlapped with Th1 and Th17 cells (2151 and 1033 clones, respectively; FIG. 7B). However, fewer CD26$^{high}$ T cell clonotype sequences overlapped with Th2 cells (363 clones). In contrast, there was a strong clonotype sequence overlap between Th2 and Th17 subsets (1564 clones). The data revealed overlap in TCRβ sequences between all subsets in this single donor (FIG. 7C) and among all 4 different donors analyzed (FIG. 7D). These findings suggest that CD26$^{high}$ T cells possess a molecular and cellular profile associated with, yet unique, from classic Th1, Th2 or Th17 cells.

Figures 8A, 8B, 8C, 8D, 8E, 8F, 8G:
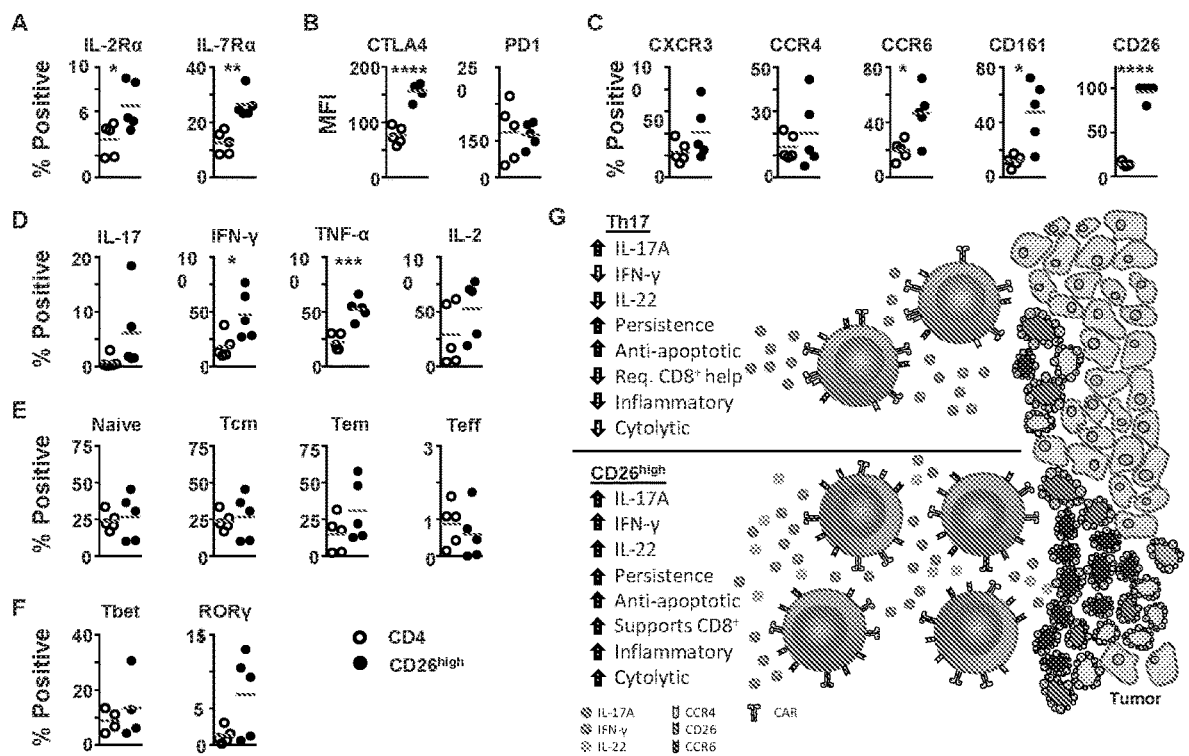
FIGS. 8A-8G: $CD26^{high}$ T cells in the peripheral blood of metastatic melanoma patients have a similar phenotype to those from healthy donors. Peripheral blood was obtained from de-identified patients with metastatic melanoma (Mel Pt.). Lymphocytes were enriched and cells were stained for flow cytometry. For all graphs, lymphocytes were gated for either $CD4^+$ or $CD4+CD26^{high}$ (top 5% of CD26 expression) and a comparison is made. (A) Shown are the percent positive cells for IL-2Rα (CD25) and IL-7Rα (CD127). (B) Mean fluorescent intensity (MFI) of CTLA4 and PD1 expression. (C) Percentage of cells expressing chemokine receptors or CD26 which correlate with $CD4^+$ T cell subsets.

Finally, of important clinical significance, it was not only found that that CD26$^{high}$ T cells exist at the same frequency in melanoma patients as they do in healthy individuals (FIG. 2B), but that they all possess many of the functional and phenotypic properties as those enriched from healthy individuals. For example, similarly to CD26$^{high}$ T cells from healthy donors, those enriched from cancer patients also expressed heightened amounts of homeostatic cytokine receptors on their cell surface (such as IL-2Rα and IL-7Rα, FIG. 8A), significantly higher CTLA4 (FIG. 8B), more chemokine receptor CCR6 (FIG. 8C) and co-secreted elevated amounts of inflammatory cytokines (IFN-γ, IL-2, IL-17A and TNF-α, FIG. 8D) than bulk CD4 T cells. CD26$^{high}$ T cells from the blood of melanoma patients were composed of similar frequencies of central and effector memory T cells as found in healthy individuals (FIG. 8E). Similar to healthy donors, CD26$^{high}$ T cells enriched from several melanoma patients expressed higher RORγt than CD4$^+$ T cells (FIG. 8F). Collectively, these data imply that CD26$^{high}$ T cells can be successfully enriched from cancer patients. As was found that CD26$^{high}$ T cells possess potent antitumor properties and persist effectively in mice with large established human tumors, this data suggest they could be used to improve ACT therapies.

In summary, and as depicted in FIG. 8G, human CD4$^+$ T cells that express high CD26 are multifunctional, cytolytic and possess a unique inflammatory profile. These cells are rich in cytokine receptors and possess pathways rendering them resistant to apoptosis, thus permitting their robust engraftment, persistence and infiltration into large solid tumors. These traits license CD26$^{high}$ T cells to regress tumors more effectively than other CD4$^+$ subsets and bolster the engraftment and multifunctionality of co-infused CTL. These findings have clinical implications for the development of next generation cancer immunotherapies with this unique human CD4$^+$ T cell subset found in patients' peripheral blood.

Example 2—Materials and Methods

Subset Isolation: De-identified, normal human donor peripheral blood cells were purchased as a buffy coat (Plasma Consultants) or leukapheresis (Research Blood Components). The PBL were enriched using Lymphocyte Separation Media (Mediatech). CD4$^+$ T cells were then negatively isolated using magnetic bead separation (Dynabeads, Invitrogen) and plated in culture medium with a low concentration of rhIL-2 (20 IU/ml; NIH repository) overnight. For in vivo studies, CD8$^+$ T cells were positively isolated prior to the enrichment of CD4$^+$ T cells. The following morning CD4$^+$ T cells were stained using PE-CD26 (C5A5b), AlexaFluor647-CXCR3 (G025H7), PECy7-CCR6 (G034E3, Biolegend), FITC-CCR4 (205410, R&D Systems) and APCCy7-CD4 (OKT4, BD Pharmingen). Cells were sorted based on the following gating strategies: bulk CD4: CD4$^+$; Th1: CD4$^+$CCR6$^-$CCR4$^-$CXCR3$^+$; Th2: CD4$^+$CCR6$^-$CCR4$^+$CXCR3$^-$; Th17: CD4$^+$CCR6$^+$CCR4$^+$; CD26: CD4$^+$CD26$^{high}$. Cells were sorted on a BD FACSAria IIu Cell Sorter or on a Beckman MoFlo Astrios High Speed Cell Sorter.

Cell culture: T cell subsets were expanded in RPMI 1640 culture medium supplemented with non-essential amino acids, L-glutamine, sodium pyruvate, HEPES, Pen/Strep, β-mercaptoethanol, and FBS. Cells were cultured at either a 1:1 or 1:10 bead to T cell ratio. Magnetic beads (Dynabeads, Life Technologies) coated with antibodies to CD3 (OKT3) and CD28 (CD28.2) or ICOS (ISA-3, eBioscience) were produced in the lab according to manufacturers' protocols. One hundred IU/ml rhIL-2 (NIH repository) were added on day 2 and media was replaced as needed. For Th17 polarization, IL-13 (Shenandoah; 10 ng/ml), IL-6 (NIH repository; 10 ng/ml), IL-23 (PeproTech 20 ng/ml) and neutralizing antibodies for IFN-γ (B27) and IL-4 (MP4-25D2; BioXCell; 5 µg/ml) were added during activation. IL-23 and IL-2 were added during expansion.

Analysis of metastatic melanoma patient samples: Peripheral blood samples drawn from de-identified metastatic melanoma patients (Mel Pt) and the lymphocyte population was enriched. PBMCs were either immediately stained for flow cytometry or cryopreserved and stained at a later time. Mel Pt samples were assayed in parallel to normal healthy donors. CD4+ T cells were compared to gated CD4+ CD26$^{high}$ T cells for all markers of interest. Patients gave written, informed consent in accordance with the Declaration of Helsinki. The study was approved by the Medical University of South Carolina Institutional Review Board.

Flow cytometry phenotyping: For all intracellular staining data cells were stimulated with PMA/Ionomycin. After one hour, monensin (Biolegend) was added and incubated for another 3 hours. Following surface staining, intracellular staining with antibodies was performed according to the manufacturer's protocol using Fix and Perm buffers (Biolegend). Transcription factor staining was executed using the FOXP3 staining buffer set (eBioscience) as recommended by the manufacturer. Data were acquired on a BD FACSVerse or LSRII X-20 (BD Biosciences) and analyzed using FlowJo software (Tree Star, Ashland, OR).

Anti-mesothelin CAR T cells: To generate mesothelin-specific T cells, αCD3/αICOS-activated, sorted CD4$^+$ and bulk CD8$^+$ T cells were transduced with a chimeric anti-mesothelin single-chain variable fragment (scFv) fusion protein containing the T cell receptor ζ (TCRζ) signaling domain (1$^{st}$-gen-Meso-CAR) that was generated as described previously (16). In most experiments a 1$^{st}$-gen-Meso-CAR having full-length CD3ζ signaling (ζ) was used. In one experiment a non-signaling truncated version (Δ) of the 1$^{st}$-gen-Meso-CAR was utilized. CAR expression was determined using a flow cytometry antibody specific for the murine F(ab')$_2$ fragment (Jackson ImmunoResearch, 115-606-006).

In vitro CTL assay: Sorted CD4$^+$ T cell subsets were activated with αCD3/αICOS beads, engineered to be mesothelin specific using a lentiviral CAR. Following a 10-day expansion, equal numbers of CAR$^+$ T cells were co-cultured overnight with meso-expressing K562 cells (pre-stained with Cell Trace Violet, Molecular Probes) serially diluted in the presence of CD107A (Pharmingen). K562 lysis was determined by 7-AAD (Pharmingen) uptake. Degranulation of CAR$^+$CD4$^+$ T cells was quantified by CD107A staining by flow cytometry. K562-meso cells were tested for mycoplasma (MycoAlert, Lonza) and mesothelin (R&D Systems, FAB32652) expression during expansion.

Mice and tumor line: NOD scid gamma (NSG, The Jackson Laboratory) were bred at the University of Pennsylvania or at the Medical University of South Carolina. The mice were housed under specific pathogen-free conditions in microisolator cages and given ad libitum access to autoclaved food and acidified water. Both male and female mice were used between the ages of 6 and 12 weeks of age. M108 xenograft tumors, described previously (Carpenito et al., 2009), were tested for mycoplasma during expansion (Lonza). Prior to therapy, tumors were measured and mice were randomized based on tumor size-mice with very small or without a visible tumor were excluded from the experiment. Tumors were measured using calipers by personnel blinded to the groups. Tumor endpoint was reached when tumor area exceeded 400 mm$^2$. Remaining mice were euthanized and spleens harvested when more than half of the mice in a group reached tumor endpoint.

Western blot: Nuclear and cytoplasmic protein extracts from cultured cells were lysed using Nuclear and Cytoplasmic Extraction Reagent with Protease & Phosphatase Inhibitor Cocktail (ThermoScientific). Protein concentration was quantified using BSA Protein Assay Kit (ThermoScientific). Ten-30 µg of total protein was separated on a Mini-PROTEAN TGX, Any kD™ gel followed by transferred onto PVDF membranes (Bio-Rad). The membranes were then blocked with 5% non-fat dry milk in TBS buffer containing 0.5% Tween 20. The membranes were incubated ON at 4° C. with primary antibodies to RORγt (4F3-3C8-2B7), FoxP3 (150D, Biolegend), T-bet (eBio4B10, eBioscience), cFLIP (ab6144, Abcam) Akt (C67E7), Bcl-2 (D17C4), Caspase-3 (8G10), GATA-3 (D13C9), Histone-3 (D1H2) or GAPDH (D16HH, Cell Signaling) at recommended concentrations. Following washes, membranes were incubated for 1 h at room temperature with secondary antibodies: horseradish peroxidase (HRP)-conjugated goat antibodies to mouse or rabbit IgG (Cell Signaling). Chemiluminescence was performed using Western ECL Blotting Substrate (Bio-Rad) followed by X-ray film-based imaging. Films were scanned and quantification of the integrated optical density (IOD) was performed using ImageJ software. To remove antibodies, membranes were incubated for 15 min at room temperature in Restore Western Blot Stripping Buffer (ThermoScientific).

MicroArray: RNA was isolated from sorted CD4$^+$ T cells using the Quiagen RNeasy Mini kit and frozen. RNA was submitted to Phalanx Biotech Group for processing on their OneArray platform (San Diego, CA). RNA quantity and purity was assessed using NanoDrop ND-1000. Pass criteria for absorbance ratios are established as A260/A280≥1.8 and A260/A230≥1.5 indicating acceptable RNA purity. RIN values are ascertained using Agilent RNA 6000 Nano assay. Pass criteria for RIN value is established at >6 indicating acceptable RNA integrity. gDNA contamination was evaluated by gel electrophoresis. Target preparation was performed using an Eberwine-based amplification method with Amino Allyl MessageAmp II aRNA Amplification Kit (AM1753, Ambion) to generate amino-allyl antisense RNA (aa-aRNA). Labeled aRNA coupled with NHS-CyDye was prepared and purified prior to hybridization. Purified coupled aRNA was quantified using NanoDrop ND-1000; pass criteria for CyDye incorporation efficiency at >15 dye molecular/1000 nt.

GPR files were loaded into Rosetta Resolver System for data analysis. Random factors and systematic biases are estimated by the Rosetta error model calculation. Duplicate probes are averaged. Median scaling was performed for normalization. Differentially expressed genes were defined as having a log 2 fold change≥1 and p<0.05. Where log 2 ratios="NA", the differences in intensity between the 2 samples had to be >=1000.

Heatmap and PCA clustering: Graphing was performed in R (version 3.1.2) using gplots (version 2.16.0). Log$_2$ values for CD4$^+$ cells were averaged and used as baseline for the genes of interest. For each individual sample the fold change relative to baseline was calculated and the median value for the triplicates was calculated and used for generating figures.

Immunohistochemistry: Subcutaneous tumors were excised on day 84 post T cell transfer, and preserved in Crytomatrix (ThermoFisher). Standard BioLegend protocol was followed. Briefly, cryosections of fixed xenograft tumor tissues (5 µm thick) were treated with −20° C. acetone for 10 minutes, rinsed and exposed to 0.3% hydrogen peroxide for 10 minutes before blocking and subsequent incubation with primary antibody (CD45, 2B11_PD7/26, 1:100; DAKO) overnight at 4° C. Slides were washed and incubated with secondary antibody (Polymer-HRP) and developed with DAB substrate kit (DAKO). Slides were counterstained with hematoxylin before visualization on Olympus BX60 microscope. 8-10 pictures of each slide were taken for analysis, depending on the sample size. Colorimetric intensities of IHC-stained antigen spots were counted using a computer-assisted image analyzer (Olympus Microimage Image Analysis V4.0 software for Windows). The intensities of color related to CD45 antigen spot were expressed as mean pixel IOD.

T Cell Receptor β sequencing: Sorted T cells to be analyzed were centrifuged and washed in PBS, and genomic DNA was extracted using Wizard Genomic DNA purification kit (Promega). The quantity and purity of genomic DNA was assessed through spectrophotometric analysis using NanoDrop (ThermoScientific). Amplification of TCR genes was done within the lab using the ImmunoSEQ hsTCRB kit (Adaptive Biotechnologies Corp., Seattle, WA) according to the manual. Survey sequencing of TCRβ was performed by the Hollings Cancer Center Genomics Core using the Illumina MiSeq platform.

Statistical Analysis: Tumor area results were transformed using the natural logarithm for data analysis. Mixed effects linear regression models with a random component to account for the correlation of the repeated measure within a mouse were used to estimate tumor area over time. In circumstances where linearity assumptions were not met (FIGS. 3, 14), polynomial regression models were used (Laird and Ware, 1982). Linear combinations of the resulting model coefficients were used to construct estimates for the slope differences with 95% confidence intervals where applicable. For polynomial models, estimates were constructed for the differences in area between groups on the last day where at least one mouse was alive in all groups. As these experiments were exploratory, there was no estimation to base the effective sample size, therefore the animal studies used traditional sample sizes≥5. Experiments with multiple groups were analyzed using one-way analysis of variance (ANOVA) with post comparison of all pair wise groups using Tukey's range test. Experiments comparing two groups were analyzed using a Student's t test. The center values are the mean and error bars are calculated as the SEM. TCRβ sequencing analysis was based on the log-linear model and the 'relative risks' calculated with a 95% confidence interval.

Figures 22A, 22B, 22C, 22D, 22E, 22F, 22G:
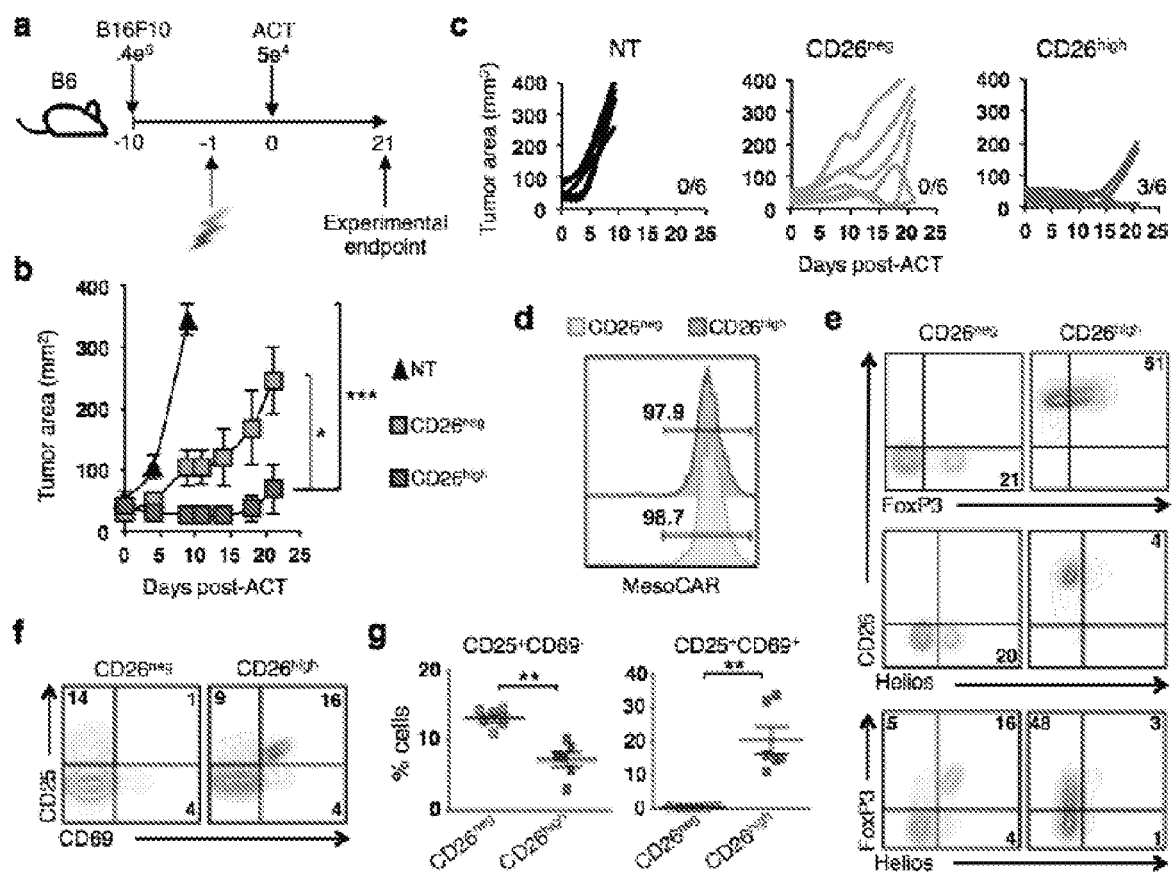

Example 3—Human CD26High T Cells Elicit Tumor Immunity Against Multiple Malignancies Via Enhanced Migration and Persistence CD26$^{high}$ T cells are activated and regress established tumors: CD26 is expressed on effector and memory, but not regulatory (Tregs), CD4$^+$ T cells (Ohnuma et al., 2008; Salgado et al., 2012). Yet, it remains unknown whether CD26 correlates with these opposing subsets in cancer therapy. To address this question, murine TRP-1 CD4$^+$ T cells, which express a transgenic TCR specific for tyrosinase on melanoma, were flow-sorted via CD26 expression. This strategy enriched CD4$^+$ T cells into two groups: CD26$^{neg}$ and CD26$^{high}$ Strikingly, a mere 50,000 CD26$^{high}$ T cells were more effective at clearing B16F10 melanoma tumor than 50,000 CD26$^{neg}$ T cells when infused into lymphodepleted mice (FIG. 22A-B). Moreover, half of the mice treated with CD26$^{high}$ T cells experienced a curative response (FIG. 22C).

Figures 15A, 15B, 15C, 15D, 15E, 15F, 15G:
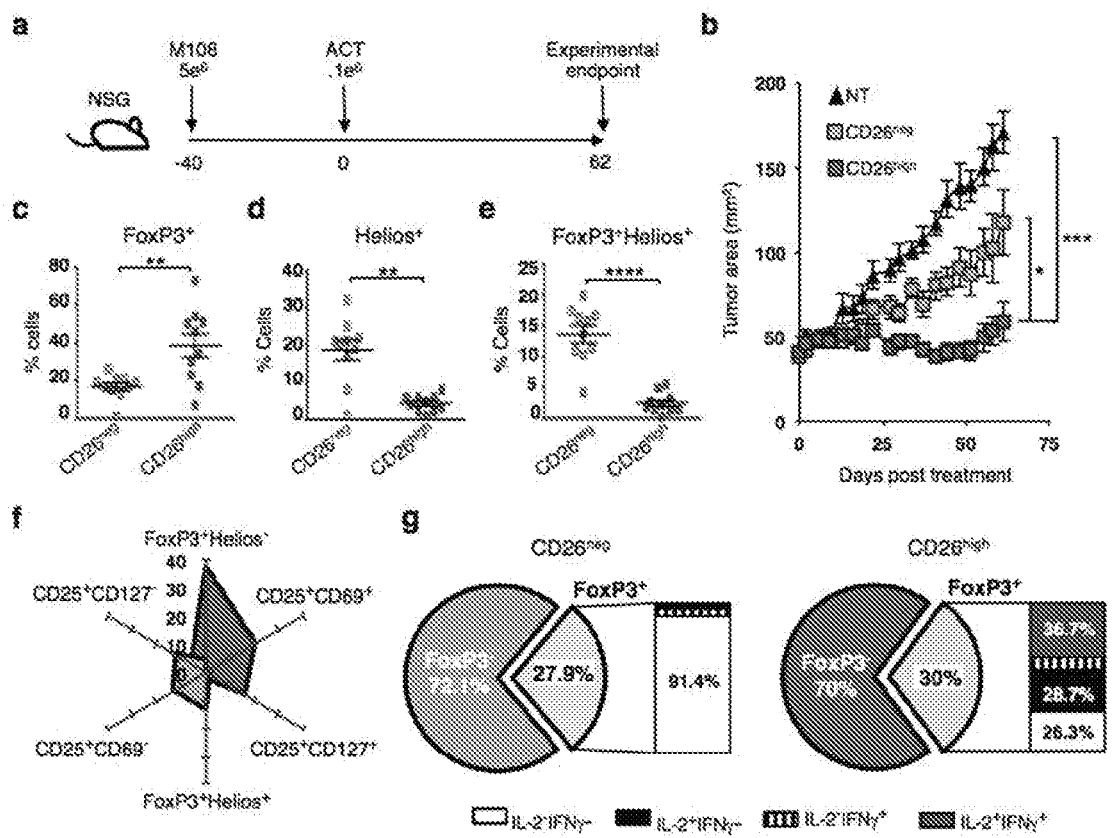

The antitumor activity of human CD26$^{high}$ T cells in a CAR-T model was determined next. To do this, the strategy depicted in FIG. 15A was used. First, CD4$^+$ T cells were isolated from the peripheral blood of a healthy individual and then sorted by CD26 expression. Following bead activation, CD26$^{neg}$ and CD26$^{high}$ T cells were transduced to express a chimeric antigen receptor that targets mesothelin and signals CD3ζ (MesoCAR; ~98% CAR-specific; FIG. 22D). Similar to murine cells, human CD26$^{high}$ T cells ablated large, human mesothelioma tumors in NSG mice to a greater extent than CD26$^{neg}$ T cells (FIG. 15B). These findings show that both murine and human T cells that express high levels of CD26 can effectively regress solid tumors in vivo.

As FoxP3$^+$ Treg cells express nominal CD26[26], it was suspected that CD26$^{high}$ T cells exhibited greater antitumor activity because they were not suppressive (i.e. FoxP3$^{-/low}$). Surprisingly, CD26$^{high}$ T cells expressed more FoxP3 than CD26$^{neg}$ T cells (FIG. 15C). However, FoxP3$^+$CD26$^{high}$ T cells did not co-express Helios, a transcription factor expressed on thymus-derived Tregs (FIGS. 15D-E; 22E). Given that human T cells upregulate FoxP3 following activation (Wang et al., 2007), it was posited that CD26$^{high}$ T cells express FoxP3 because they exist in an activated state post-enrichment, but prior to ex vivo bead activation. As expected, CD26$^{high}$ T cells had a ten-fold higher expression of the activation markers CD25 and CD69 (~20%) than CD26$^{neg}$ T cells (~2%) (FIGS. 15F-G). Also, CD26$^{neg}$ T cells displayed a higher frequency of CD25$^+$CD127$^-$ cells (CD26$^{neg}$~12%; CD26$^{high}$~5%), an extracellular phenotype associated with Tregs (Yu et al., 2012; Lie et al., 2006) (FIG. 15F). Finally, it was discovered that ~74% of FoxP3$^+$ CD26$^{high}$ T cells secreted the cytokines IL-2 and/or IFNγ (FIG. 15G). Conversely, <9% of CD26$^{neg}$ T cells were capable of cytokine production. Collectively, these data reveal that a portion of CD26$^{high}$ T cells are activated post-enrichment (prior to bead stimulation) and clear tumors when redirected with CAR. In contrast, CD26$^{neg}$ T cells are mainly suppressive and fail to regress tumors.

Figures 16A, 16B, 16C, 16D, 16E:
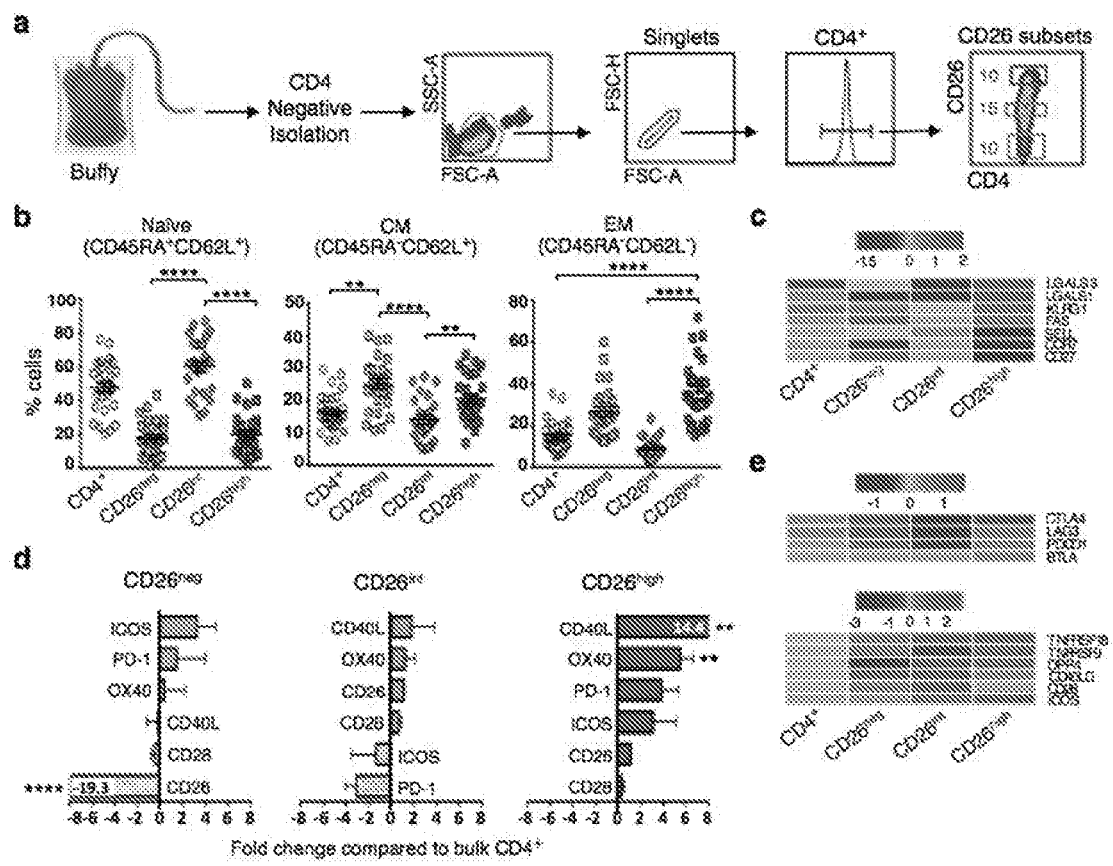

Naïve and memory CD4$^+$ T cells have variant CD26 expression: Although human CD26$^{high}$ T cells are more effective at clearing tumor than CD26$^{neg}$ cells, these cells are differentiated and might not be ideal for ACT. As CD26$^{int}$ cells have briefly been described as naïve (CCR7$^+$ CD45RA$^+$) (Bengsch et al., 2012), it was hypothesized that they would elicit superior antitumor immunity compared to CD26$^{neg}$ or CD26$^{high}$ T cells. To test this, a detailed characterization of their phenotype was first performed in vitro. CD4$^+$ T cells were enriched from healthy donors and FACS-sorted into bulk CD4$^+$, CD26$^{neg}$, CD26$^{int}$ or CD26$^{high}$ subsets (sorting purity>80%—FIGS. 16A and 23A). As expected, ~65% of CD26$^{int}$ cells were naïve (CD45RA$^+$ CD62L$^+$) while more than half of CD26$^{neg}$ and CD26$^{high}$ T cells possessed a more differentiated central or effector memory phenotype (FIGS. 16B and 23B). Gene array analysis corroborated the findings, showing both CD26$^{neg}$ and CD26$^{high}$ T cells expressed less CCR7, CD27 and CD62L than CD26$^{int}$ T cells (FIG. 16C). Furthermore, CD26$^{high}$ cells expressed heightened levels of markers associated with effector memory T cells (LGALS1, LGALS3) (Weng et al., 2012) as well as the senescence marker KLRG1 and FAS death ligand. Importantly, the differentiated phenotype of CD26$^{neg}$ and CD26$^{high}$ T cells and naïve characteristics of CD26$^{int}$ T cells were reproducibly observed in more than 25 healthy donors.

Given that CD26$^{int}$ cells are naive, it was posited that they would express less co-stimulatory and co-inhibitory receptors than CD26$^{neg}$ and CD26$^{high}$ T cells. As expected, CD26$^{int}$ T cells expressed less co-stimulatory and co-inhibitory markers than CD26$^{high}$ T cells (FIGS. 16D and 23C). Conversely, CD26$^{high}$ T cells expressed more PD-1, CD40L and OX40 than the other subsets while ICOS and PD-1 were the most prevalent markers on CD26$^{neg}$. Furthermore, gene array analysis revealed an upregulation of CTLA4, Lag3 and PDCD1 in both CD26$^{neg}$ and CD26$^{high}$ T cells compared to CD26$^{int}$ (FIG. 16E top). Despite the increased co-inhibitory markers on CD26$^{high}$ T cells, they also expressed many co-stimulatory markers, including CD40L (CD40LG), 41BB (TNFRSF9) and GITR (TNFRSF18) (FIG. 16E bottom). Overall, these findings revealed that CD26$^{int}$ T cells possess a naïve phenotype and express less co-stimulatory/inhibitory receptors compared to CD26$^{neg}$ and CD26$^{high}$ T cells.

Figures 17A, 17B, 17C, 17D, 17E:
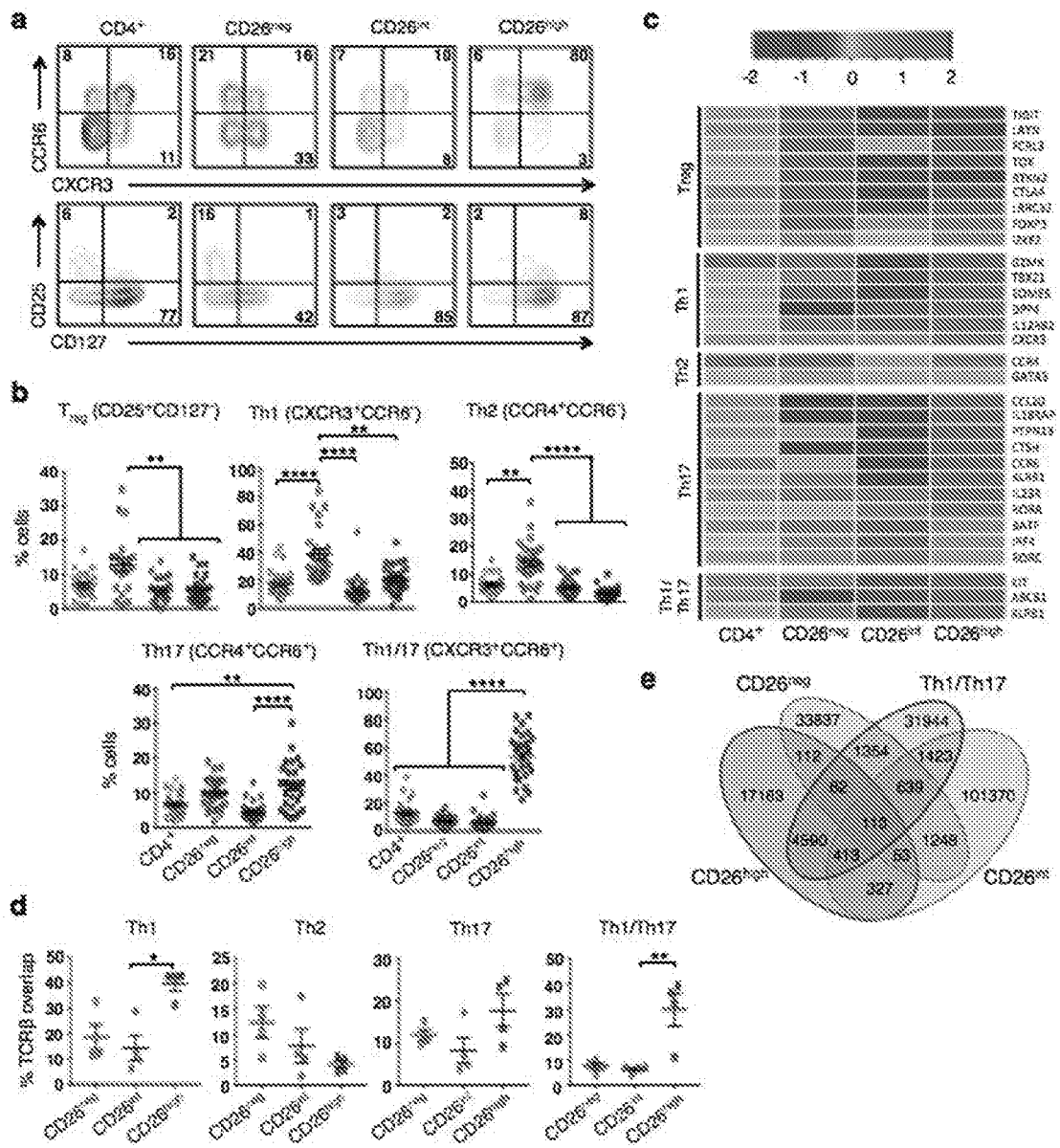
Figures 24A, 24B, 24C, 24D, 24E:
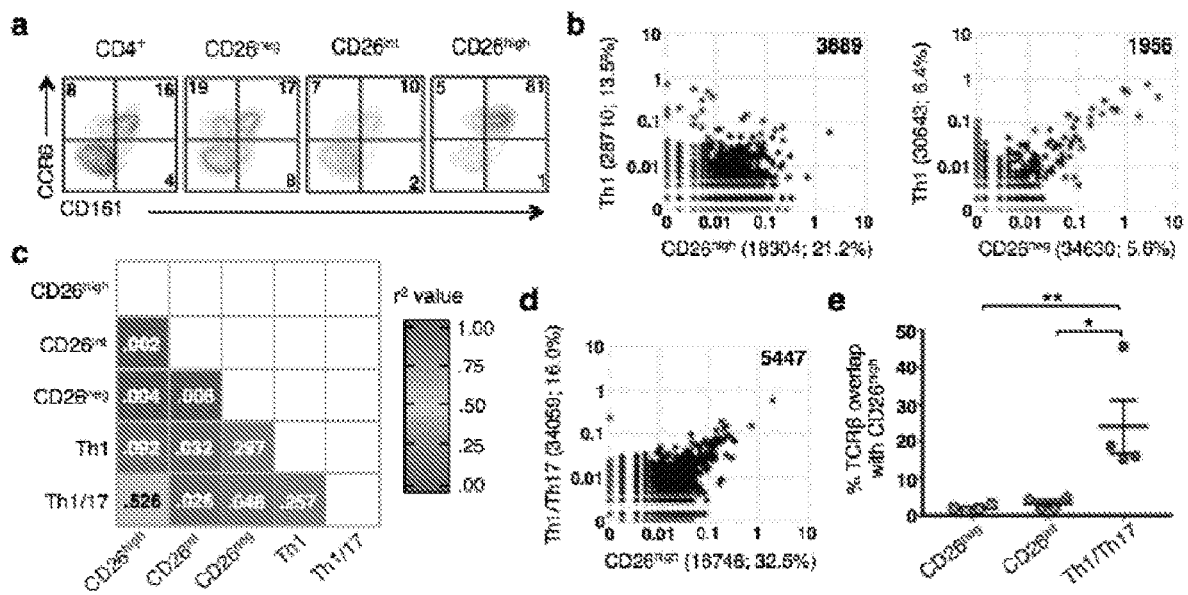

CD26 expression correlates with specific CD4$^+$ T cell subsets: Although CD26$^{neg}$ T cells contain a Treg population (Salgado et al., 2012) and CD26$^{high}$ cells have been published to exhibit a Th1$^{32}$ or Th17$^{30}$ phenotype, CD26$^{int}$ cells have not yet been characterized. Given that CD26$^{int}$ T cells appear naïve, it was hypothesized that they would not express the chemokine receptors indicative of any particular subset while CD26$^{neg}$ and CD26$^{high}$ T cells would exhibit their reported Treg and Th1/Th17 phenotypes. As expected, CD26$^{high}$ T cells were composed of Th1 (CXCR3$^+$CCR6$^-$) and Th17 (CCR4$^+$CCR6$^+$) cells, with the majority being hybrid Th1/Th17 (CXCR3$^+$CCR6$^+$) cells (FIGS. 17A-B). These cells also exhibited heightened levels of CD161, which has recently been identified as a marker for long-lived antigen-specific memory T cells (Alsuliman et al., 2017) (FIG. 24A). It was also identified Th1, Treg (CD25$^+$ CD127$^-$) and Th2 (CCR4$^+$CCR6$^-$) populations in the CD26$^{neg}$ subset. On the contrary and as expected, CD26$^{int}$ cultures were comprised of lower frequencies of helper memory subsets. As shown in FIG. 17C, gene array analysis confirmed that CD26$^{neg}$ cells expressed a Treg (i.e. TIGIT, TOX, CTLA4), Th1 (i.e., EOMES, GZMK, IL12RB2) and Th2 (CCR4, GATA3) signature. Conversely, CD26$^{high}$ T cells had high gene expression in the Th1 (i.e., GZMK, TBX21, EOMES), Th17 (i.e., CCL20, IL18RAP, PTPN13) and Th1/Th17 (KIT, ABCB1, KLRB1) subsets. As expected, the subset-defining genes in CD26$^{int}$ T cells were sparse. Collectively, these findings confirm that CD26$^{int}$ T cells are naïve and not yet committed to any subsets.

Helper T cell subsets express a specific T cell receptor β (TCRβ) profile. Using TCRβ analysis, it was found that many TCRs in CD26$^{high}$ T cells overlap with Th1, Th17 and Th1/Th17 cells, but not with Th2 cells (FIG. 17D). While CD26$^{high}$ T cells had greater overlap with Th1 cells than CD26$^{neg}$ did, the overlapping TCRs between Th1 and CD26$^{neg}$ were more highly expressed (FIG. 24B). This heightened TCRβ expression revealed a correlation between CD26$^{neg}$ and Th1 cells ($r^2$=0.297), as well as CD26$^{high}$ and Th1/Th17 cells ($r^2$=0.526; FIG. 24C), thereby confirming the previous findings. Although CD26$^{high}$ T cells exhibited significant overlap with Th1/Th17 cells, they shared little TCRβ overlap with CD26$^{neg}$ or CD26$^{int}$ cells (FIGS. 17E; 24D-E). Likewise, CD26$^{int}$ cells had minimal TCRβ overlap with any of the Th subsets. Overall, these data confirmed that CD26$^{high}$ and CD26$^{neg}$ T cells are differentiated cells that contain multiple cell subsets while CD26$^{int}$ T cells are primarily uncommitted.

Figures 18A, 18B, 18C, 18D, 18E:
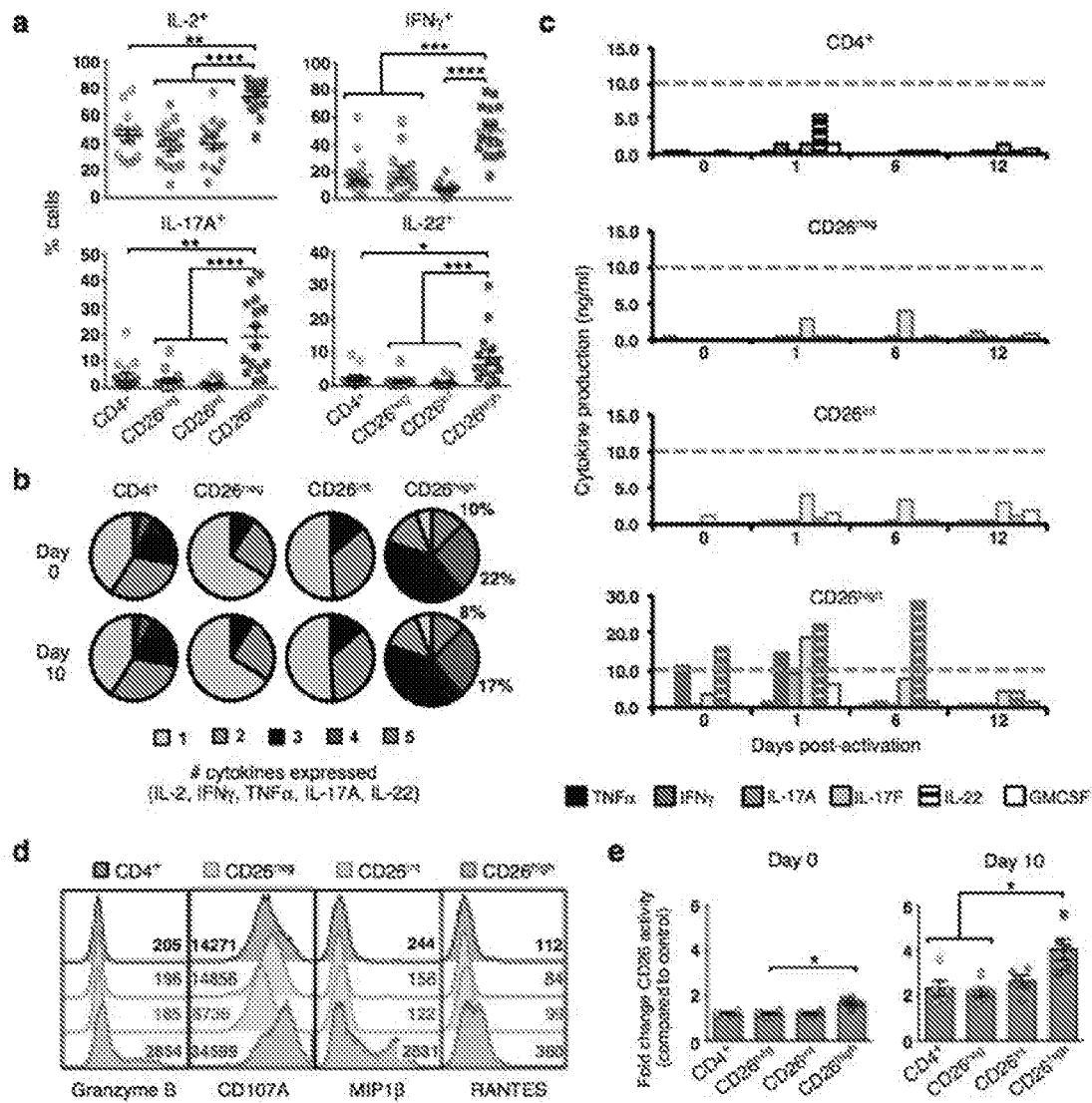
Figures 25A, 25B, 25C, 25D, 25E, 25F:
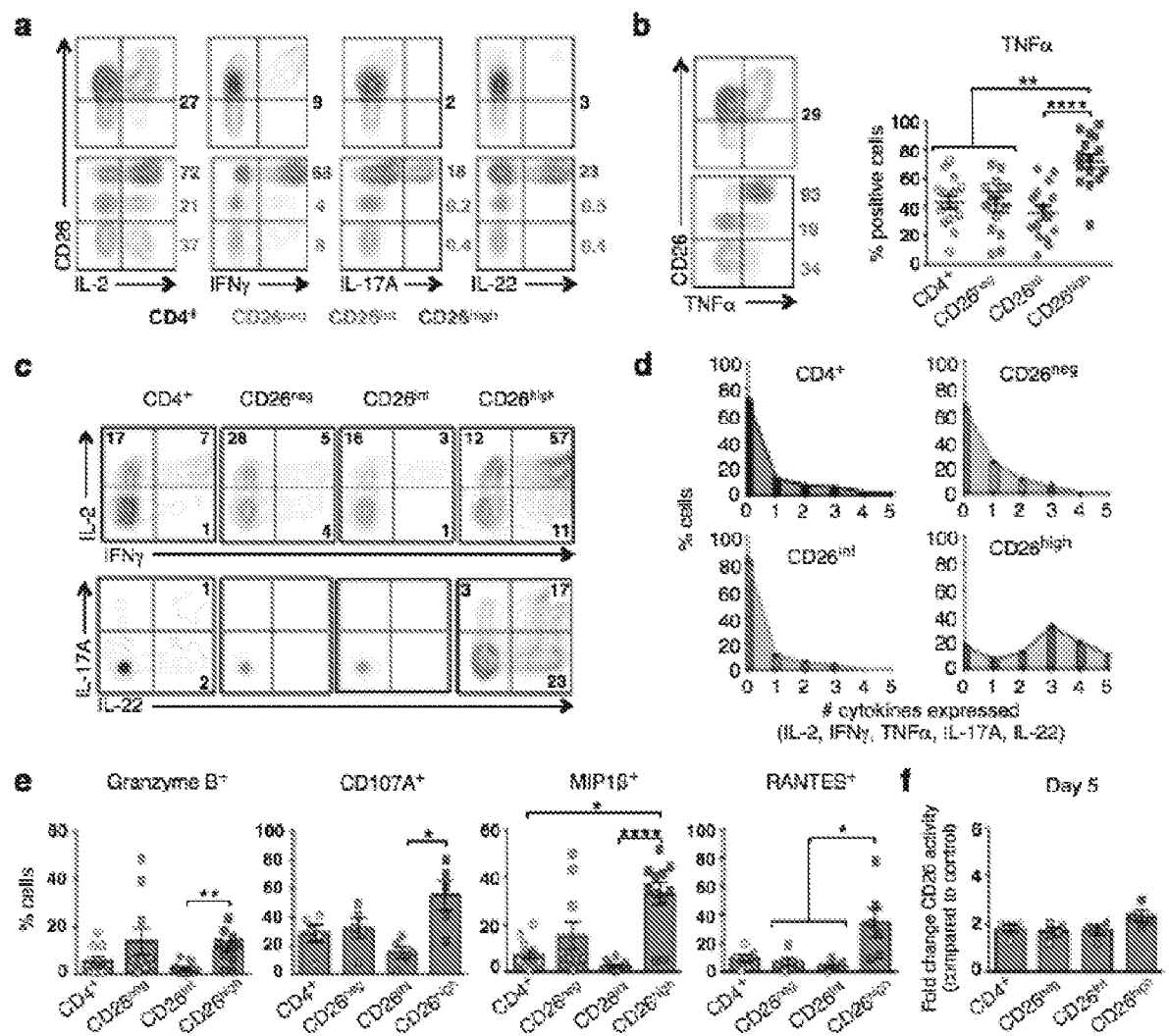

CD26$^{high}$ cells are multi-functional and enzymatically active: Given that CD26$^{neg}$ and CD26$^{high}$ T cells are differentiated, it was hypothesized that they would secrete more cytokines than naïve CD26$^{int}$ in vitro. Interestingly, CD26$^{high}$ T cells had heightened production of multiple cytokines, including IL-2, IFNγ, IL-17A, IL-22 and TNFα (FIG. 18A; 25A-B). However, this heightened cytokine profile did not directly correlate with cell differentiation, as evidenced by similar cytokine production between bulk CD4$^+$, CD26$^{neg}$ and CD26$^{int}$ T cells. Given the numerous cytokines produced by CD26$^{high}$ T cells, their capacity to secrete multiple cytokines at once (i.e., multi-functionality) was next investigated. Strikingly, CD26$^{high}$ T cells were highly multi-functional (FIG. 25C) with roughly 25% of these cells producing 4-5 cytokines simultaneously (FIG. 18B), a phenomena not seen in the other subsets. When the percentage of these donors not producing any cytokines was taken into account, it was discovered that 60-80% of CD4$^+$, CD26$^{neg}$ and CD26$^{int}$ T cells were incapable of producing cytokines on day 0, while the majority of CD26$^{high}$ T cells produced 3-5 cytokine simultaneously (FIG. 25D). This vast cytokine production was maintained in CD26$^{high}$ T cells throughout culture (FIG. 25C). Furthermore, CD26$^{high}$ T cells produced more cytotoxic granules (Granzyme B, CD107A) and chemokines (MIP1β, RANTES) compared to other subsets, a property normally used to define cytotoxic CD8$^+$ T cells (FIGS. 18D and 25).

As CD26 enzymatic activity plays a minor role in supporting T cell function (Fan et al., 2003), it was next posited that enzymatic activity would be elevated in CD26$^{high}$ T cells compared to the other subsets. Indeed, throughout a 10 day expansion in vitro, CD26$^{high}$ T cells maintained the highest enzymatic activity (FIGS. 18E and 25F). Thus, CD26$^{high}$ T cells are uniquely multi-functional, cytotoxic and enzymatically active.

Figures 26A, 26B, 26C, 26D, 26E, 26F, 26G, 26H, 26I, 26J:
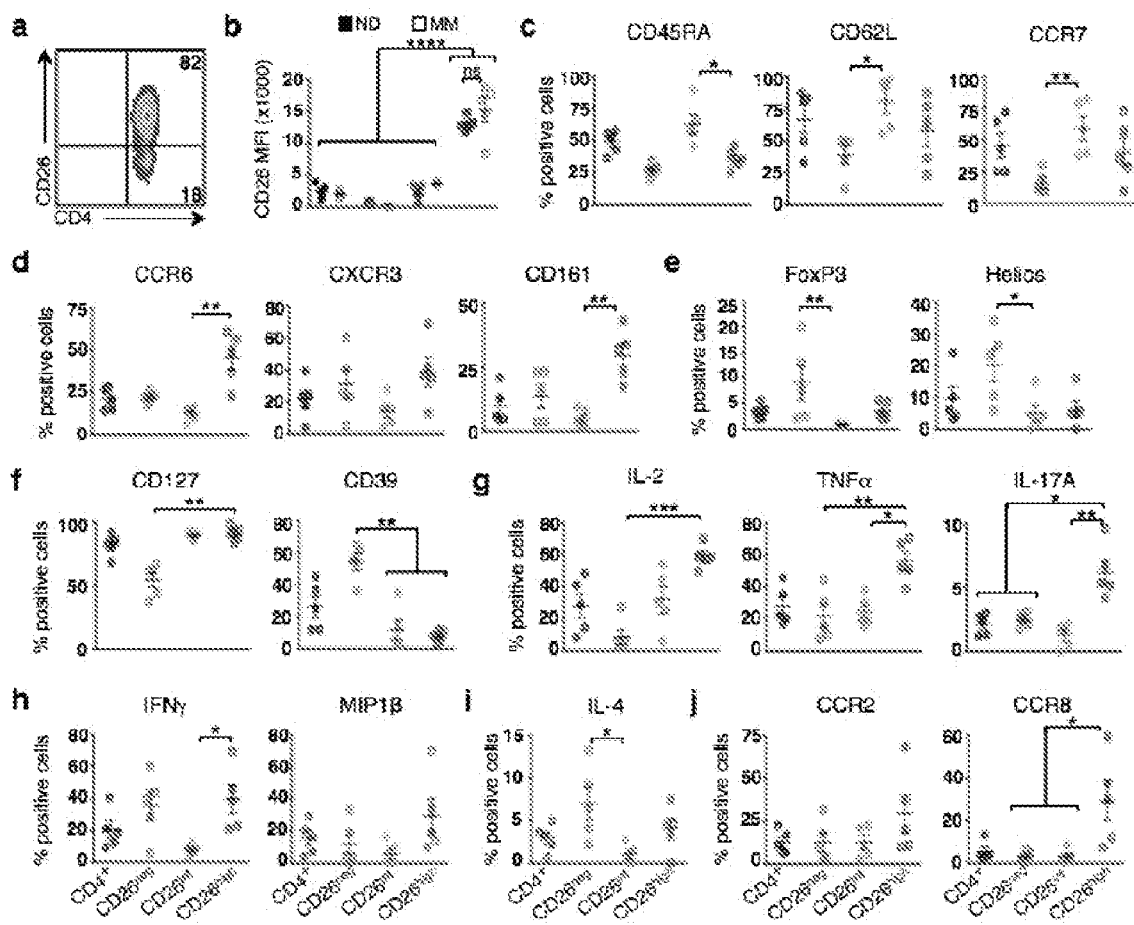

CD26 negative, intermediate and high T cells exist in cancer patients: While CD4$^+$ T cells with distinct CD26 expression profiles exhibit unique immunological properties in healthy donors, it was unclear if these biological assets are similar in cancer patients. To address this question, T cells with high, intermediate or low CD26 expression were isolated from the blood of patients with malignant melanoma and their function, phenotype and memory profile were examined. CD26 was distributed similarly on CD4$^+$ T cells from melanoma patients (FIG. 26A) as in normal donors (FIG. 16A). Furthermore, the mean fluorescence intensity (MFI) of CD26 on all subsets was similar between cancer patients and healthy individuals, with CD26$^{high}$ T cells maintaining the greatest CD26 expression (FIG. 26B). The phenotype of CD26$^{neg}$, CD26$^{int}$ and CD26$^{high}$ T cells in melanoma patients were similar to that seen in health donors. For example, CD26$^{int}$ T cells were naïve, denoted by high CD45RA, CD62L and CCR7 markers (FIG. 26C). CD26$^{high}$ T cells expressed Th1/Th17 chemokine receptors (CCR6, CXCR3 and CD161) while CD26$^{neg}$ T cells expressed CXCR3, confirming that cell subsets within these cultures are comparable between cancer patients and healthy individuals (FIG. 26D). Finally, CD26$^{neg}$ T cells from cancer patients contained Tregs, as they expressed less CD127 but greater CD39, FoxP3 and Helios than the other subsets (FIG. 26E-F).

CD26$^{high}$ T cells also secreted more IL-2, TNFα, IL-17A, IFNγ and MIP-1β than other subsets following stimulation with PMA and Ionomycin (FIGS. 26G-H). CD26$^{neg}$ T cells from melanoma patients secreted elevated IL-4 (FIG. 26I), correlating with the previous finding that Th2 cells are prevalent in this culture (FIG. 17). Finally, CD26$^{high}$ T cells expressed more CCR2 and CCR8 than other subsets (FIG. 26J). As CCR8 promotes T cell trafficking to the skin, it was intriguing that this chemokine receptor was abundant on CD26$^{high}$ T cells from melanoma patients. Collectively, it was found that CD26$^{neg}$, CD26$^{int}$ and CD26$^{high}$ T cells from melanoma patients possess a similar biological profile as those identified in healthy donors.

Figures 19A, 19B, 19C, 19D, 19E, 19F, 19G, 19H, 19I:
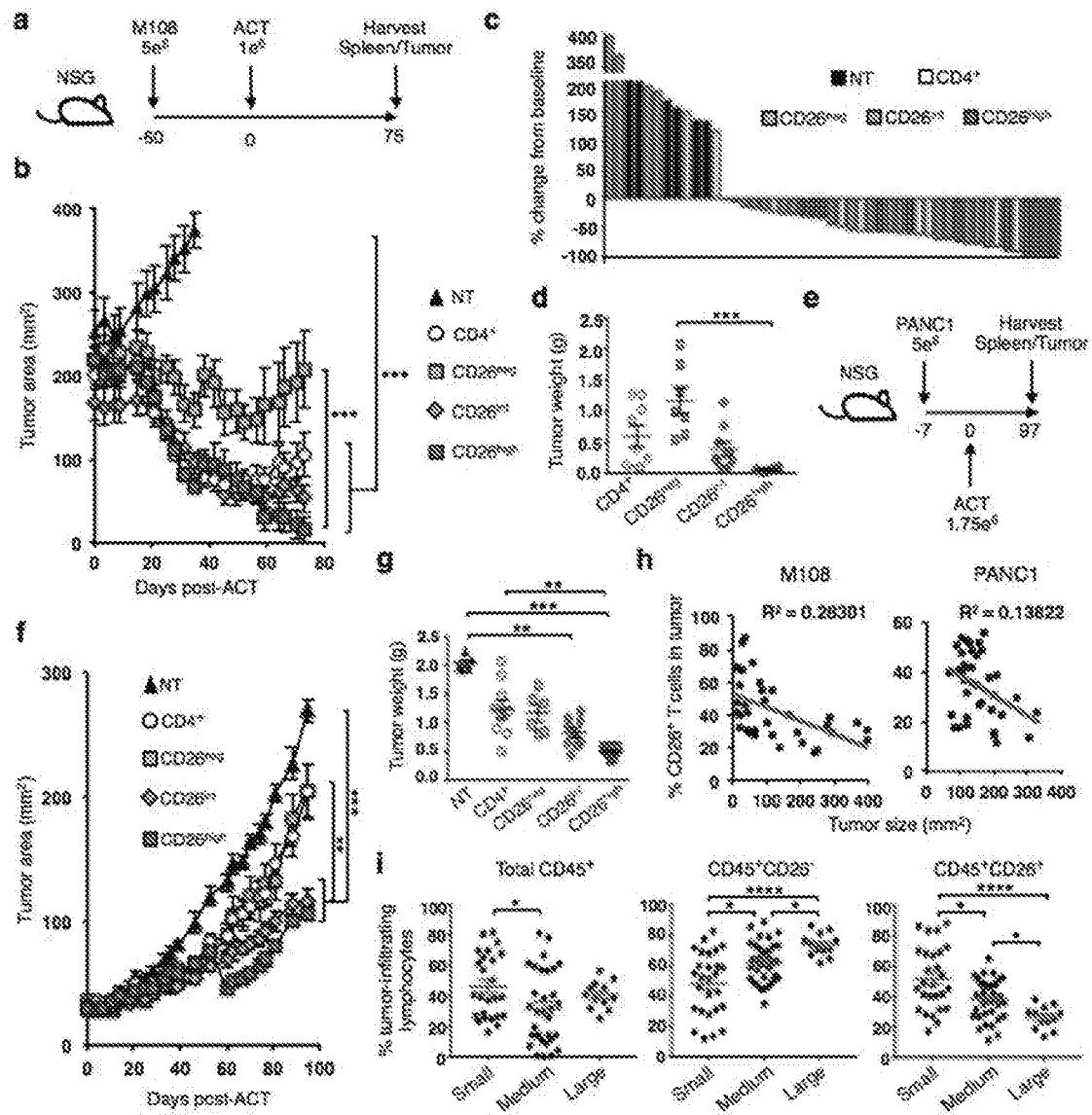
Figures 27A, 27B, 27C, 27D, 27E, 27F, 27G:
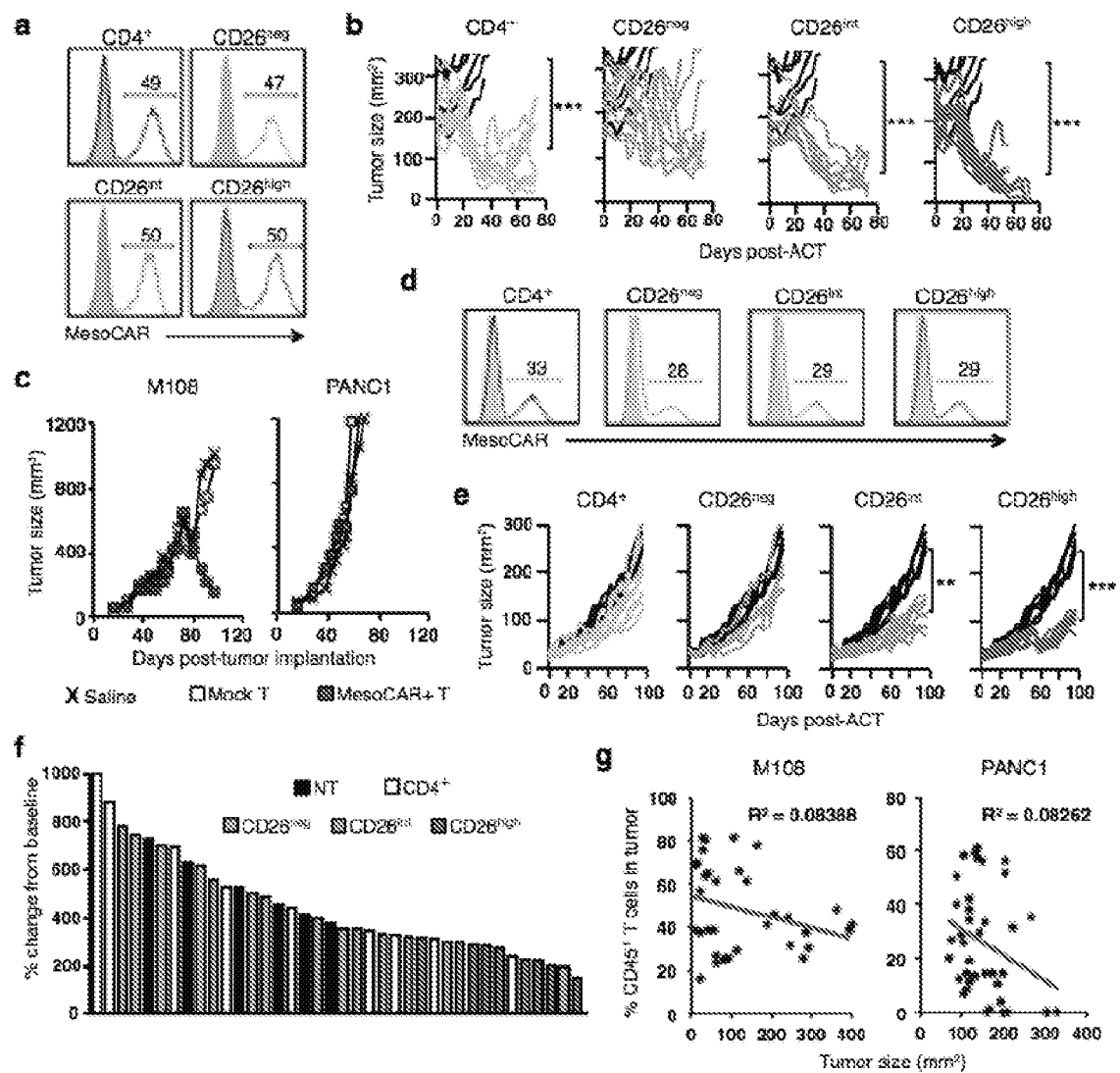

CD26$^{int}$ and CD26$^{high}$ T cells regress tumors in multiple cancer models: As enzymatically active CD26$^{high}$ T cells are more differentiated than CD26$^{int}$ T cells, it was hypothesized that CAR$^+$CD26$^{int}$ T cells would clear tumor and persist better than CAR$^+$CD26$^{high}$ T cells. To address this hypothesis, human CD4$^+$, CD26$^{neg}$, CD26$^{int}$ and CD26$^{high}$ T cells were redirected to recognize mesothelin on M108 tumor via a MesoCAR (FIG. 11A). Ten days post-expansion, CAR-T cells were infused into NSG mice bearing large M108 mesothelioma (FIG. 19A). Surprisingly, despite the seemingly exhausted phenotype of CD26$^{high}$ T cells, they regressed tumor slightly, but not significantly, better than CD26$^{int}$ T cells (FIGS. 19B and 27B). CD4$^+$ T cells were only slightly less effective than CD26$^{int}$ or CD26$^{high}$, while CD26$^{neg}$ T cells proved to be incapable of regressing mesothelioma. The tumor curve data in FIG. 19B directly correlated with both percent tumor change from baseline (FIG. 19C) and tumor weights (FIG. 19D). Collectively, it was found that CAR$^+$ T cells that express CD26 are more effective at clearing tumors.

Figures 20A, 20B, 20C, 20D, 20E, 20F, 20G, 20H, 20I, 20J:
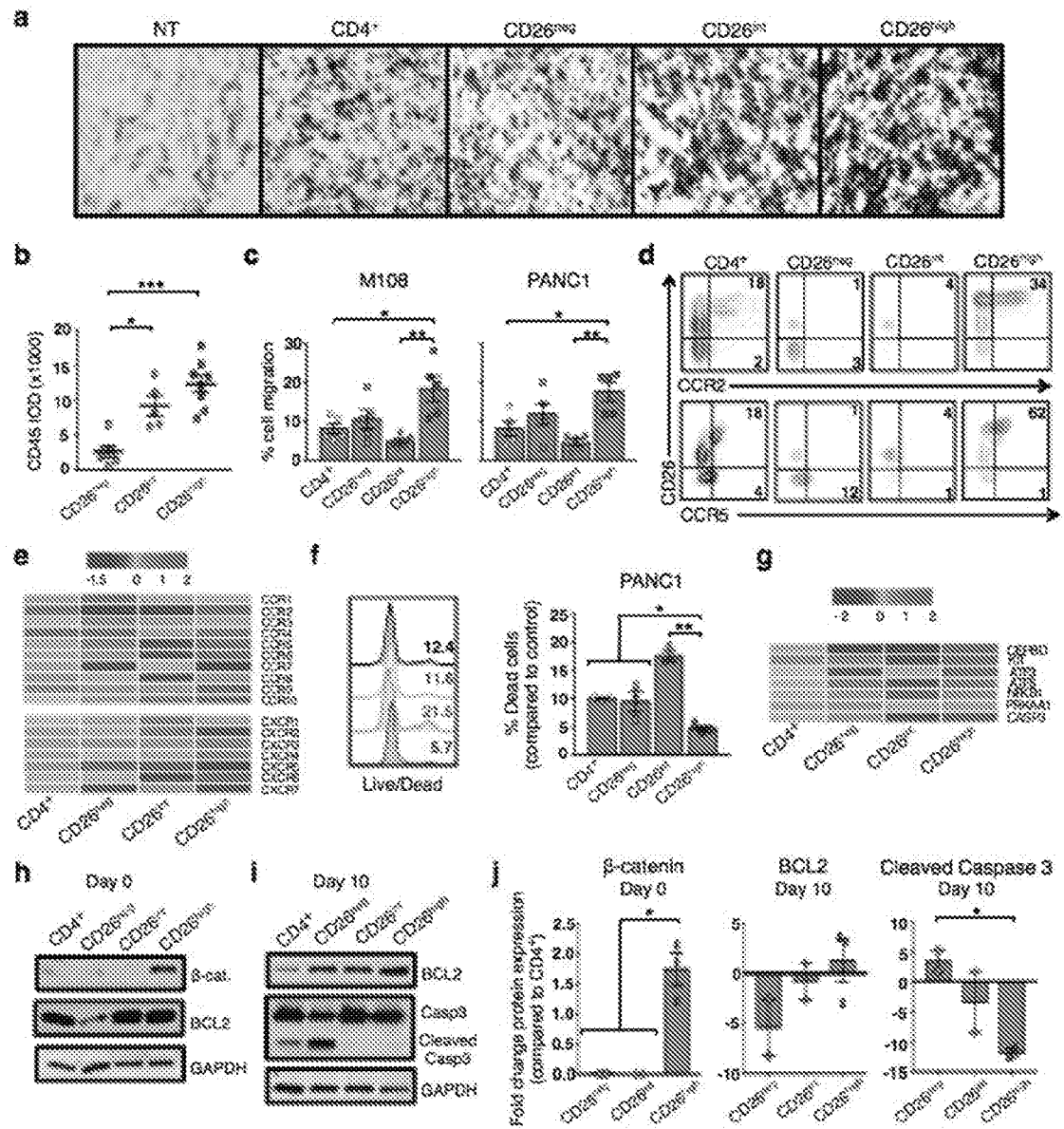

In contrast to human mesothelioma mouse models, CAR-T therapy does not regress pancreatic tumors (FIG. 20C). Thus, it was next sought to determine if CAR-T cells that express CD26 (CD26$^{high}$ and CD26$^{int}$) could regress pancreatic cancer (PANC1) in mice to a greater extent than CD26$^{neg}$ T cells. To test this, a similar treatment strategy (FIG. 19E) was used as performed in the M108 model. Following CAR transduction (FIG. 27D), both CD26$^{int}$ and CD26$^{high}$ T cells significantly regressed pancreatic tumors while bulk CD4$^+$ and CD26$^{neg}$ T cells yielded little-to-no antitumor response (FIGS. 19F and 27E). These findings were confirmed by decreased tumor growth and weight in mice treated with CD26$^{int}$ or CD26$^{high}$ T cells compared to mice treated with CD4$^+$ or CD26$^{neg}$ T cells (FIGS. 19G and 27F). Overall, these data demonstrate that differentiated CD26$^{high}$ T cells exhibit a similar antitumor response as naïve CD26$^{int}$ T cells.

Given that CD26$^{int}$ and CD26$^{high}$ T cells yielded the best antitumor response, it was next posited that CD26 expression on T cells in the tumor itself might correlate with overall response. To test this, tumor-infiltrating lymphocytes were isolated from all mice at experimental endpoint and assessed donor cell persistence and phenotype by flow cytometry. Unexpectedly, it was found that there was merely a weak correlation between total CD45$^+$ donor T cell persistence and overall response (FIG. 27G). On the contrary, a stronger correlation was found between the percentages of CD26$^+$ donor T cells to overall response (FIG. 19H). When graphed by tumor size (small>100 mm$^2$, medium=100-200 mm$^2$, large>200 mm$^2$), it was confirmed that the total percentage of CD45$^+$ T cells was similar between the groups but that CD26 expression on TIL tightly correlated with antitumor response (FIG. 19I). These observations identify a direct correlation between CD26 expression on TIL and their subsequent ability to regress tumors.

CD26$^{high}$ T cells have enhanced migration and stemness: It was next sought to determine the mechanisms underlying the effectiveness of CD26$^{int}$ and CD26$^{high}$ T cells. Due to the multi-functional and cytotoxic nature of CD26$^{high}$ T cells (FIGS. 18 and 25), it was initially hypothesized that they would cause immediate tumor regression in mice, but would not persist liked CD26$^{int}$ lymphocytes. Surprisingly, CD26$^{high}$ T cells persisted as well as CD26$^{int}$ cells in the tumor (FIG. 728A). Conversely, few CD26$^{neg}$ T cells were detected. These findings were confirmed by immunohistochemistry, which revealed a direct correlation between CD26 and enhanced CD45$^+$ donor cell persistence in the tumor (FIG. 20A-B). Collectively, these findings revealed that CD26$^{int}$ and CD26$^{high}$ T cells persist in the tumor to a greater extent than bulk CD4$^+$ and CD26$^{neg}$ T cells.

Figures 28A, 28B, 28C, 28D, 28E, 28F:
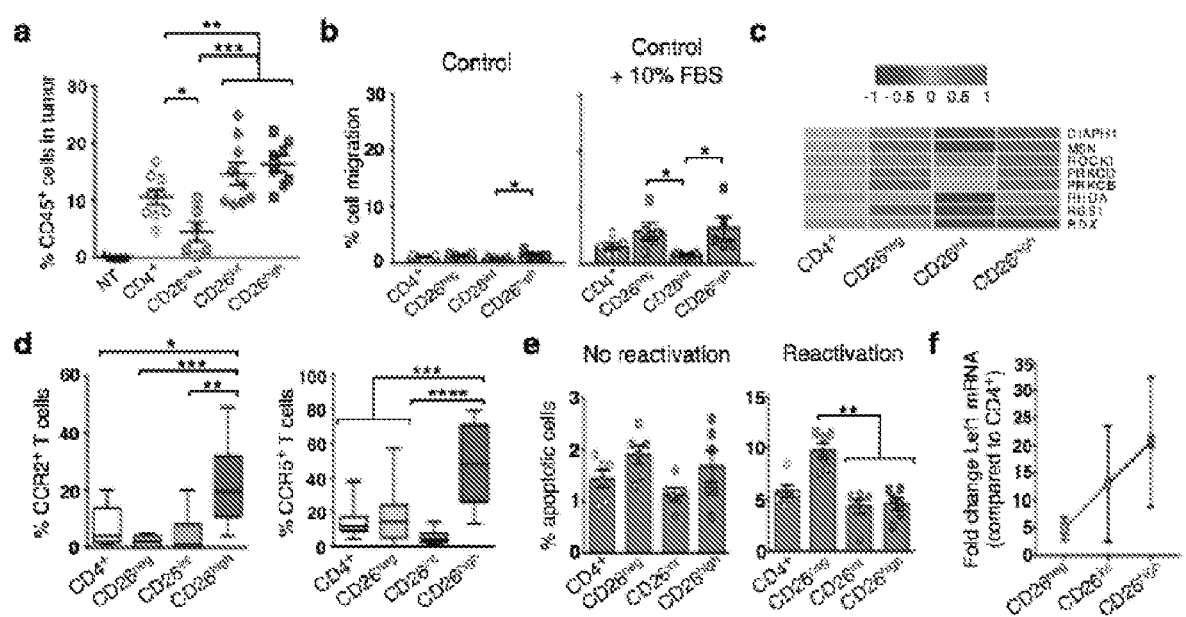

Given the ample amount of donor T cells persisting in the tumors of mice treated with CD26$^{int}$ and CD26$^{high}$ T cells, it was next sought to determine if they have an enhanced capacity to migrate. CD26$^{neg}$ and CD26$^{high}$ T cells migrated slightly better in control conditions than bulk CD4$^+$ and CD26$^{neg}$ T cells (FIG. 28B), perhaps due to the elevated expression of genes that aid in migration, including RGS1, RHOA, ROCK1 and DIAPH1 (FIG. 28C). Furthermore, it was discovered that CD26$^{high}$ T cells migrated to M108 and PANC1 in vitro to a greater extent than bulk CD4$^+$, CD26$^{neg}$ or CD26$^{int}$ T cells (FIG. 20C). Given that the chemokine receptors CCR2 and CCR5 have been shown to be important in migration towards mesothelioma tumors, the expression of these receptors on CD26$^{high}$ T cells was observed. Indeed, it was found that CD26$^{high}$ T cells not only expressed elevated levels of CCR2 and CCR5, but also expressed more CCR6, CXCR3, CXCR4 and CXCR6 than the other subsets (FIGS. 20D-E and 28D). Interestingly, the ligands for these chemokine receptors (CCL2, RANTES, CCL20, CXCL9-10, CXCL12 and CXCL16, respectively) are all produced by pancreatic tumors (Hedin, 2002). Additionally, CD26$^{high}$ T cells were more viable than the other subsets following migration towards pancreatic tumors (FIG. 6F).

Given this finding, it was tested if CD26$^{high}$ T cells were resistant to apoptosis. It was found that CD26$^{neg}$ T cells were more apoptotic than bulk CD4$^+$, CD26$^{int}$ and CD26$^{high}$ T cells (FIG. 28E). Conversely, CD26$^{high}$ T cells expressed many anti-apoptotic genes, such as KIT, CEBPD and ATF3 (FIG. 20G). Since Th17 cells have stemness and durable memory despite their differentiated appearance (Muransksi et al., 2011), it was next assessed if CD26$^{high}$ T cells expressed proteins in the Wnt/β-catenin pathway. Compared to naïve CD26$^{int}$ or regulatory CD26$^{neg}$ T cells, CD26$^{high}$ T cells had greater β-catenin expression (FIG. 20H) and maintained heightened BCL2 with minimal caspase 3 cleavage (FIG. 20I). These findings repeated among several healthy donors (FIG. 20J) and were confirmed by the upregulation of Lef1 concurrently with CD26 expression (FIG. 21F). Collectively, these findings reveal that CD26$^{high}$ T cells have remarkable self-renewal potential and a profound ability to migrate, survive and persist in the tumor long-term.

As visualized in FIG. 21, CD26 identifies three human CD4$^+$ T cell subsets with distinct immunological properties. First, CD26$^{neg}$ T cells exhibit poor persistence and antitumor activity due to increased Treg expression and lack of stemness properties. CD26$^{int}$ T cells are mainly naïve, persistent and effectively regress human tumors. Finally, CD26$^{high}$ T cells possess qualities of stemness and migration factors that support their persistence and antitumor activity in solid tumors.

Example 4—Materials and Methods

Mice and tumor lines: C57BL/6 (B6), TRP-1 TCR transgenic and NOD scid gamma (NSG) mice were purchased from The Jackson Laboratory and housed in the comparative medicine department at the Medical University of South Carolina Hollings Cancer Center (MUSC, Charleston, SC). NSG mice were housed in microisolator cages to ensure specific pathogen-free conditions and given ad libitum access to autoclaved food and acidified water. All housing and experiments were conducted in accordance with MUSC's Institutional Animal Care and Use Committee's (IACUC) procedures. B16F10 (H-2b) melanoma, M108 mesothelioma (gift, C. H. June) and PANC1 pancreatic cancer (gift, M. R. Rubinstein) cells were utilized for tumor experiments.

T cell subset isolation: Peripheral blood cells from healthy, de-identified individuals were purchased as a buffy coat (Plasma Consultants) or a leukophoresis (Research Blood Components). Lymphocytes were enriched via centrifugation with Lymphocyte Separation Media (Mediatech). Untouched CD4$^+$ T cells were isolated by magnetic bead separation (Dynabeads, Invitrogen) and cultured overnight in CM and rhIL-2 (100 IU/ml; NIH repository). The next morning, CD4$^+$ T cells were stained with PE-CD26 (C5A5b; BioLegend) and v500-CD4 (RPAT4) or APCCy7-CD4 (OKT4; BDPharmingen) and sorted on a BD FACSAria Ilu Cell Sorter into bulk CD4$^+$, CD26$^{neg}$, CD26$^{int}$ and CD26$^{high}$.

Following sort, cells were cultured overnight in CM, 100 IU/ml rhIL-2, 10 µg/ml Kanamycin/Ampicillin and 20 µg/ml anti-mycotic.

T cell expansion: TRP-1: Splenocytes from transgenic TRP-1 mice were isolated and cultured with 1 µl/ml TRP-1106-130 peptide (SGHNCGTCRPGWR-GAACNQKILTVR) and feeder T cells at a ratio of 1 feeder:5 TRP-1 CD4$^+$ T cells. Cells were programmed to a Th17 phenotype with polarizing cytokines (10 ng/ml hIL-1β, 100 ng/ml hIL-21, 100 ng/ml hIL-6, 30 ng/ml hTGFβ, 10 µg/ml αm-IFNγ, 10 µg/ml αm-IL-4) and 100 IU/ml IL-2 for six days. Human: Cells were cultured in CM supplemented with 100 IU/ml rhIL-2 at a 1:5 bead to T cell ratio using magnetic beads (Dynabeads, Life Technologies) decorated with antibodies to CD3 (OKT3) and ICOS (ISA-3, eBioscience), which were produced in the lab according to manufacturer's protocol. Cells were de-beaded on day four and culture media/100 IU/ml rhIL-2 was replaced as needed.

Flow Cytometry: Antibodies for extracellular stains were incubated with cells for 20 minutes in FACS buffer (PBS+ 2% FBS). For intracellular staining, cells were activated with PMA/Ionomycin for 1 hour, combined with Monensin (BioLegend) and incubated another 3 hours prior to staining in Fix and Perm buffers (BioLegend). For transcription factors, the FOXP3 kit (BioLegend) was used according to manufacturer's protocol. Live/dead staining was performed using the Zombie Aqua Fixable Viability Kit (BioLegend). Data were acquired on a BD FACSVerse (BD Biosciences) and analyzed using FlowJo software (Tree Star). A complete list of antibodies can be found in FIG. 29.

MicroArray: The Quiagen RNeasy Mini kit was used to isolate RNA from sorted CD4$^+$ T cells. Frozen RNA samples were sent to Phalanx Biotech Group for processing using their OneArray platform (San Diego, CA). NanoDrop ND-1000 was utilized to assess the quality and purity of the RNA. Absorbance ratios had a pass criteria of 260/280≥1.8 and A260/230≥1.5, indicating acceptable RNA purity. Agilent RNA 6000 Nano assay was used to ascertain RIN values, with a pass criteria of RIN value established at >6 indicating acceptable RNA integrity. Gel electrophoresis was used to evaluate gDNA contamination. Target preparation was performed using an Eberwine-based amplification method with Amino Allyl MessageAmp II aRNA Amplification Kit (AM1753, Ambion) to generate amino-allyl antisense RNA (aa-RNA). Prior to hybridization, labeled aRNA coupled with NHS-CyDye was prepared and purified. Purified coupled aRNA was quantified using NanoDrop ND-1000 with a pass criteria for CyDye incorporation efficiency at >15 dye molecular/1000 nt.

For data analysis, GPR files were loaded into Rosetta Resolver System. The Rosetta error model calculation was used to estimate random factors and systematic biases. Duplicate probes were averaged and median scaling was performed for normalization. Differentially expressed genes were defined as having a (+/−) log 2 fold change≥1 and p<0.05. Where log 2 ratios="NA", the differences in intensity between the two samples had to be ≥1000.

Heatmaps were constructed in R (version 3.1.2) using gplots (version 2.16.0) Log 2 values for bulk CD4$^+$ T cells were averaged and used as a baseline for the genes of interest. For each sample, the fold change relative to baseline was calculated and the median value for the triplicates was used for generating figures.

T Cell Receptor β Sequencing: CD4$^+$ cells were isolated from four individual healthy individuals and sorted into the following groups: bulk CD4$^+$, CD26$^{neg}$, CD26$^{int}$, CD26$^{high}$, Th1 (CXCR3$^+$CCR6$^-$), Th2 (CCR4$^+$CCR6$^-$), Th17 (CCR4$^+$ CCR6$^+$) and Th1/Th17 (CCR6$^+$CXCR3$^+$). Sorted subsets were then centrifuged and washed in PBS prior to extracting genomic DNA via Wizard Genomic DNA purification kit (Promega). Spectrophotometric analysis using NanoDrop (ThermoScientific) was used to assess the quantity and purity of genomic DNA. The ImmunoSEQ hsTCR kit (Adaptive Biotechnologies Corp, Seattle, WA) was used according to manufacturer's protocol to amplify the TCR genes. TCRβ sequencing was performed using the Illumina MiSeq platform at the Hollings Cancer Center Genomics Core. Analysis and graphing was performed using ImmunoSEQ software.

ELISA: T cells utilized for ELISA assays were plated at 0.2e$^6$ cells/200 µl CM for 12-15 hours prior to supernatant collection. Supernatant was then used to detect IL-17A, IL-17F, IL-22, GMCSF, IFNγ and TNFα by DuoSet ELISA kits (R&D) per manufacturer's instructions.

CD26 Enzymatic Assay: To determine CD26 enzymatic activity, a microplate-based fluorescence assay was performed. Briefly, 1e$^5$ T cells from days 0, 5 and 10 days post-activation were washed and re-suspended in 100 µl 4% gly-pro-P-nitroanalide in PBS. After two hours at 37° C., the release of pNA from the substrate was assessed using a Multiskan FC plate reader (ThermoScientific) at 405 nm.

Metastatic Melanoma Patients: Lymphocytes were enriched from peripheral blood drawn from de-identified metastatic melanoma patients. Cells were stained immediately for flow cytometry analysis or cryopreserved for future use. CD4$^+$ T cells from melanoma patients were sorted or gated by CD26 expression and compared to healthy donors in parallel experiments. All patients gave written, informed consent in accordance with the Declaration of Helsinki. The Medical University of South Carolina Institutional Review Board approved this study.

Adoptive Cell Transfer: B16F10: B6 mice were subcutaneously injected with 4e$^5$ B16F10 melanoma 10 days prior to adoptive cell transfer of 5e$^4$ CD4+Vβ14$^+$ CD26$^{neg}$ or CD26$^{high}$ T cells. Mice received nonmyeloablative 5Gy total body irradiation one day pre-ACT (N=6 mice/group, two independent experiments). M108: FIG. 15: NSG mice were subcutaneously injected with 5e$^6$ M108 mesothelioma (50% M108 in PBS, 50% Matrigel) 40 days prior to intravenous ACT of 1e$^5$ redirected MesoCAR$^+$ human CD26$^{neg}$ or CD26$^{high}$ T cells (N=10 mice/group). FIG. 19: 1e$^6$ Meso-CAR$^+$ CD4$^+$, CD26$^{neg}$, CD26$^{int}$ or CD26$^{high}$ T cells were infused into NSG mice bearing M108 tumors that were established for 60 days (N=7-9 mice/group). PANC1: NSG mice were subcutaneously injected with 5e$^6$ PANC1 cells (50% PANC1, 50% Matrigel) seven days prior to intravenous ACT of 1.75e$^6$ CD4$^+$, CD26$^{neg}$, CD26$^{int}$ or CD26$^{high}$ T cells (N=6-9 mice/group). All mice were measured and equally distributed among treatment groups based on tumor size. Tumors were measured bi-weekly by caliper in a blinded fashion until tumor end-point (>400 mm$^2$).

Immunohistochemistry: Cryosections of xenograft tumor tissues (5 µm thick) were incubated in −20° C. acetone for 10 minutes, rinsed and exposed to 0.3% hydrogen peroxide for 10 minutes before blocking and subsequent incubation with primary antibody (CD45, 2B11_PD7/26, 1:100; DAKO) overnight at 4° C. Slides were washed and incubated with secondary antibody (Polymer-HRP) and developed with DAB substrate kit (DAKO). Slides were counterstained with hematoxylin before visualization on an Olympus BX60 microscope. IHC-stained antigen spots were counted using a computer-assisted image analyzer (Olympus Microimage Image Analysis V4.0 software for Windows).

The intensities of color related to CD45 antigen spot were expressed as mean pixel IOD.

Transwell Migration Assay: Sorted human T cells ($7.5e^4$) were resuspended in 75 µl RPMI+0.1% FBS and placed in the top well of a transwell plate. Chemoattractants (235 µl) were placed in the bottom well as follows: control media (RPMI+0.1% FBS), RPMI+10% FBS, M108 supernatant or PANC1 supernatant. Supernatant from cancer cells was collected 15 hours after plating. The ability of subsets to migrate at 37° C. for two hours was assayed by flow cytometry.

Western Blot: Protein was isolated and concentration quantified using a BSA Protein Assay Kit (ThermoScientific). Ten-20 µg of total protein was separated on a Mini-PROTEAN TGX, Any kD™ gel followed by transfer onto PVDF membranes (Bio-Rad). The membranes were blocked (5% non-fat dry milk in TBS+0.5% Tween20) prior to overnight incubation at 4° C. with primary antibodies to β-catenin (BD), Bcl-2 (D17C4), Caspase-3 (8G10), or GAPDH (D16HH, Cell Signaling). Following washes, membranes were incubated for 1 h at room temperature with secondary HRP-conjugated goat antibodies to mouse or rabbit IgG (Cell Signaling). Chemiluminescence was performed using Western ECL Blotting Substrate (Bio-Rad) followed by X-ray film-based imaging. Films were scanned and quantified for integrated optical density (IOD) using ImageJ software. To remove antibodies, membranes were incubated for 15 min at room temperature in Restore Western Blot Stripping Buffer (ThermoScientific).

Statistical Analysis: Experiments comparing two groups were analyzed using a Mann-Whitney U Test. For multi-group comparison, a one-way analysis of variance (ANOVA) was performed with a post comparison of group using Kruskal-Wallis. Graphs utilizing error bars display the center values as the mean and error bars indicate SEM. TCRβ sequencing analysis was based on the log-linear model and the relative risks were calculated with a 95% confidence interval. For tumor curves, Mann-Whitney or Kruskal-Wallis tests were performed at the final dates where all mice from compared groups were still alive. As these experiments were exploratory, there was no estimation to base the effective sample size; therefore, the animal studies were based on using traditional sample sizes≥6.

Example 5—Further Characterization of $CD26^{high}$ T Cells

Figures 31A, 31B, 31C, 31D:
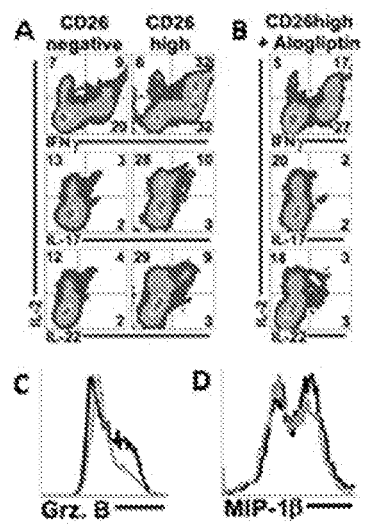

In further studies, it was found that the $CD26^{high}$ T cells are enzymatic and can be inhibited by treatment with Alogliptin (FIGS. 30A, 30B). The $CD26^{high}$ T cells also have memory stem cell properties and CD26-enzyme inhibition converts the cells to a regulatory phenotype (FIGS. 30C-30D). Intriguingly, the enhanced function of $CD4^+$ $CD26^{high}$ cells was reduced by treatment with the CD26 enzymatic inhibitor, Alogliptin (FIGS. 31A-31B). Along with the reduction of the aforementioned cytokines, $CD4^+$ $CD26^{high}$ cells also secreted less Granzyme B (cytotoxin) and MIP-1β (chemokine; affects T cell migration) (FIGS. 31B-31D).

Thus, the enzymatic activity of CD26 may have a role on the function, migration and cytotoxicity of $CD4^+CD26^{high}$ T cells in the tumor microenvironment. Furthermore, the enzymatic activity of these cells may be used to further enhance the efficacy of ACT treatment (i.e., enzymatic stimulation via exogenous chemokines).

Figure 32A:
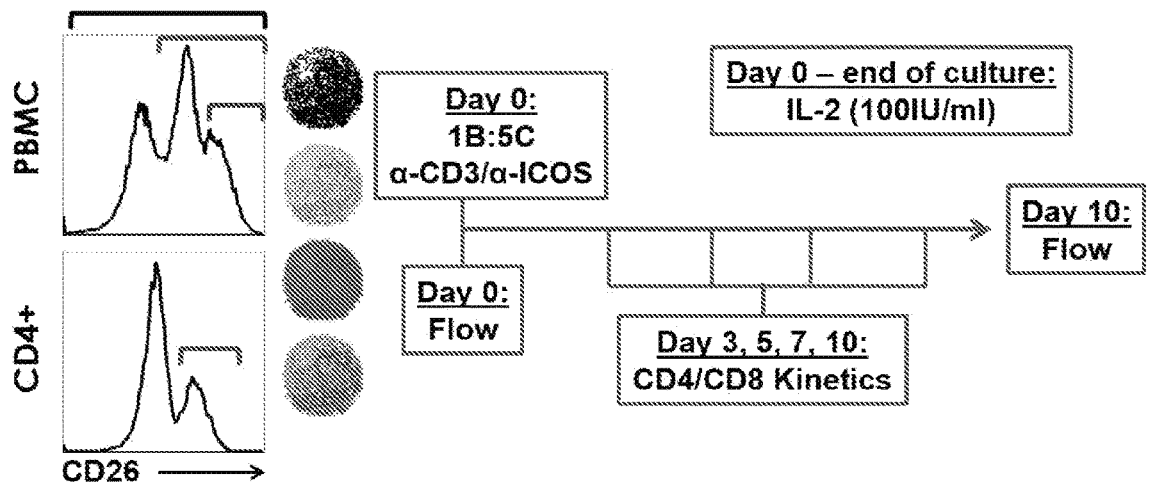
Figure 32B:
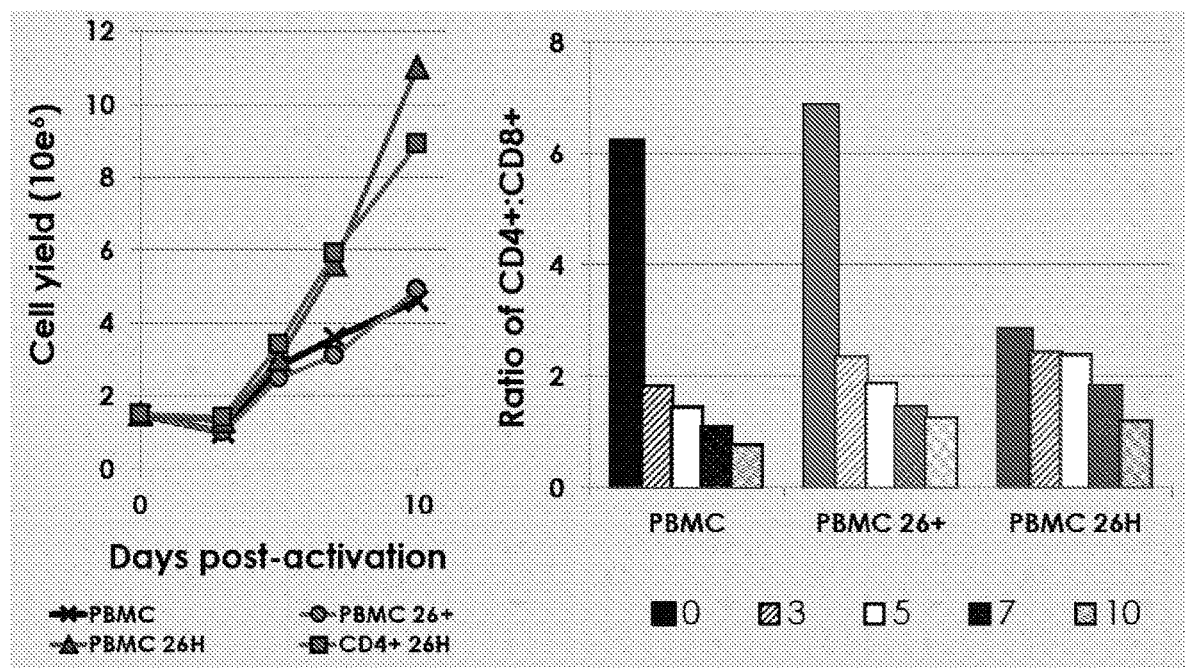
Figure 32C:
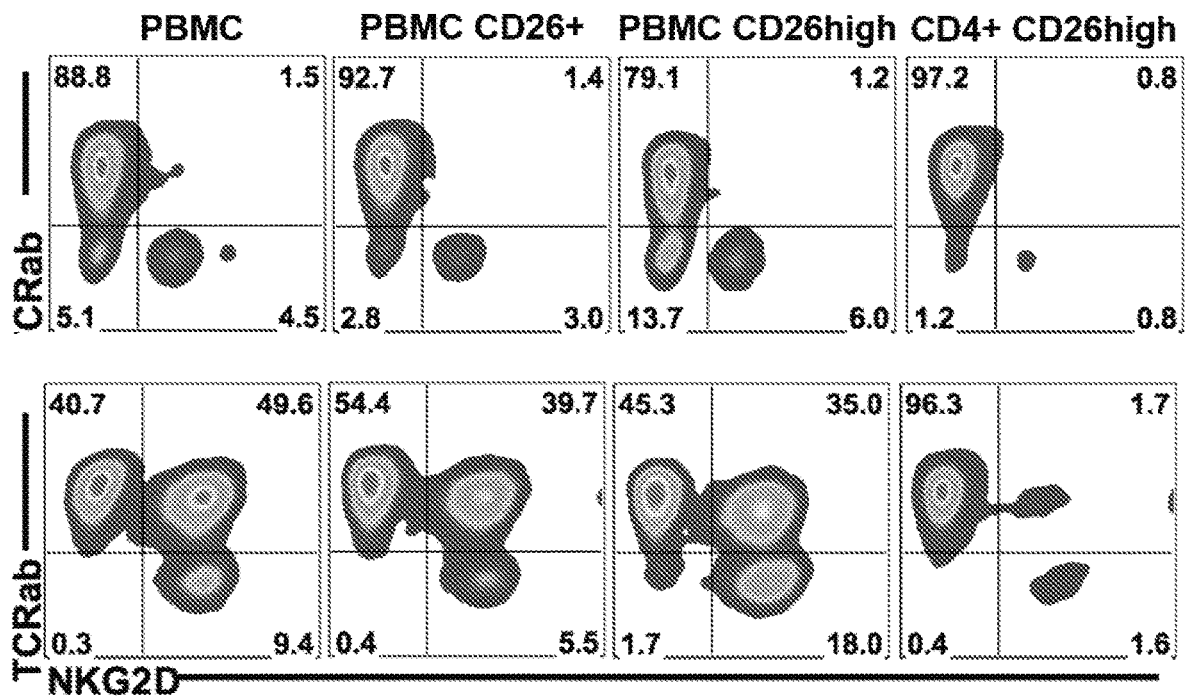
Figure 32D:
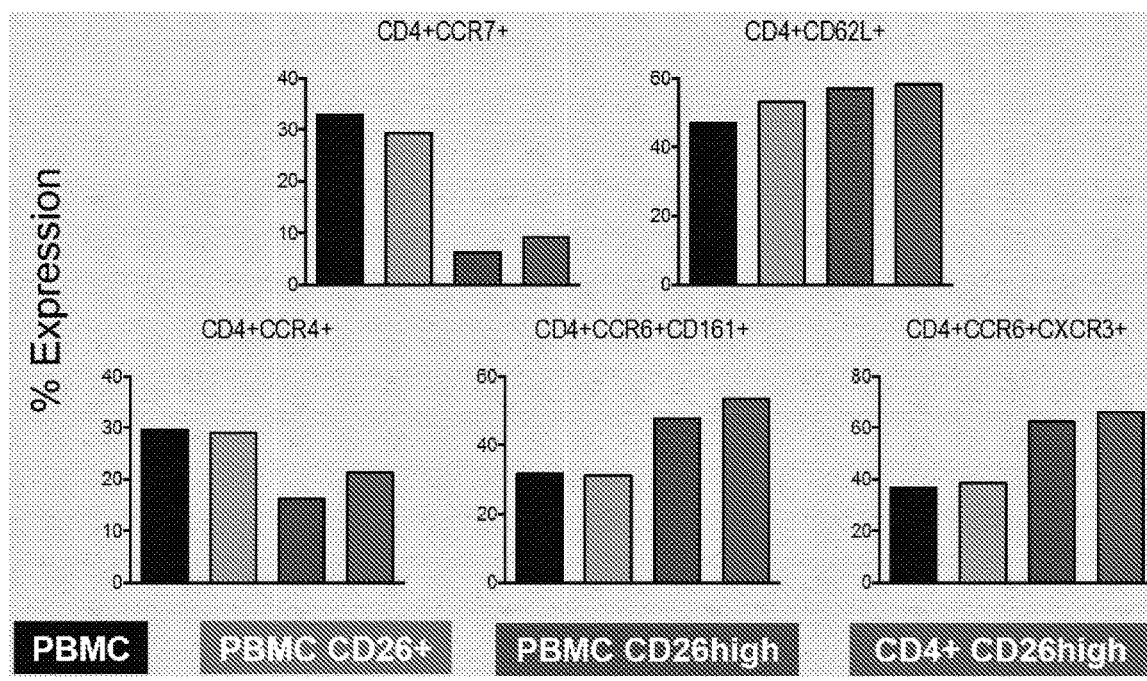
Figure 32E:
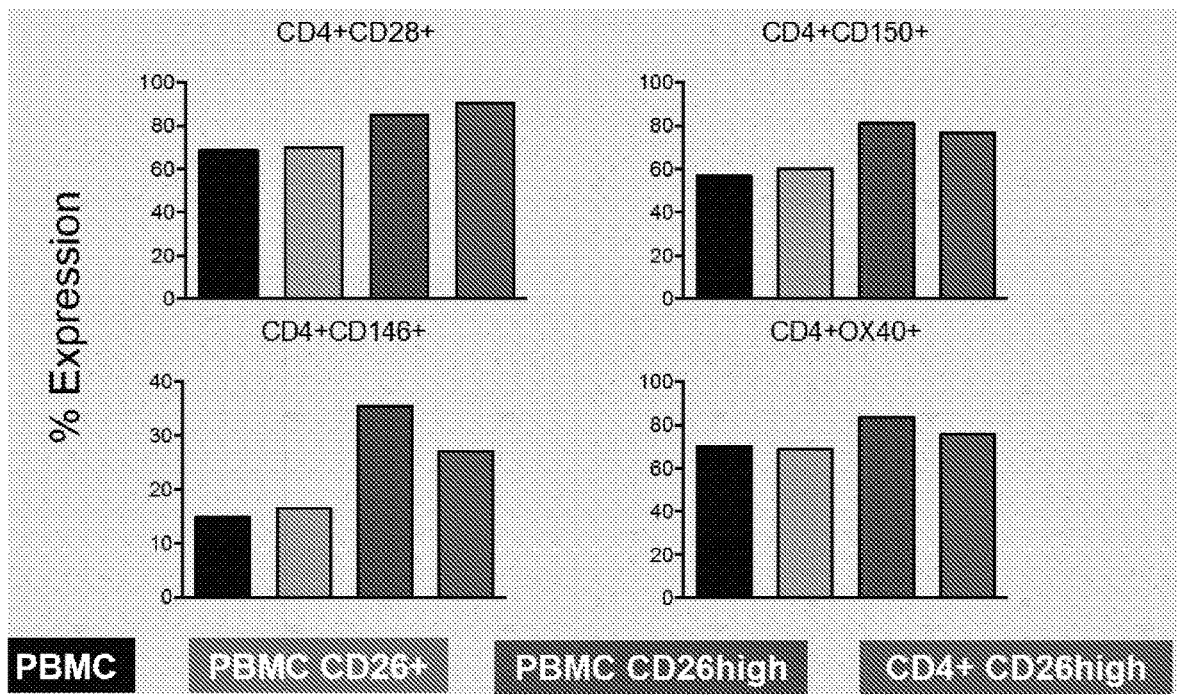
Figure 32F:
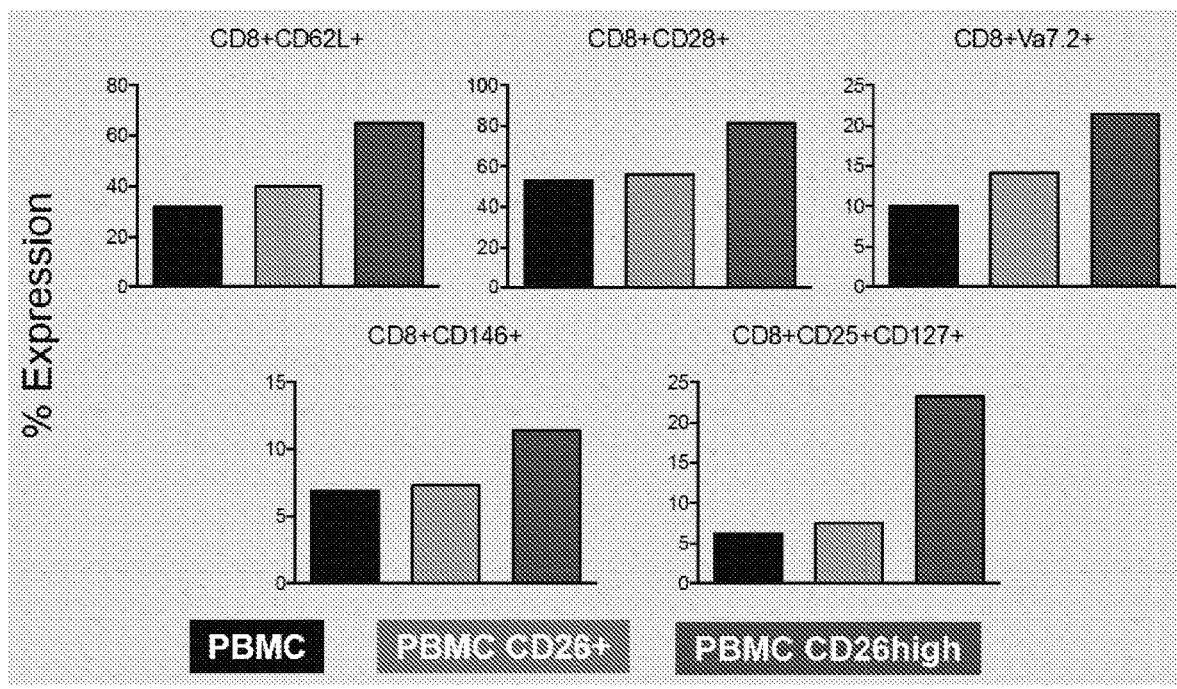
Figure 32G:
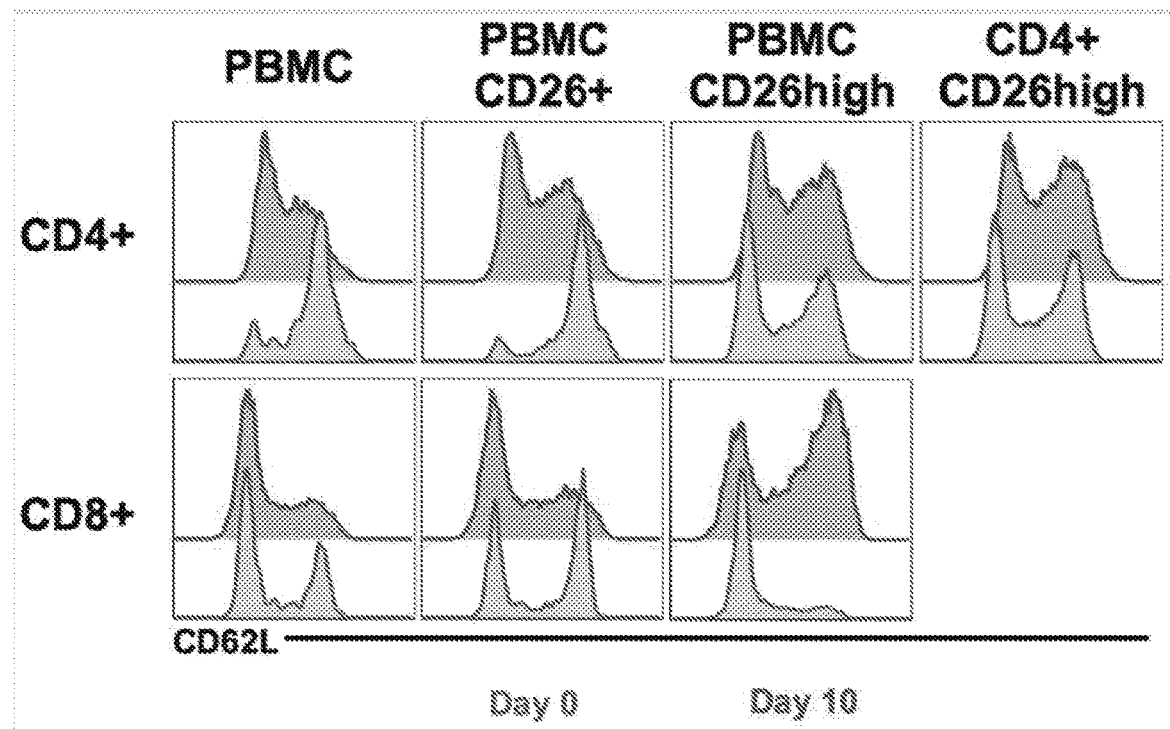
Figure 32H:
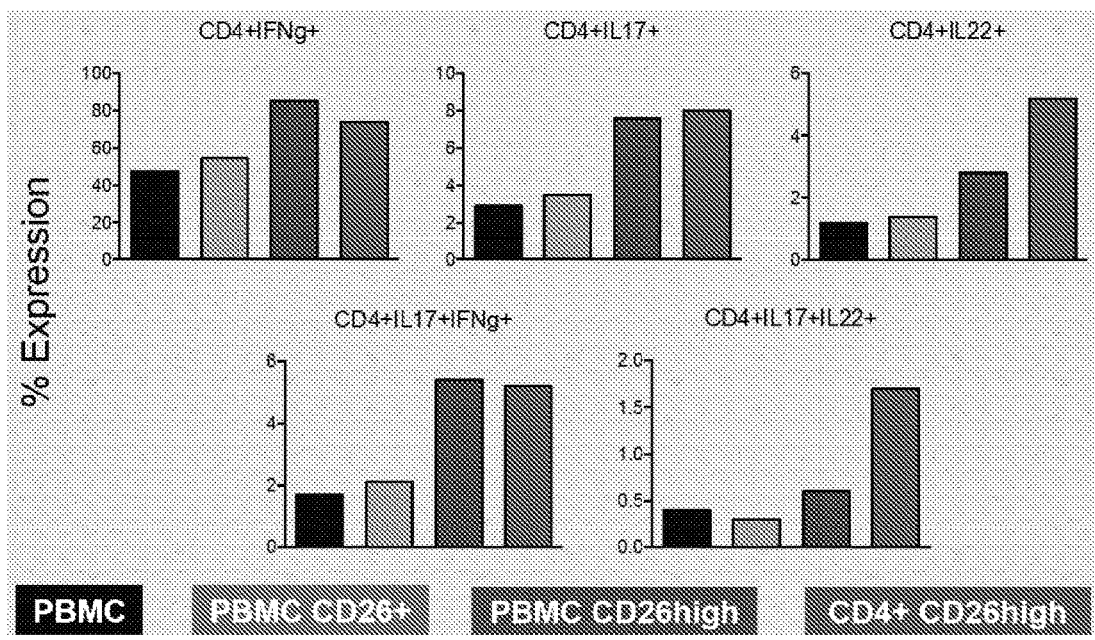
Figure 32I:
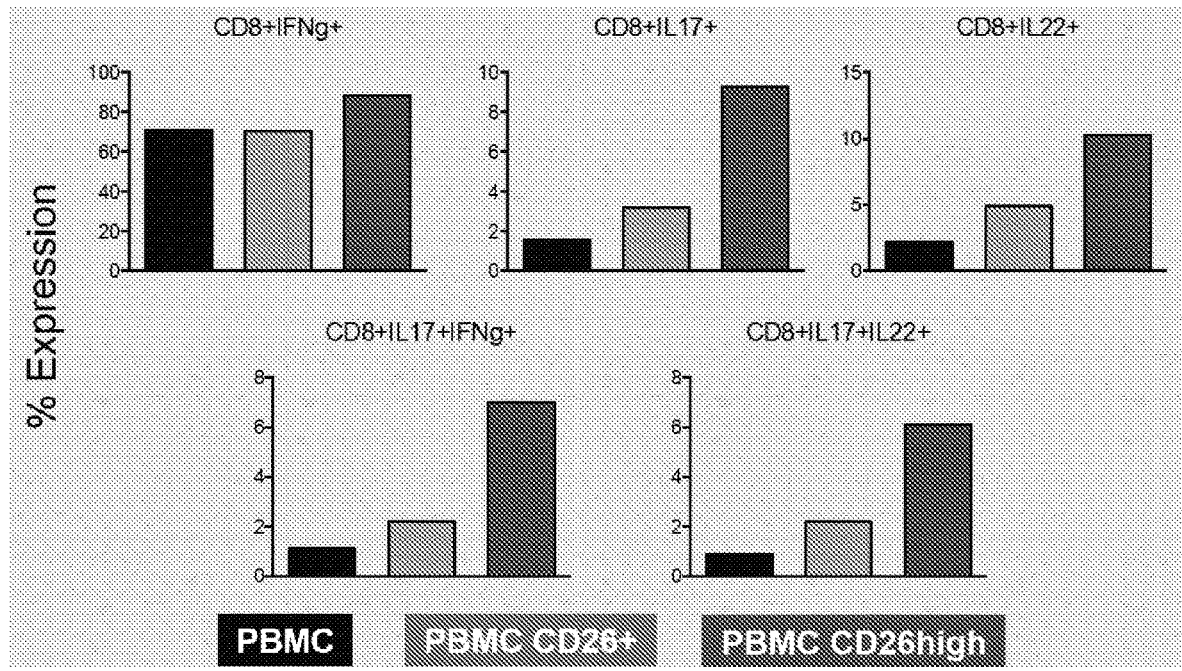
Figure 32J:
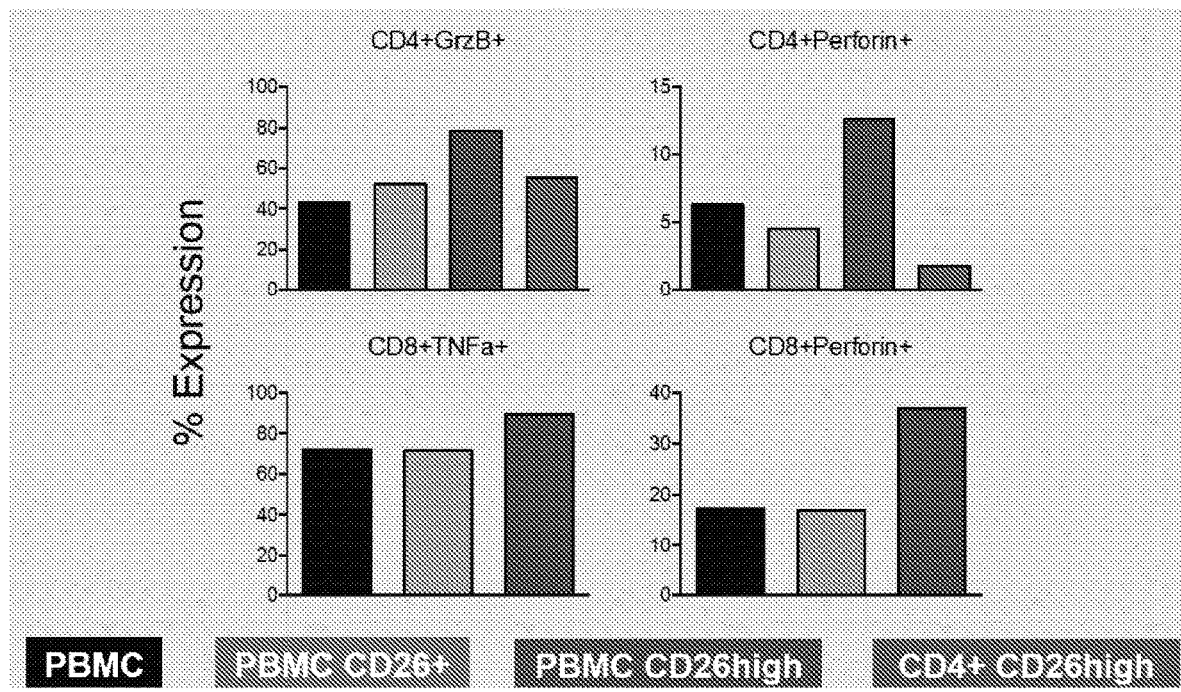

Finally, a study was performed to analyze the effect of CD26 expression in peripheral blood mononuclear cells (PBMC) as compared to $CD4^+CD26^{high}$ T cells. Peripheral blood mononuclear cells (PBMC) and $CD4^+$ T cells were sorted for their expression of CD26 by flow cytometry, CD3/ICOS bead activated and expanded for 10 days with IL-2. It was found that PBMC $CD26^{high}$ grow more rapidly and retain $CD4^+$ T cells better than other PBMC subsets and have a more diverse phenotype (FIGS. 32B, 32C). $CD4^+$ T cells from PBMC $CD26^{high}$ cultures are memory cells skewed to a Th1/Th17 phenotype and have heightened co-stimulatory markers (FIGS. 32D, 32E). In addition, the PBMC $CD26^{high}$ cultures contained more durable memory and cytokine receptors to enable engraftment (FIG. 32F). Interestingly, the $CD4^+$ and $CD8^+$ T cells from PBMC $CD26^{high}$ cultures are more cytotoxic than the other subsets (FIG. 32J).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,844,905
U.S. Pat. No. 5,846,945
U.S. Pat. No. 5,885,796
U.S. Pat. No. 6,207,156
U.S. Pat. No. 6,225,042
U.S. Pat. No. 6,355,479
U.S. Pat. No. 6,362,001
U.S. Pat. No. 6,410,319
U.S. Pat. No. 6,451,995
U.S. Pat. No. 6,790,662
U.S. Pat. No. 7,070,995
U.S. Pat. No. 7,109,304
U.S. Pat. No. 7,265,209
U.S. Pat. No. 7,354,762
U.S. Pat. No. 7,446,179
U.S. Pat. No. 7,446,190
U.S. Pat. No. 7,446,191
U.S. Pat. No. 8,008,449
U.S. Pat. No. 8,017,114
U.S. Pat. No. 8,119,129
U.S. Pat. No. 8,252,592
U.S. Pat. No. 8,324,353
U.S. Pat. No. 8,329,867

U.S. Pat. No. 8,339,645
U.S. Pat. No. 8,354,509
U.S. Pat. No. 8,398,282
U.S. Pat. No. 8,479,118
U.S. Pat. No. 8,735,553
U.S. Patent Publication No. 2002/131960,
U.S. Patent Publication No. 2005/0260186
U.S. Patent Publication No. 2006/0104968
U.S. Patent Publication No. 2009/0004142
U.S. Patent Publication No. 2009/0017000
U.S. Patent Publication No. 2011/0008369
U.S. Patent Publication No. 2013/0149337
U.S. Patent Publication No. 2013/287748
U.S. Patent Publication No. 2014/022021
U.S. Patent Publication No. 2014/0294898
EP2537416
WO 00/37504
WO 01/14424
WO 98/42752
WO1995/001994
WO1998/042752
WO2000/037504
WO2000/14257
WO2001014424
WO2007/103009
WO2012/129514
WO2013/071154
WO2013/123061
WO2013/126726
WO2013/166321
WO2014/031687
WO2014/055668
WO2014/055668 A1
WO2015/016718
Acosta-Rodriguez et al., Surface phenotype and antigenic specificity of human interleukin 17-producing T helper memory cells. *Nat. Immunol.* 8, 639-646, 2007.
Alsuliman A, et al. A subset of virus-specific CD161+ T cells selectively express the multidrug transporter MDR1 and are resistant to chemotherapy in AML. *Blood* 129, 740-758, 2017.
Austin-Ward and Villaseca, 1998.
Ausubel et al., *Current Protocols in Molecular Biology*, Greene Publishing Associates and John Wiley & Sons, NY, 1994.
Barreira da Silva et. al. *Nat Immunol* 16, 850-858, 2015.
Bengsch et al., Human Th17 cells express high levels of enzymatically active dipeptidylpeptidase IV (CD26). *J. Immunol.* 188, 5438-5447, 2012.
Betts et al., HIV nonprogressors preferentially maintain highly functional HIV-specific CD8+ T cells. *Blood* 107, 4781-4789, 2006.
Brahmer J R, et al. *J Clin Oncol* 28, 3167-3175, 2010.
Bukowski et al., 1998.
Camacho et al., *J Clin Oncology* 22(145): Abstract No. 2505 (antibody CP-675206), 2004.
Carpenito et al., *Proc Natl Acad Sci USA* 106, 3360-3365, 2009.
Carter et al., 2008.
Chang et al., T helper 17 cells play a critical pathogenic role in lung cancer. *Proc. Natl. Acad. Sci. U.S.A.* 111, 5664-5669, 2014.
Chothia et al., EMBO J. 7:3745, 1988.
Christodoulides et al., 1998.
Cohen et al., *J Immunol.* 175:5799-5808, 2005.
Craddock J A, et al. *J Immunother* 33, 780-788, 2010.
Davidson et al., 1998.
Davila et al., *PLoS ONE* 8(4): e61338, 2013.
Fan et al., *Adv Exp Med Biol* 524, 165-174, 2003.
Fedorov et al., *Sci. Transl. Medicine,* 5(215), December 2013.
Gattinoni et al., A human memory T cell subset with stem cell-like properties. *Nat. Med.* 17, 1290-1297, 2011.
Hanibuchi et al., 1998.
Hedin K E. Chemokines: new, key players in the pathobiology of pancreatic cancer. *Int J Gastrointest Cancer* 31, 23-29, 2002.
Heemskerk et al., *Hum Gene Ther.* 19:496-510, 2008.
Hellstrand et al., 1998
Hollander 2012.
Hui and Hashimoto, 1998.
Hurwitz et al., Proc Natl Acad Sci USA 95(17): 10067-10071, 1998.
Janeway et al, Immunobiology: The Immune System in Health and Disease, 3$^{rd}$ Ed., Current Biology Publications, p. 4:33, 1997
Johnson et al., *Blood* 114:535-46, 2009.
Jores et al., Pwc. Nat'l Acad. Sci. U.S.A. 87:9138, 1990.
Kabat et al., "Sequences of Proteins of Immunological Interest, US Dept. Health and Human Services, Public Health Service National Institutes of Health, 5$^{th}$ ed, 1991.
Kim and Cantor, CD4 T-cell subsets and tumor immunity: the helpful and the not-so-helpful. *Cancer Immunol Res* 2, 91-98, 2014.
Klebanoff C A, et al. *Proc Natl Acad Sci USA* 102, 9571-9576, 2005.
Laird and Ware, Random-effects models for longitudinal data. *Biometrics* 38, 963-974, 1982.
Leal et al., 2014.
Lee et al., Induction and molecular signature of pathogenic TH17 cells. *Nat. Immunol.* 13, 991-999, 2012.
Lefranc et al., Dev. Comp. Immunol. 27:55, 2003.
Li, Nat Biotechnol. 23:349-354, 2005.
Liu W, et al. *J Exp Med* 203, 1701-1711, 2006.
Melero et al., *Cancer Discov* 4, 522-526, 2014.
Mellman et al., Nature 480:480-489, 2011.
Mokyr et al. Cancer Res 58:5301-5304, 1998.
Moon E K, et al. *Clin Cancer Res* 17, 4719-4730, 2011.
Muranski et al., Tumor-specific Th17-polarized cells eradicate large established melanoma. *Blood* 112, 362-373, 2008.
Muranski P, et al. Th17 cells are long lived and retain a stem cell-like molecular signature. *Immunity* 35, 972-985, 2011.
Ohnuma et al., *Front Biosci* 13, 2299-2310, 2008.
Pardoll, Nature Rev Cancer 12:252-264, 2012.
Parkhurst et al., Clin Cancer Res. 15: 169-180, 2009.
Paulos et al., The inducible costimulator (ICOS) is critical for the development of human T(H)17 cells. *Sci. Transl. Med.* 2, 55ra78, 2010.
Qin et al., 1998.
Remington's Pharmaceutical Sciences 22nd edition, 2012.
Rizvi N A, et al. *Lancet Oncol* 16, 257-265, 2015.
Rosenberg S A, et al. *Clin Cancer Res* 17, 4550-4557, 2011.
Sadelain et al., Cancer Discov., 3(4): 388-398, April 2013.
Salgado et al., *Cytometry A* 81, 843-855, 2012.
Sambrook et al., *Molecular Cloning: A Laboratory Manual*, 3$^{rd}$ ed., Cold Spring Harbor Press, Cold Spring Harbor, N.Y. 2001.
Sharma et al., *Immunology* 145, 443-453, 2015.
Shah et al., 2013
Singh et al., 2008.
Singh et al., 2011.
Teicher 2009.

Teicher 2014.
Terakuraet et al., Blood. 1:72-82, 2012.
Turtle et al., Curr. Opin. Immunol., 24(5): 633-39, October 2012.
Varela-Rohena et al., Nat Med. 14: 1390-1395, 2008.
Wang et al., Eur J Immunol 37, 129-138, 2007.
Wang et al., J Immunother. 35(9):689-701, 2012.
Weng et al., Nat Rev Immunol 12, 306-315, 2012.
Wu et al., Cancer, 18(2): 160-75, March, 2012.
Yu N, et al. *Inflammation* 35, 1773-1780, 2012.

What is claimed is:

1. A method of treating cancer in a subject comprising administering an effective amount of T cells to the subject, wherein at least 10 percent of the T cells are $CD26^{high}$ T cells, wherein said T cells have been isolated from a peripheral blood mononuclear cell (PBMC) population, and wherein said T cells have been activated and expanded in culture in the presence of anti-CD3 beads, anti-CD28 beads, and/or anti-ICOS beads at a beads to T cell ratio of 1:5 to 1:25 prior to administering to the subject, wherein no antigen-specific stimulation has been performed on said T cells which have increased secretion of IL-17A, IFN-γ, and IL-2 after activation and expansion.

2. The method of claim 1, wherein at least 50 percent of the T cells are $CD26^{high}$ T cells.

3. The method of claim 1, wherein at least 75 percent of the T cells are $CD26^{high}$ T cells.

4. The method of claim 1, wherein the $CD26^{high}$ T cells comprise activated $CD26^{high}$ T cells produced by sorting $CD26^{high}$ T cells from the PBMC population.

5. The method of claim 4, wherein sorting comprises magnetic-activated cell sorting or fluorescence-activated cell sorting for $CD26^{high}$ cells.

6. The method of claim 1, wherein the cancer is bladder cancer, breast cancer, clear cell kidney cancer, head/neck squamous cell carcinoma, lung squamous cell carcinoma, melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

7. The method of claim 1, wherein the cancer is mesothelioma, pancreatic cancer, or ovarian cancer.

8. The method of claim 1, wherein the $CD26^{high}$ cells are activated $CD26^{high}$ $CD4^+$ T cells produced by direct purification from a PBMC cell population.

9. The method of claim 1, wherein the T cell population comprises $CD4^+$ and/or $CD8^+$ T cells.

10. The method of claim 1, wherein the $CD26^{high}$ T cells are produced by engineering T cells to express CD26.

11. The method of claim 10, wherein engineering comprises introducing CD26-encoding mRNA to the T cells.

12. The method of claim 1, wherein the activated $CD26^{high}$ T cells are autologous.

13. The method of claim 1, further comprising lymphodepletion of the subject prior to administration of the activated $CD26^{high}$ T cells.

14. The method of claim 13, wherein lymphodepletion comprises administration of cyclophosphamide and/or fludarabine.

15. The method of claim 1, further comprising administering at least a second therapeutic agent.

16. The method of claim 15, wherein the at least a second therapeutic agent comprises CD8+ T cells.

17. The method of claim 16, wherein the CD8+ T cells are engineered to express a chimeric antigen receptor (CAR)-comprising an antigen binding region which binds a tumor associated antigen selected from the group consisting of tEGFR, Her2, CD19, CD20, CD22, mesothelin, tyrosinase, CEA, CD23, CD24, CD30, CD33, CD38, CD44, EGFR, EGP-2, EGP-4, EPHa2, ErbB2, FBP, MAGE-A1, MUC1, NY-ESO-1, and MART-1.

18. The method of claim 15, wherein the at least a second therapeutic agent comprises immunotherapy.

19. The method of claim 18, wherein the immunotherapy is an immune checkpoint inhibitor.

20. The method of claim 19, wherein the immune checkpoint inhibitor is a programmed cell death protein 1 (PD-1) inhibitor.

21. The method of claim 1, wherein the cells have been expanded for at least 1 day.

22. The method of claim 1, wherein the cells have been expanded for at least 5 days.

23. The method of claim 1, wherein the anti-CD3, anti-CD28, and/or anti-ICOS beads to T cell ratio for activation is 1:5.

* * * * *